(12) United States Patent
Hayashi et al.

(10) Patent No.: US 9,371,274 B2
(45) Date of Patent: Jun. 21, 2016

(54) COMPOUND HAVING READ-THROUGH ACTIVITY

(71) Applicant: The University of Tokyo, Tokyo (JP)

(72) Inventors: Yoshio Hayashi, Tokyo (JP); Akihiro Taguchi, Tokyo (JP); Fumika Yakushiji, Tokyo (JP); Yuri Yamazaki, Tokyo (JP); Ryoichi Matsuda, Tokyo (JP); Masataka Shiozuka, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/291,861

(22) Filed: May 30, 2014

(65) Prior Publication Data

US 2014/0364642 A1    Dec. 11, 2014

Related U.S. Application Data

(63) Continuation-in-part of application No. PCT/JP2012/081120, filed on Nov. 30, 2012.

(30) Foreign Application Priority Data

Dec. 1, 2011    (JP) ................................. 2011-263404

(51) Int. Cl.
  *A61K 31/16*    (2006.01)
  *A61K 31/197*   (2006.01)
  (Continued)

(52) U.S. Cl.
  CPC .................................... *C07C 243/34* (2013.01)

(58) Field of Classification Search
  CPC ..... C07C 243/12; A61K 31/16; A61K 31/197
  USPC .................... 514/664, 565; 560/169; 564/464
  See application file for complete search history.

(56) References Cited

U.S. PATENT DOCUMENTS 3,962,317 A * 6/1976 Curran .......................... 560/158
4,065,495 A   12/1977 Umezawa et al.
(Continued)

FOREIGN PATENT DOCUMENTS

JP    52-59112      5/1977
WO    WO 02/102361  12/2002

OTHER PUBLICATIONS

Shinichi Kondo, et al. "Syntheses and Properties of Negamycin Analogs Modified the 6-Hydroxy 13-Lysine Moiety" The Journal of Antibiotics 1976, 29(2):208-211.*

(Continued)

*Primary Examiner* — Kamal Saeed
*Assistant Examiner* — Janet L Coppins
(74) *Attorney, Agent, or Firm* — Clark G. Sullivan; Troutman Sanders LLP

(57) ABSTRACT

[Problem] Provision of a novel compound having read-through activity and a drug for the treatment of nonsense mutation-type disease containing this compound.
[Solution] A compound represented by the following general formula (1):

[Chemical Formula 1]

$$R_1\text{-}N(R_2)\text{-}(CH_2)_n\text{-}CH(X)\text{-}C(=O)\text{-}N(R_5)\text{-}N(R_6)\text{-}CH_2\text{-}COOR_7 \quad (1)$$

and a pharmaceutical composition containing this compound.

13 Claims, 4 Drawing Sheets

(51) Int. Cl.
   *C07C 243/12*   (2006.01)
   *C07C 243/34*   (2006.01)

(56) References Cited

U.S. PATENT DOCUMENTS

2003/0109583 A1   6/2003   Raju et al.
2005/0014835 A1   1/2005   Arakawa et al.

OTHER PUBLICATIONS

Shinichi Kondo, et al. "3-EPI Deoxynegamycin and Leucyl-3-EPI-Deoxynegamycin Produced by Streptomyces" The Journal of Antibiotics 1977, 30(12):1137-1139.*

William V. Curran, et al. "The Synthesis of Deoxynegamycin and Some Related Compounds" The Journal of Antibiotics 1978, 31(9):914-918.

Hideo Iida, et al. "Enantioselective Total Synthesis of (+)-Negamycin and (−)-Epinegamycin by an Asymmetric 1,3-Dipolar Cycloaddition" J. Am. Chem. Soc. 1986, 108:4647-4648.

International Search Report dated Jan. 22, 2013, which issued during prosecution of International Application No. PCT/JP2012/081120, which corresponds to the present application.

Shinichi Kondo, et al. "Syntheses and Properties of Negamycin Analogs Modified the δ-Hydroxy β-Lysine Moiety" The Journal of Antibiotics 1976, 29(2):208-211.

L. Politano, et al. "Gentamicin administration in Duchenne patients with premature stop codon. Preliminary results" Acta Myologica 2003, 22:15-21.

Yi-Fong Wang, et al. "Stereocontrolled Synthesis of (+)-Negamycin from an Acyclic Homoallylamine by 1,3-Asymmetric Induction" J. Am. Chem. Soc. 1982, 104:6465-6466.

Michael Wilschanski, M.D. et al. "Gentamicin-Induced Correction of CFTR Function in Patients with Cystic Fibrosis and CFTR Stop Mutations" The New England Journal of Medicine 2003, 349(15):1433-1441.

* cited by examiner

COMPOUND HAVING READ-THROUGH ACTIVITY

The present invention is a continuation-in-part application claiming priority to Japanese Patent Application 2011-263404 filed on Dec. 1, 2011 and International Application PCT/JP2012/081120 filed on Nov. 30, 2012.

TECHNICAL FIELD

The present invention relates to a novel compound having read-through activity. The present invention also relates to a pharmaceutical composition containing the compound and use of the compound and the pharmaceutical composition to treat genetic disease.

BACKGROUND ART

In genetic disease, abnormalities occur in genes for various reasons and can interfere with life activities. Abnormalities among them due to nonsense mutations, because the stop codon occurs in the middle of a structural gene, suppress expression of a full-length protein having a function, triggering various genetic diseases. There are said to be 2500 or more nonsense mutation-type genetic diseases. Replacement therapy is exceptionally successful in hormone deficiency due to genetic abnormality, but there generally is not yet any direct method of treating genetic diseases. We currently rely on symptomatic treatment to alleviate symptoms, and no treatment leading to a complete cure has been discovered. Gene therapy is one of the most promising treatments, but this treatment has not reached a stage that can withstand clinical application.

Duchenne muscular dystrophy seen in male children can be given as an example of a typical genetic disease. In this disease, a mutation occurs on the dystrophin gene present in the X chromosome. A stop codon is formed by this mutation (premature stop codon), and expression of normal dystrophin and dystrophin-associated proteins is inhibited by the interruption and cessation of translation at this mutation site. As a result, dystrophin proteins are lacking, and muscular dystrophy occurs.

The use of compounds having read-through activity to treat nonsense mutation-type diseases has been reported. When a specific compound is administered to a patient having a premature stop codon due to a nonsense mutation and lacking a specific protein, a phenomenon is seen whereby the compound acts on the ribosomes and the ribosomes read through and translate the stop codon. This phenomenon is called read-through. As a result of read-through, a wild-type normal protein is synthesized, and the disease can be treated. Gentamicin, which is an aminoglycoside antibiotic, is known as a compound having such read-through activity. When gentamicin is administered to a Duchenne muscular dystrophy patient, dystrophin proteins are reported to accumulate (see Non-patent Reference 1). It is also reported that the typical electrophysiological abnormalities can be normalized by administering locally to the airway epithelium of a cystic fibrosis patient (see Non-patent Reference 2). However, gentamicin, like other aminoglycoside antibiotics, has severe renal toxicity and ototoxicity and is unsuited to this treatment method which will likely require long-term administration. It is also necessary to separate the drug effect from the antimicrobial activity that this compound has in consideration of adverse effects and the like.

Negamycin (methylhydrazinoacetic acid-linked δ-hydroxy-β-lysine: NM), a dipeptide antibiotic, is also reported to have read-through activity. When negamycin is administered to muscular dystrophy model mice, the expression of dystrophin is reported to recover (see Patent Reference 1). However, since negamycin also has high antimicrobial activity, it is desirable in consideration of adverse effects to provide a therapeutic drug for nonsense mutation-type diseases having selective read-through activity.

PRIOR ART REFERENCES

Patent References

Patent Reference 1: International Publication WO2002/102361 pamphlet

NON-PATENT REFERENCES

Non-Patent Reference 1: Acta. Myol., 22, p. 15-21 (2003
Non-Patent Reference 2: N. Engl. J. Med., 349, p. 1433-1441 (2003)
Non-Patent Reference 3: Y. F. Wang et al., J. Am. Chem. Soc., 104, p. 6465-6466 (1982)
Non-Patent Reference 4: H. Iida et al., J. Am. Chem. Soc., 108, p. 4647-4648 (1986)

SUMMARY OF THE INVENTION

Problems to be Solved by the Invention

The purpose of the present invention is to provide a novel compound having read-through activity and a therapeutic drug for nonsense mutation-type diseases containing this compound.

Means Used to Solve the Above-Mentioned Problems

The present inventors turned their attention to negamycin and natural analogs as regards the above problems, and, as a result of in-depth studies, succeeded in producing novel derivatives having potent read-through activity and thereby perfected the present invention.

Negamycin has a hydroxyl group at position 5 of the amino acids that constitute its left flank. The present inventors, however, confirmed during in-depth studies that 5-epi-negamycin, which differs from negamycin in the configuration of this position 5 hydroxyl group, also has read-through activity and discovered that this hydroxyl group does not contribute to the read-through activity. Compounds not having a hydroxyl group at position 5 of the amino acids that constitute the left flank of negamycin were thus unexpectedly discovered to have the same or greater read-through activity as negamycin, and the present invention was perfected.

Specifically, the present invention is:

(1) A compound represented by the following general formula (1):

[Chemical Formula 1]

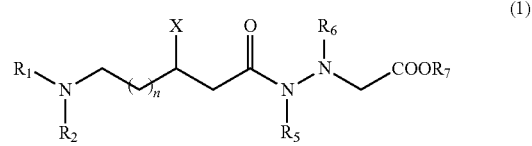

in which
R$_1$ and R$_2$ are each independently hydrogen, an optionally substituted C$_1$-C$_6$ alkyl group, C$_2$-C$_6$ alkenyl group, C$_2$-C$_6$ alkynyl group, C$_6$-C$_{10}$ aralkyl group, C$_6$-C$_{10}$ aralkenyl group, sulfonyl group, cyclic amine, or guanidyl group,
R$_1$ and R$_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, and where the heterocycle or heteroaryl may be substituted by a $C_1$-$C_6$ alkyl group, $C_2$-$C_6$ alkenyl, or $C_2$-$C_6$ alkynyl, $C_6$-$C_{10}$ aralkyl group, $C_6$-$C_{10}$ aralkenyl group, $R_1$ and $R_2$ also may be an amino acid residue introduced via an amide bond formed together with the nitrogen atom to which they are bonded;

X is $N(R_3)(R_4)$, an N-linked amino acid residue, or a $C_1$-$C_6$ alkyl group containing an amino group having a substituent, where the substituent of this amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, and where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_5$ is a $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_7$ is hydrogen, a $C_1$-$C_6$ alkyl group, substituted or unsubstituted aralkyl group, or $C_3$-$C_7$ cycloalkyl group, where the substituent of the substituted aralkyl group is a halogen, $C_1$-$C_4$ alkyl group, alkoxy group, hydroxy group, nitro group, amino group, $C_1$-$C_6$ acyl group, or amino group modified by an alkyl group, sulfonic acid group; and n is an integer of 0-3, or a salt or solvate of the compound, (2) The compound according to (1) represented by the following general formula (3):

[Chemical Formula 2]

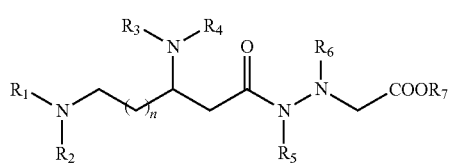

in which $R_1$, $R_2$, $R_3$, $R_4$, $R_5$, $R_6$, $R_7$, and n are as defined in (1), or a salt or solvate of the compound, (3) The compound according to (1), wherein the N-linked amino acid residue of X is selected from α-amino acids and β-amino acids, or a salt or solvate of the compound, (4) The compound according to (1) represented by the following general formula (5):

[Chemical Formula 3]

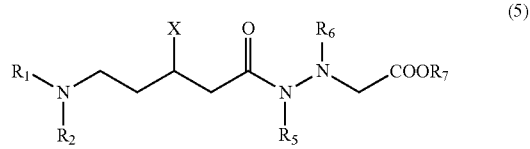

in which $R_1$, $R_2$, X, $R_3$, $R_4$, $R_5$, $R_6$, and $R_7$ are as defined in (1), or a salt or solvate thereof, (5) The compound according to (1) or (4), wherein $R_1$ and $R_2$ are an amino acid residue introduced via an amide bond formed together with the nitrogen atom to which they are bonded, and the amino acid residue is represented by the following formula (2):

[Chemical Formula 4]

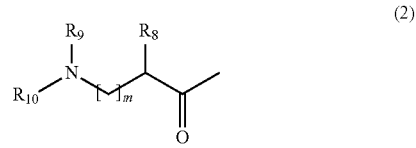

in which $R_8$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, substituents that these substituents can have are a halogen, hydroxyl group, carboxyl group, amino group, or amide group;

$R_9$, $R_{10}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_9$ and $R_{10}$ also may form, together with the nitrogen atom to which they are bonded, a three- to six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group; and m is an integer of 0-4, or a salt or solvate thereof, (6) The compound according to any of (1), (4), and (5), wherein the N-linked amino acid residue of X is represented by the following formula (4):

[Chemical Formula 5]

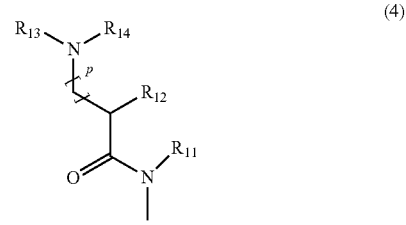

in which
- $R_{11}$ is hydrogen or an optionally substituted $C_1$-$C_6$ alkyl group;
- $R_{12}$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, where the substituents that these substituents can have are a halogen, hydroxyl group, carboxyl group, amino group, or amide group;
- $R_{13}$, $R_{14}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_8$ and $R_9$ also may form, together with the nitrogen atom to which they are bonded, a three- to six-membered heterocycle or heteroaryl bonded via N, may also contain 1-3 additional hetero atoms selected from the group consisting of O, N, and S as ring constituent members (for example, oxazolidine), where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, or $C_6$-$C_{10}$ aralkenyl group; and
- p is an integer of 0-3, or a salt or solvate thereof, (7) A pharmaceutical composition containing a compound represented by the following general formula (1):

[Chemical Formula 6]

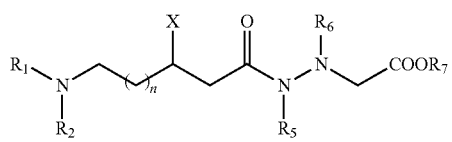

(1)

in which
- $R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group,
- $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group,
- $R_1$ and $R_2$ also may be an amino acid residue introduced via an amide bond formed together with the nitrogen atom to which they are bonded;
- X is $N(R_3)(R_4)$, an N-linked amino acid residue, or $C_1$-$C_6$ alkyl group containing an amino group having a substituent, where the substituent of the amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, or $C_6$-$C_{10}$ aralkenyl group;
- $R_5$ is a $C_1$-$C_4$ alkyl group, $C_2$-$C_4$ alkenyl group, or $C_2$-$C_4$ alkynyl group;
- $R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, or $C_6$-$C_{10}$ aralkenyl group;
- $R_7$ is hydrogen, a $C_1$-$C_6$ alkyl group, substituted or unsubstituted aralkyl group, $C_3$-$C_7$ cycloalkyl group, where the substituent of a substituted aralkyl group is a halogen, $C_1$-$C_4$ alkyl group, alkoxy group, hydroxy group, nitro group, amino group, $C_1$-$C_6$ acyl group, or amino group modified by an alkyl group, sulfonic acid group; and
- n is an integer of 0-3 or a salt or solvate of the compound, (8) The pharmaceutical composition according to (7) containing a compound represented by the following general formula (5):

[Chemical Formula 7]

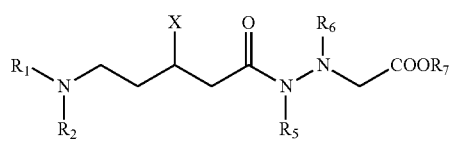

(5)

in which $R_1$, $R_2$, X, $R_3$, $R_4$, $R_5$, $R_6$, and $R_7$ are as defined in (7), or a salt or solvate of the compound, (9) The pharmaceutical composition according to (7) or (8) for use in the treatment or prevention of a disease caused by a nonsense mutation,

(10) The pharmaceutical composition according to (9), wherein the disease caused by a nonsense mutation is a disease selected from the group consisting of muscular dystrophy, Duchenne muscular dystrophy, infantile neuronal ceroid lipofuscinosis, multiple sclerosis, Alzheimer's disease, Tay-Sachs disease, neurodegenerative disease, Parkinson's disease, rheumatoid arthritis, graft-versus-host disease, arthritis, hemophilia, von Willebrand disease, ataxia telangiectasia, β-thalassemia, kidney stones, osteogenesis imperfecta, liver cirrhosis, neurofibromatosis, bullous disease, lysosomal storage disease, Hurler disease, familial hypercholesterolemia, cerebellar ataxia, nodular sclerosis, immunodeficiency, kidney disease, lung disease, cystic fibrosis, familial cholesterolemia, pigmentary retinopathy, amyloidosis, atherosclerosis, gigantism, dwarfism, hypothyroidism, hyperthyroidism, aging, obesity, Niemann-Pick disease, and Marfan syndrome, and

(11) The pharmaceutical composition according to (10), wherein the disease caused by a nonsense mutation is a disease selected from the group consisting of muscular dystrophy, cystic fibrosis, Hurler disease, and infantile neuronal ceroid lipofuscinosis.

Advantages of the Invention

The negamycin derivatives defined by general formula (1) of the present invention generally have better read-through activity than negamycin and are compounds useful as pharmaceutical products. The present invention can thus provide pharmaceutical compositions containing the compounds defined by general formula (1). The pharmaceutical compositions of the present invention can be used in the treatment or prevention of comprehensive diseases caused by nonsense mutations and in the treatment or prevention of cancers in which nonsense mutations of suppressor genes such as the p53 gene and the like participate, and are very useful.

BEST MODE FOR CARRYING OUT THE INVENTION

Figure 1:
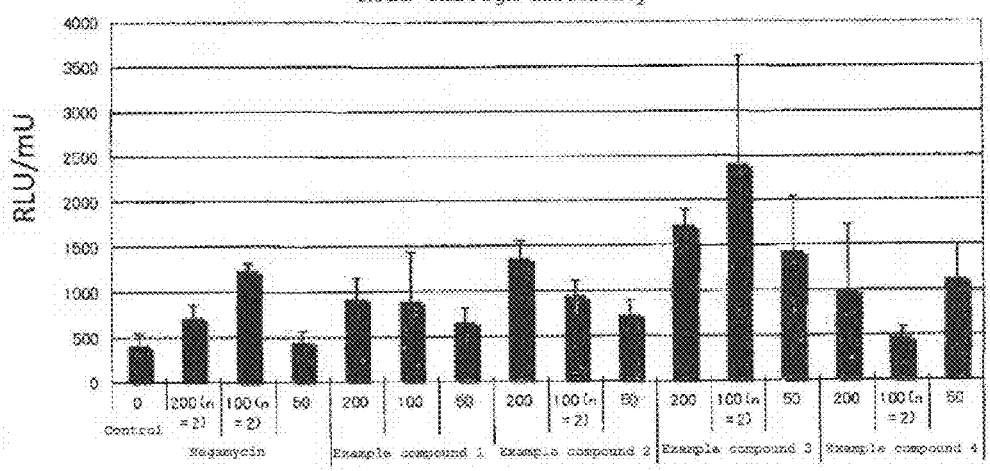
FIG. 1 is a graph showing the results of in vitro measurement of the read-through activity of compounds of the present invention.

The present invention is explained in detail below. Negamycin (methylhydrazinoacetic acid-linked δ-hydroxy-β-lysine) is a compound represented by the following chemical formula.

[Chemical Formula 8]

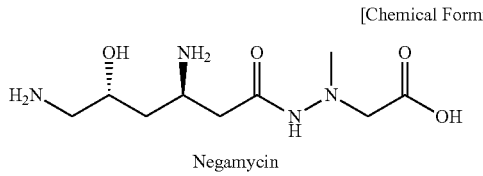

Negamycin

5-Epi-negamycin, which is an epimer, also has read-through activity. The present invention is based on the discovery that the configuration of this position 5 hydroxyl group does not contribute to the read-through activity. The compounds of the present invention are characterized by not having a hydroxyl group at position 5 of the amino acids that constitute the left flank of negamycin.

Their structural formula is shown below.

[Chemical Formula 9]

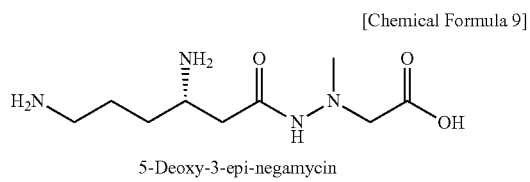

5-Deoxy-3-epi-negamycin

The compounds of the present invention can be synthesized by: reducing a protected α-amino acid, having a protected side chain amino group, to an alcohol, and deriving a sulfonic acid ester; from here, a nitrile group is introduced and subjected to alkali hydrolysis and condensation with a hydrazine unit; finally, the protecting groups are removed and refining is conducted. For example, a compound can be obtained from commercial Boc-Orn(Boc)-OH by the reaction shown in Scheme 1 of Example 1.

Compounds according to the present invention are compounds represented by the following general formula (1) or salts or solvates thereof.

[Chemical Formula 10]

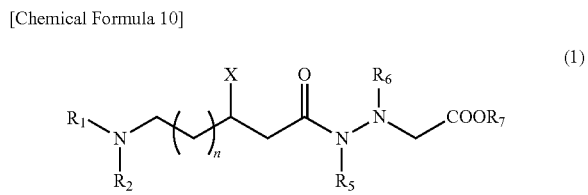

(1)

in which $R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group, $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group, $R_1$ and $R_2$ also may be an amino acid residue introduced via an amide bond formed together with the nitrogen atom to which they are bonded;

X is N($R_3$) ($R_4$), an N-linked amino acid residue, or $C_1$-$C_6$ alkyl group containing an amino group having a substituent, where the substituent of the amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_5$ is a $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, or $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group;

$R_7$ is hydrogen, a $C_1$-$C_6$ alkyl group, substituted or unsubstituted aralkyl group (benzyl group, phenethyl group, or the like), or $C_3$-$C_7$ cycloalkyl group, where the substituent of a substituted aralkyl group is a halogen, $C_1$-$C_4$ alkyl group, alkoxy group, hydroxy group, nitro group, amino group, $C_1$-$C_6$ acyl group, or amino group modified by an alkyl group, sulfonic acid group;

n is an integer of 0-3.

In a preferred embodiment in the present invention, $R_1$ and $R_2$ are an amino acid residue introduced via an amide bond formed together with the nitrogen atom to which they are bonded, represented by the following formula (2).

[Chemical Formula 11]

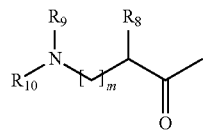

(2)

In formula (2), $R_8$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group;

$R_9$ and $R_{10}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_9$ and $R_{10}$ also may form, together with the nitrogen atom to which they are bonded, a three- to six-membered heterocycle or heteroaryl bonded via N, may also contain 1-3 additional hetero atoms selected from the group consisting of O, N, and S as ring constituent members (for example, oxazolidine and the like), where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group;

m is an integer of 0-4.

Substituents that the optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group in $R_8$ can have include a halogen, hydroxyl group, carboxyl group, amino group, amide group, or the like.

A preferred embodiment of the present invention is a compound represented by the following general formula (3), wherein X is $N(R_3)(R_4)$, or a salt or solvate of the compound.

[Chemical Formula 12]

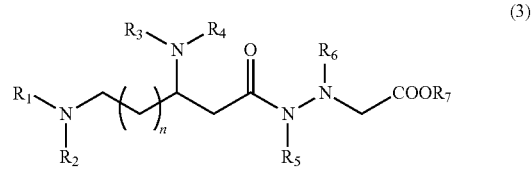

(3)

in which $R_1$, $R_2$, $R_3$, $R_4$, $R_5$, $R_6$, $R_7$, and n are as defined in general formula (1).

Another preferred embodiment of the present invention is a compound represented by formula (1), wherein X is an N-linked amino acid residue, or a salt or solvate of the compound. Here, examples of N-linked amino acids are α-amino acids and β-amino acids having $C_1$-$C_{12}$ in a side chain, preferably one containing an amino group, cyclic amine, guanidyl group, or oxygen atom in the side chain. More preferred as α-amino acids are leucine, isoleucine, valine, lysine, ornithine, threonine, arginine, asparagine, aspartic acid, glutamine, glutamic acid, serine, histidine, phenylalanine, alanine, glycine, tryptophan, tyrosine, N-methylleucine, 2,3-diaminopropanoic acid, 2,4-diaminobutyric acid, ornithine, lysine, α-hydroxyleucine, and the like, and more preferred as β-amino acids are β-alanine and the like. Chain or cyclic aliphatic hydrocarbons are also preferred as side chains consisting of $C_1$-$C_{12}$. Those having a branched structure at the β or γ position are more preferred, and examples include t-butylalkyl, sec-alkylalkyl, bicycloalkylalkyl groups, more specifically, t-butyl, t-butylmethyl, cyclohexylmethyl, cycloheptylmethyl, menthylmethyl, adamantylmethyl, decalinylmethyl, and the like.

In a preferred aspect of the present invention, the N-linked amino acid residue of X is represented by the following formula (4).

[Chemical Formula 13]

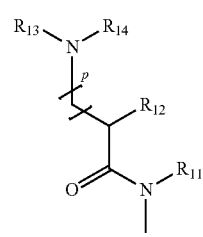

(4)

In formula (4), $R_{11}$ is hydrogen or an optionally substituted $C_1$-$C_6$ alkyl group;

$R_{12}$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group;

$R_{13}$, $R_{14}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_8$ and $R_9$ also may form, together with the nitrogen atom to which they are bonded, a three- to six-membered heterocycle or heteroaryl bonded via N, may also contain 1-3 additional hetero atoms selected from the group consisting of O, N, and S as ring constituent members (for example, oxazolidine), where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group;

p is an integer of 0-3.

Examples of the substituents that the optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group of $R_{12}$ can have are a halogen, hydroxyl group, carboxyl group, amino group, amide group. An optionally substituted $C_1$-$C_{10}$ alkyl group may be linear or branched and may form a cyclic structure.

Optionally substituted $C_4$-$C_9$ alkyl groups are preferred among the optionally substituted $C_1$-$C_{10}$ alkyl groups of $R_{12}$, and optionally substituted $C_7$-$C_9$ alkyl groups are more preferred.

In formula (4), when p is 0, the amino acid residue linked to N takes the form of an α-amino acid; when p is 1, it takes the form of a β-amino acid. Those preferred as α-amino acids and β-amino acids introduced by linking to N in formula (4) are the same as the preferred α-amino acids and β-amino acids listed above.

Another preferred embodiment of the present invention is a compound represented by the following general formula (5) wherein n in formula (1) is 1, or a salt or solvate of the compound.

[Chemical Formula 14]

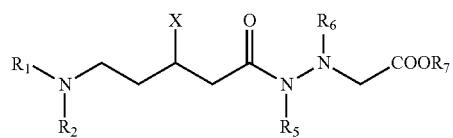

(5)

In a preferred embodiment of compounds of formula (3), $R_1$ and $R_2$ are an amino acid residue introduced via an amide bond formed together with the nitrogen atom to which they are bonded; this amino acid residue is represented by the above formula (2).

In a preferred embodiment of compounds of formula (3), the N-linked amino acid residue of X is also represented by the above formula (4).

Compounds of the following formulas (6)-(18) are given as specific examples of compounds of the present invention, but are not limited thereto.

[Chemical Formula 15]

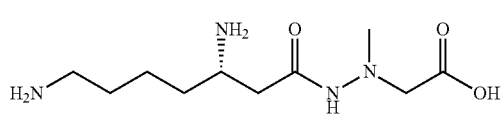

Example compound 1

(6)

[Chemical Formula 16]

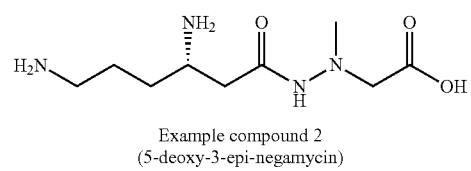

Example compound 2
(5-deoxy-3-epi-negamycin)

(7)

[Chemical Formula 17]

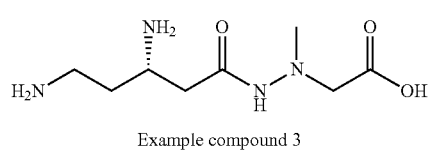

Example compound 3

(8)

[Chemical Formula 18]

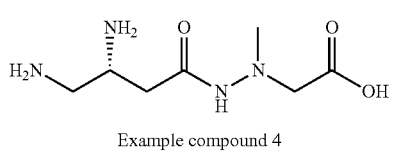

Example compound 4

(9)

[Chemical Formula 19]

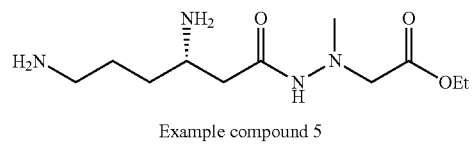

Example compound 5

(10)

[Chemical Formula 20]

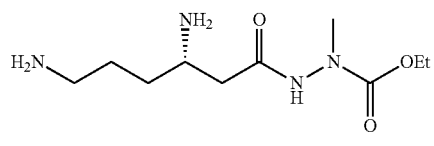

Example compound 6

(11)

[Chemical Formula 21]

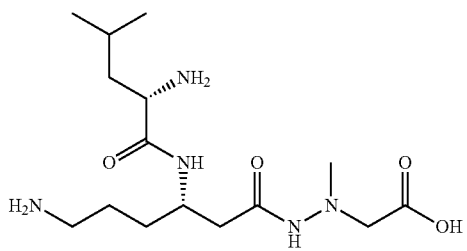

Example compound 7

(12)

[Chemical Formula 22]

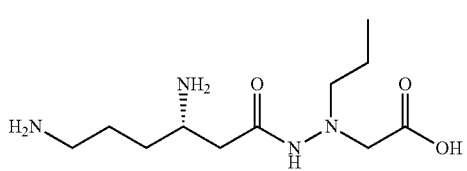

Example compound 8

(13)

[Chemical Formula 23]
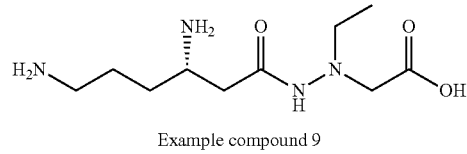
Example compound 9
[Chemical Formula 24]
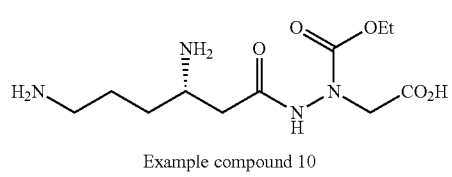
Example compound 10
[Chemical Formula 25]
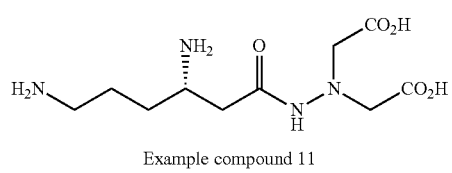
Example compound 11
[Chemical Formula 26]
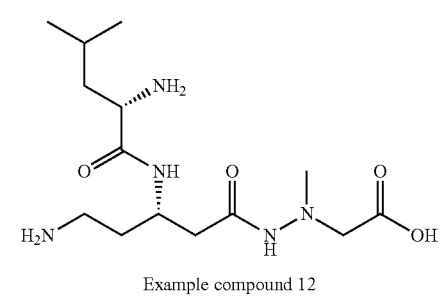
Example compound 12
[Chemical Formula 27]
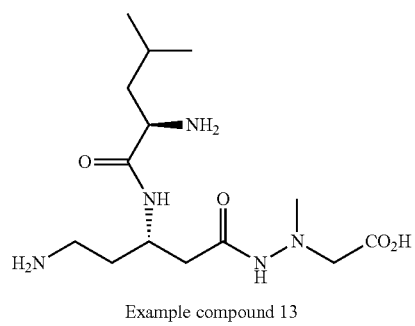
Example compound 13
[Chemical Formula 28]
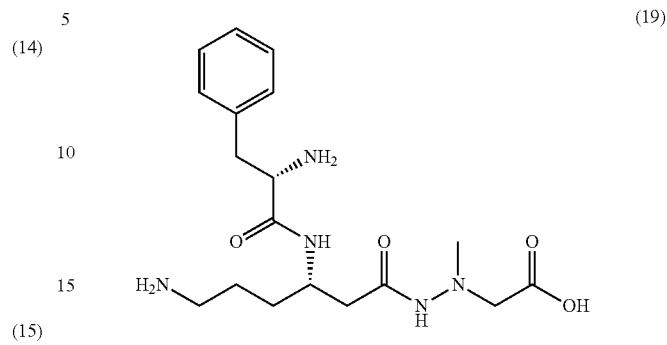
Example compound 14
[Chemical Formula 29]
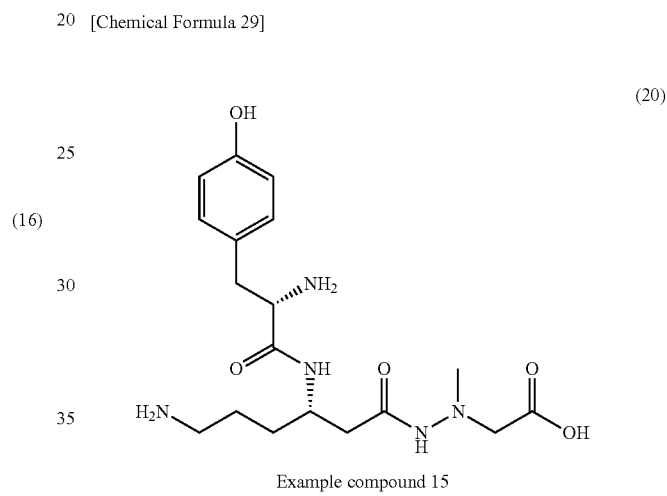
Example compound 15
[Chemical Formula 30]
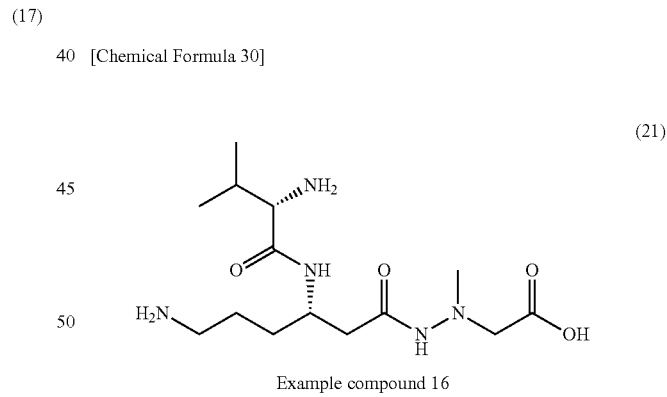
Example compound 16
[Chemical Formula 31]
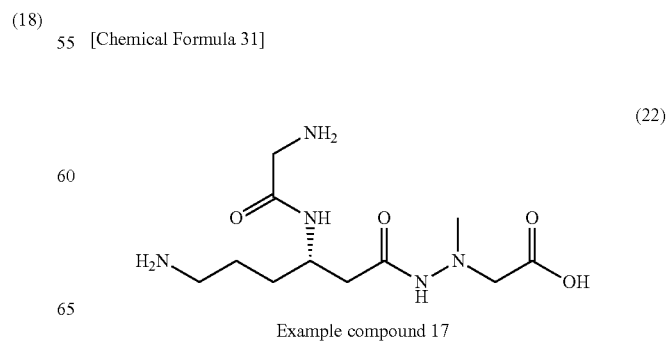
Example compound 17

[Chemical Formula 32]

(23)

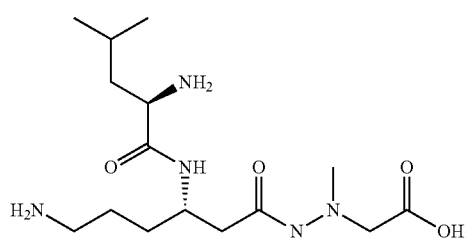

Example compound 18

[Chemical Formula 33]

(24)

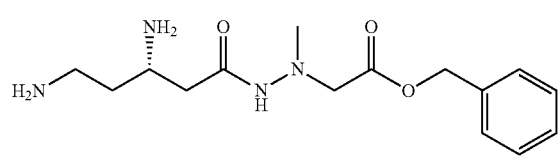

Example compound 19

[Chemical Formula 34]

(25)

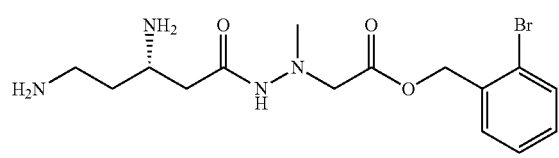

Example compound 20

[Chemical Formula 35]

(26)

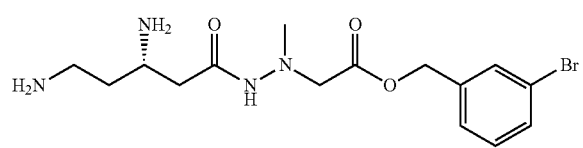

Example compound 21

[Chemical Formula 36]

(27)

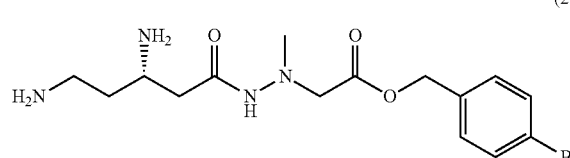

Example compound 22

[Chemical Formula 37]

(28)

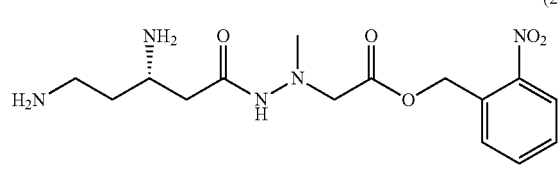

Example compound 23

[Chemical Formula 38]

(29)

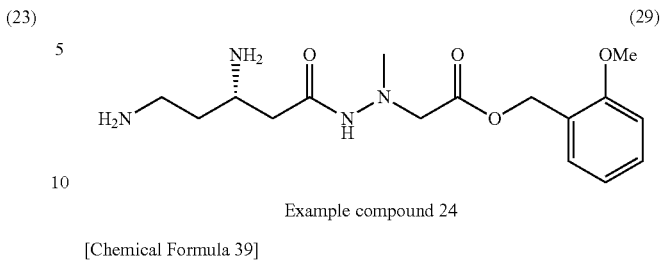

Example compound 24

[Chemical Formula 39]

(30)

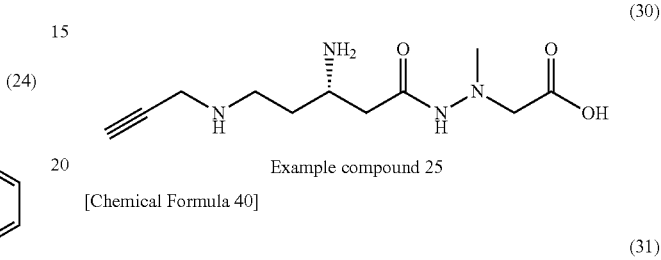

Example compound 25

[Chemical Formula 40]

(31)

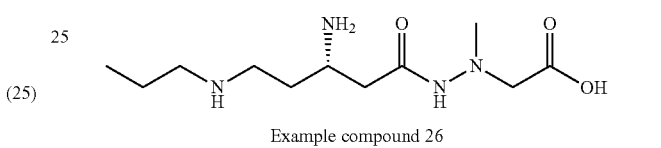

Example compound 26

[Chemical Formula 41]

(32)

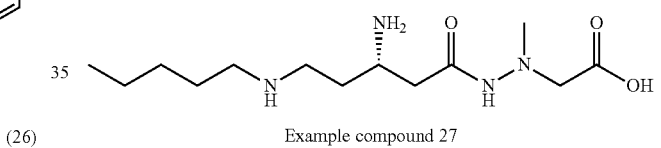

Example compound 27

[Chemical Formula 42]

(33)

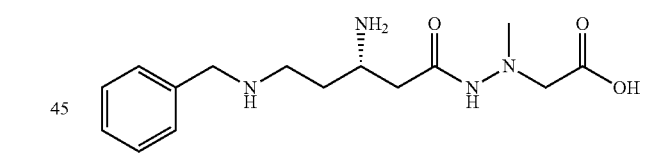

Example compound 28

[Chemical Formula 43]

(34)

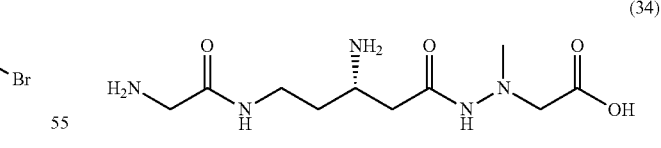

Example compound 29

[Chemical Formula 44]

(35)

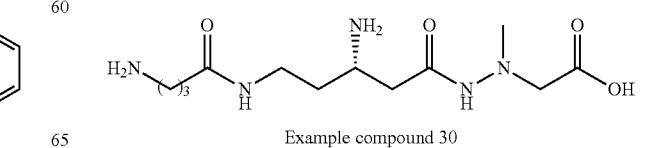

Example compound 30

[Chemical Formula 45]

(36)

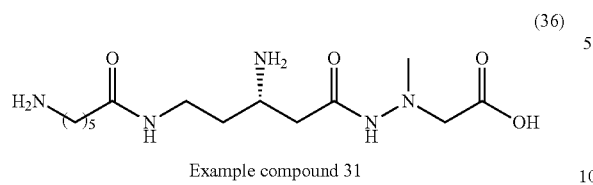

Example compound 31

[Chemical Formula 46]

(37)

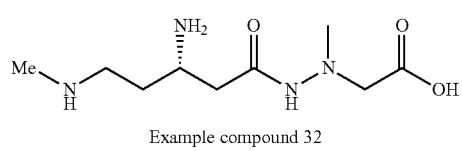

Example compound 32

[Chemical Formula 47]

(38)

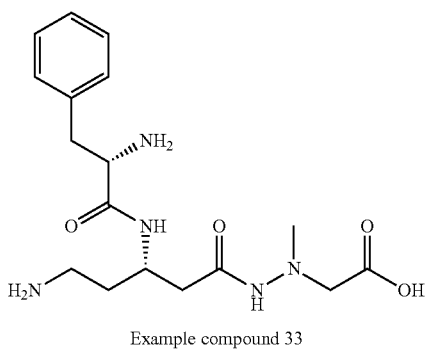

Example compound 33

[Chemical Formula 48]

(39)

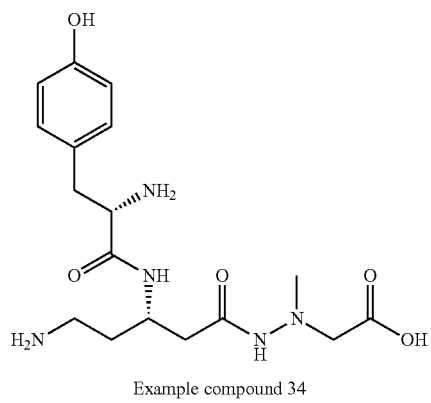

Example compound 34

[Chemical Formula 49]

(40)

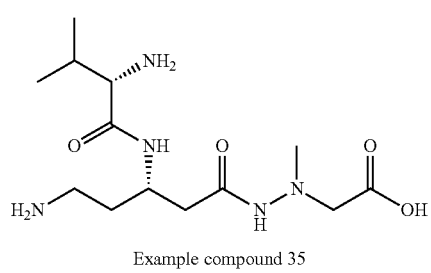

Example compound 35

[Chemical Formula 50]

(41)

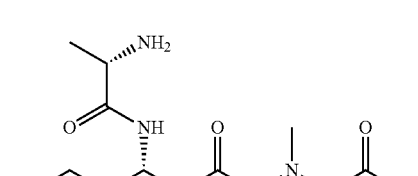

Example compound 36

[Chemical Formula 51]

(42)

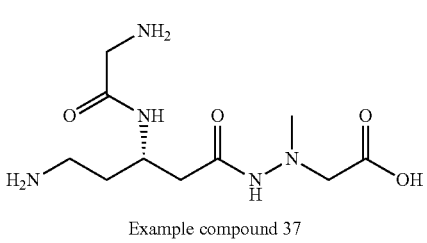

Example compound 37

[Chemical Formula 52]

(43)

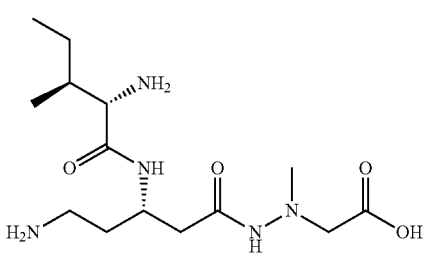

Example compound 38

[Chemical Formula 53]

(44)

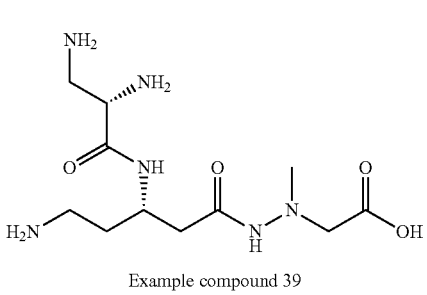

Example compound 39

[Chemical Formula 54]

(45)

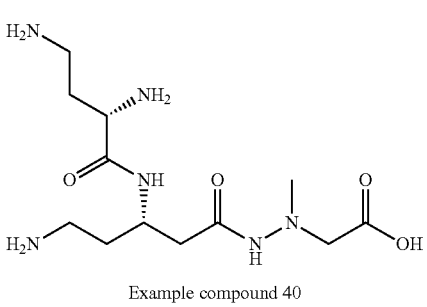

Example compound 40

[Chemical Formula 55]
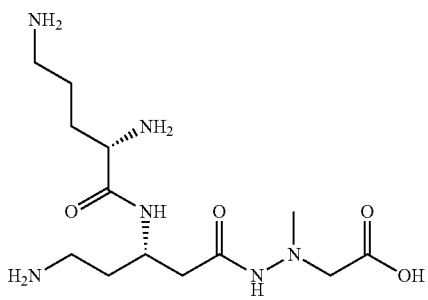
Example compound 41
[Chemical Formula 56]
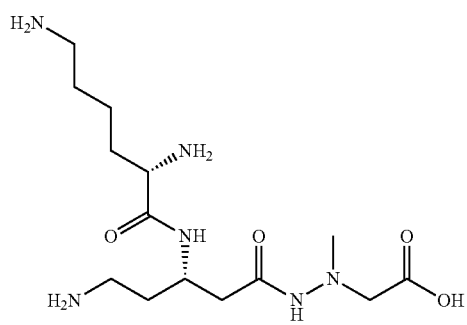
Example compound 42
[Chemical Formula 57]
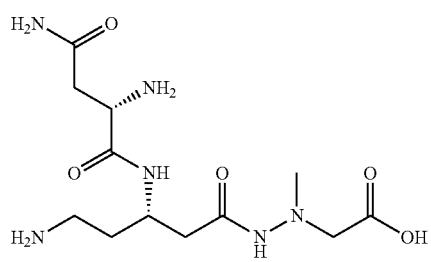
Example compound 43
[Chemical Formula 58]
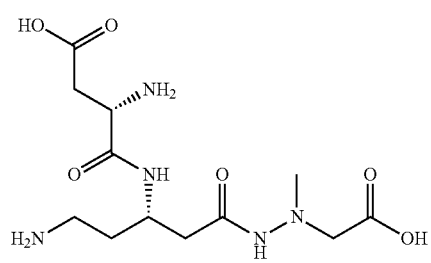
Example compound 44
[Chemical Formula 59]
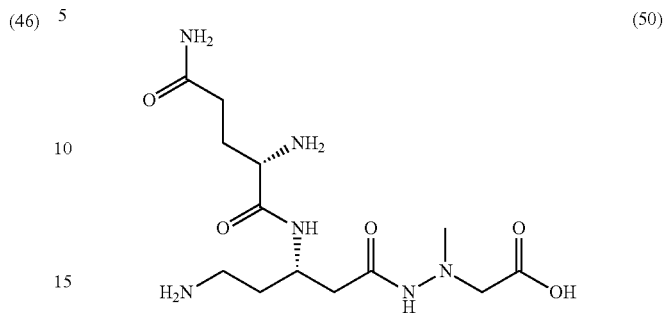
Example compound 45
[Chemical Formula 60]
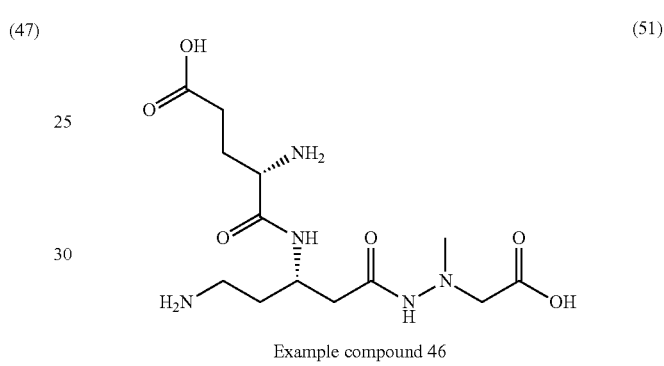
Example compound 46
[Chemical Formula 61]
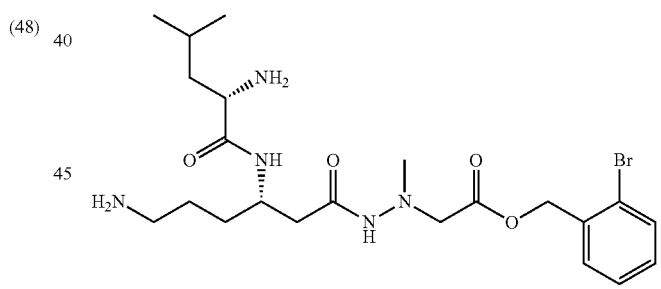
Example compound 47
[Chemical Formula 62]
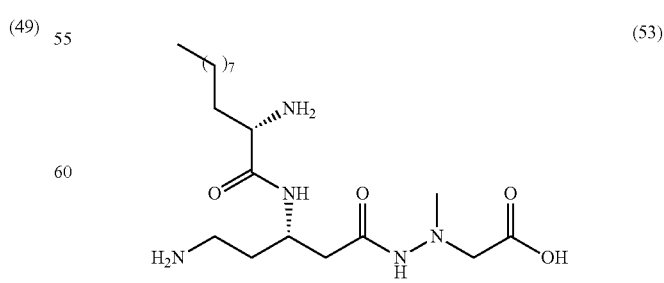
Example compound 48

21
-continued

[Chemical Formula 63]

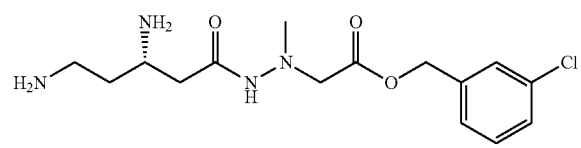

Example compound 49

Synthesis of the compounds of the present invention can be achieved easily by modifications based on the many previous reports of the total synthesis of negamycin. Total synthesis examples from long ago include Y.-F. Wang, T. Izawa, S. Kobayashi and M. Ohno, J. Am. Chem. Soc., 1982, 104, 6465-6466; H. Iida, K. Kasahara and C. Kibayashi, J. Am. Chem. Soc., 1986, 108, 4647-4648, and the like. More recent examples include Davies, S. G. et al., Tetrahedron: Asymmetry 1996, 7, 1919-1922; Williams, R. M. et al., J. Org. Chem. 2002, 67, 6361-6365, and the like.

The present invention also includes salts of the above compounds. Preferred examples of salts are pharmaceutically acceptable salts that can be used as drugs. Salt hydrates and salt anhydrides are also included. Examples include salts of sodium, potassium, magnesium, calcium, aluminum, and other such inorganic bases; salts of methylamine, ethylamine, ethanolamine, and other such organic bases; salts of lysine, ornithine, and other such basic amino acids, and ammonium salts. These salts may be acid addition salts. Concrete examples of such salts include acid addition salts of hydrochloric acid, hydrobromic acid, hydroiodic acid, sulfuric acid, nitric acid, phosphoric acid, and other such mineral acids; formic acid, acetic acid, propionic acid, oxalic acid malonic acid, succinic acid, fumaric acid, maleic acid, lactic acid, malic acid, tartaric acid, citric acid, methanesulfonic acid, ethanesulfonic acid, and other such organic acids; aspartic acid, glutamic acid, and other such acidic amino acids.

The present invention also includes various pharmaceutically acceptable solvates, crystalline polymorphs, and the like of hydrates and the like of the above compounds.

The compounds of the present invention act on the ribosomes in a situation in which a premature stop codon is produced by a nonsense mutation and a specific protein cannot be produced; the ribosomes read through the premature stop codon produced by the nonsense mutation and carry out translation, resulting in the production of a wild-type normal protein. In the present invention, the term wild-type normal protein means a protein consisting of an amino acid sequence encoded by a mutation-free normal wild-type gene. Wild-type normal proteins also include proteins consisting of amino acid sequences substantially identical to the above amino acid sequence. The term substantially identical protein means, for example, a protein having the same function and activity as the protein encoded by the normal wild-type gene that is a protein consisting of an amino acid sequence in which one or multiple amino acids have been deleted, replaced, or added in the amino acid sequence encoded by the normal wild-type gene. Here, one or multiple preferably means one or several, specifically, 1-100, preferably 1-50, more preferably 1-10, and especially 1-5, 4, 3, or 2. Moreover, this substantially identical protein means a protein having sequence identity of 80% or higher, preferably 90% or higher, more preferably 95% or higher, and especially 96, 97, 98, or 99% or higher with the amino acid sequence encoded by the normal wild-type gene when calculated using BLAST or the like (for example, default, i.e. initial settings, parameters) and having the same function and activity as the protein encoded by the normal wild-type gene.

Another separate embodiment of the present invention relates to a pharmaceutical composition containing a compound represented by the following general formula (1) or a salt or solvate of the compound.

[Chemical Formula 64]

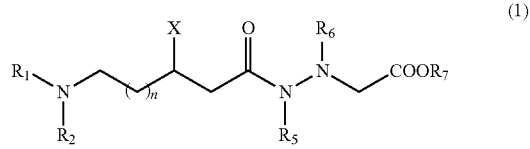

in which
$R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group, $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group, $R_1$ and $R_2$ also may be an amino acid residue introduced via an amide bond formed together with the nitrogen atom to which they are bonded;

X is $N(R_3)(R_4)$, an N-linked amino acid residue, or $C_1$-$C_6$ alkyl group containing an amino group having a substituent, where the substituent of the amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, here, $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_5$ is a $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group;

$R_7$ is hydrogen, a $C_1$-$C_6$ alkyl group, substituted or unsubstituted aralkyl group, or $C_3$-$C_7$ cycloalkyl group, where the substituent of a substituted aralkyl group is a halogen, $C_1$-$C_4$ alkyl group, alkoxy group, hydroxy group, nitro group, amino group, $C_1$-$C_6$ acyl group, or amino group modified by an alkyl group, sulfonic acid group;

n is an integer of 0-3.

3-Epi-5-dehydroxynegamycin which was isolated from nature and known in the past is also included among compounds represented by general formula (1). However, this natural substance could not be anticipated easily since it has weak antimicrobial activity and none of the research conducted in the past found read-through activity. The presence of a natural substance having leucine added by an amide bond to the position 3 amino group was also known, but this natural substance has no antimicrobial activity and was left as a substance of unknown activity. The present inventors discovered that this 3-N-leucyl-3-epi-5-dehydronegamycin also has potent read-through activity and perfected the pharmaceutical composition of the present invention.

One aspect of the present invention is a pharmaceutical composition containing a compound represented by the following general formula (3) or a salt or solvate of the compound.

[Chemical Formula 65]

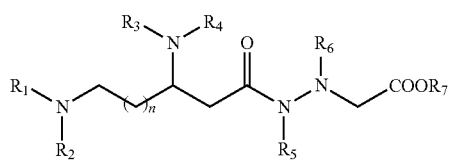

(3)

in which $R_1$, $R_2$, $R_3$, $R_4$, $R_5$, $R_6$, $R_7$, and n are as defined in general formula (1).

One aspect of the present invention is a pharmaceutical composition containing a compound represented by the following general formula (5) or a salt or solvate of the compound.

[Chemical Formula 66]

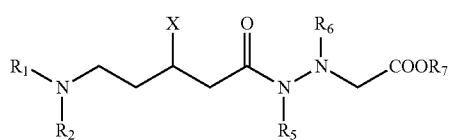

(5)

in which $R_1$, $R_2$, X, $R_3$, $R_4$, $R_5$, $R_6$, and $R_7$ are as defined in general formula (1).

One aspect of the present invention is a pharmaceutical composition containing a compound wherein $R_1$ and $R_2$ in general formula (1), (3), or (5) are an amino acid residue introduced via an amide bond formed together with the nitrogen atom to which they are bonded and this amino acid residue is represented by formula (2) below, or a salt or solvate of the compound.

[Chemical Formula 67]

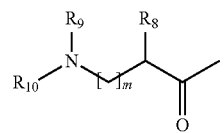

(2)

in which
$R_8$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, where substituents that these substituents can have are a halogen, hydroxyl group, carboxyl group, amino group, or amide group;

$R_9$, $R_{10}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_9$ and $R_{10}$ also may form, together with the nitrogen atom to which they are bonded, a three- to six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group;

m is an integer of 0-4.

One aspect of the present invention is a pharmaceutical composition containing a compound wherein the N-linked amino acid residue of X in general formula (1) or (5) is represented by the following formula (4), or a salt or solvate of the compound.

[Chemical Formula 68]

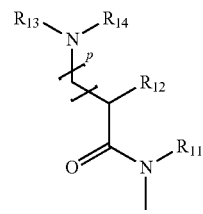

(4)

in which
$R_{11}$ is hydrogen or an optionally substituted $C_1$-$C_6$ alkyl group;

$R_{12}$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, where substituents that these substituents can have are a halogen, hydroxyl group, carboxyl group, amino group, or amide group;

$R_{13}$, $R_{14}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_8$ and $R_9$ also may form, together with the nitrogen atom to which they are bonded, a three- to six-membered heterocycle or heteroaryl bonded via N, may also contain 1-3 additional hetero atoms selected from the group consisting of O, N, and S as ring constituent members (for example, oxazolidine), where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group;

p is an integer of 0-3.

Examples of substituents that the optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group of $R_{12}$ in formula (4) can have are a halogen, hydroxyl group, carboxyl group, amino group, and amide group. Optionally substituted $C_1$-$C_{10}$ alkyl groups may be linear or branched and may form a cyclic structure.

A preferred embodiment of the present invention is a pharmaceutical composition containing a compound, wherein $R_{12}$ is an optionally substituted $C_4$-$C_9$ alkyl group, or a salt or solvate of the compound.

A preferred embodiment of the present invention is a pharmaceutical composition containing a compound, wherein $R_{12}$ is an optionally substituted $C_7$-$C_9$ alkyl group, or a salt or solvate of the compound.

The pharmaceutical composition of the present invention can be used in the treatment or prevention of nonsense mutation-type diseases. Nonsense mutation-type disease means a disease caused by the production of a stop codon midway in a gene (premature stop codon) due to a point mutation, deletion, insertion, or the like on a gene resulting in suppression of the expression of a normally functioning protein. Moreover, nonsense mutation-type disease means a disease caused by inhibition of the expression of a protein in association with degradation of mRNA containing a premature stop codon. Examples of nonsense mutation-type diseases include muscular dystrophy, Duchenne muscular dystrophy, infantile neuronal ceroid lipofuscinosis, multiple sclerosis, Alzheimer's disease, Tay-Sachs disease, neurodegenerative disease, Parkinson's disease, and other such central nervous diseases; rheumatoid arthritis, graft-versus-host disease, and other such autoimmune diseases; arthritis and other such inflammatory diseases; hemophilia, von Willebrand disease, ataxia telangiectasia, β-thalassemia, kidney stones, and other such blood diseases; osteogenesis imperfecta, liver cirrhosis, and other such collagen diseases; Other examples include neurofibromatosis, bullous disease, lysosomal storage disease, Hurler disease, familial hypercholesterolemia, cerebellar ataxia, nodular sclerosis, immunodeficiency, kidney disease, lung disease, cystic fibrosis, familial cholesterolemia, pigmentary retinopathy, amyloidosis, atherosclerosis, gigantism, dwarfism, hypothyroidism, hyperthyroidism, aging, obesity, Niemann-Pick disease, Marfan syndrome, and the like. Cancer is also another example. For example, lung cancer, colorectal cancer, stomach cancer, esophageal cancer, kidney cancer, pancreatic cancer, liver cancer, prostate cancer, breast cancer, uterine cancer, ovarian cancer, skin cancer, brain tumors, and the like are included as cancers in which a nonsense mutation of a p53 gene or another such suppressor gene participates. Among these, it can preferably be used in muscular dystrophy, cystic fibrosis, Hurler disease, and infantile neuronal ceroid lipofuscinosis. The pharmaceutical composition may contain two or more of the above compounds.

The compounds of the present invention can be used as a prodrug. Specifically, the water solubility of the compound decreases and the liposolubility increases when the part represented by —$COOR_7$ is an ester in compounds of the above formulas (1), (3), and (5). Compounds of increased liposolubility promote systemic absorption and become an active form while being absorbed due to esterase present in the digestive tract and the like, increasing enteral absorption, or reach a site at which they are to act within the body and there they are converted into a carboxyl group by esterase present in the organs and tissues and can act at the site reached. As a result, the bioavailability is increased in the end. The compounds of the present invention also include compounds in the form of such prodrugs and also include compounds not in the form of prodrugs.

The route of administration of the pharmaceutical composition of the present invention is not limited, and it can be administered by oral administration, subcutaneous administration, intracutaneous administration, intravenous administration, intramuscular administration, intraperitoneal administration, per nasal administration, intra-oral administration, transmucosal administration, and the like. The dosage form is also not limited. For example, tablets, capsules, powders, granules, pills, liquids, emulsions, suspensions, solutions, tinctures, syrups, extracts, and elixirs can be made for oral administration. As parenteral agents, for example, subcutaneous injections, intravenous injections, intramuscular injections, intraperitoneal injections, and other such injections; percutaneous administration or adhesive skin patches, ointments, or lotions; sublingual agents or oral adhesive patches for intra-oral administration; and aerosols for per nasal administration can be made. For example, a pharmaceutical composition of the present invention can be administered as an injection (for example, an intramuscular injection for direct administration to a muscle) to treat muscular dystrophy. The pharmaceutical composition of the present invention may be in the form of a sustained-release or slow-release agent.

The pharmaceutical composition of the present invention can contain various pharmaceutically acceptable components. Examples include excipients, disintegrating agents, diluents, lubricants, flavorings, colorings, sweeteners, flavoring agents, suspending agents, wetting agents, emulsifiers, dispersing agents, auxiliary agents, preservatives, buffers, binders, stabilizers, coating agents, and the like. A plurality of these may be contained.

The dose of the pharmaceutical composition of the present invention is not limited, but is selected as is appropriate in accordance with the efficacy of the components contained, the dosage form, route of administration, type of disease, weight, age, medical conditions, and other such characteristics of the patient being administered, the judgment of a physician, and the like. For example, it is a range of approximately 0.01 µg to approximately 100 mg, preferably approximately 0.1 µg to approximately 1 mg, per kilogram of the patient's body weight. The dose can be administered from once to divided over several times per day or may be administered intermittently once every several days or every several weeks.

The read-through activity of compounds of the present invention can be tested, for example, by constructing a vector containing (i) a promoter, (ii) a first translation initiation codon and first reporter gene positioned downstream of the above promoter, (iii) a second translation initiation codon and second reporter gene positioned downstream of the above first reporter gene, (iv) a sequence containing a premature stop codon from a causative gene of a nonsense mutation-type disease positioned between the above first reporter gene and second translation initiation codon, and (v) a translation stop codon positioned downstream of the above second reporter gene, introducing this vector into host cells or creating transgenic animals with the vector introduced into animals, and using these host cells or transgenic animals. Specifically, a compound is administered to the host cells or transgenic animals, and the ratio of the expression level of the second reporter gene to the first reporter gene is compared between a case with and a case without addition of the test compound.

The higher the expression level of the second reporter gene is, the higher the read-through activity can be judged to be. In this case, for example, a CMV promoter, β-actin promoter, or the like can be used as the promoter. A β-galactosidase gene, luciferase gene, GFP (green fluorescent protein) gene, CAT (chloramphenicol acetyl transferase) gene, or the like can be used as the first reporter gene and second reporter gene. A sequence containing a stop codon (TAA, TAG, or TGA) in a reading frame may be used as the sequence containing a premature stop codon from the causative gene of a nonsense-type disease. For example, a gene containing a premature stop codon of a dystrophin gene of mdx mice may be used.

EXAMPLES

A. Synthesis of Compounds of the Present Invention

Example 1

Synthesis of Example Compound 2 ((S)-2-(2-(3,6-diaminohexanoyl)-1-methylhydrazinyl)acetic acid)

Example compound 2 was synthesized by the following synthesis scheme. In the scheme, the numbers appended below the structural formulas represent the compound numbers.

mL) solution of Boc-Orn(Boc)-OH (1.00 g, 3.01 mol) at −15° C. and stirred for 10 minutes at the same temperature. The reaction solution was filtered, washed with THF, and a water (1.5 mL) solution of sodium borohydride (171 mg, 4.52 mmol) was added to the mother liquor obtained in an ice-salt bath and stirred for 20 minutes at the same temperature. After extraction by diethyl ether, the organic layer was washed with water and saturated saline and dried by $Na_2SO_4$. After filtration, a colorless oily substance (523 mg) was obtained by distilling off the mother liquor under reduced pressure. This was used in the next reaction without refining.

The residue obtained was then dissolved in dichloromethane (8 mL), and triethylamine (296 µL, 2.14 mmol) and methanesulfonyl chloride (190 µL, 2.46 mmol) were added while cooling by ice and stirred overnight at room temperature. Water was added to the reaction solution while cooling by ice, followed by extraction by chloroform. The organic layer was washed with saturated saline and dried by $Na_2SO_4$. After filtration, the mother liquor was distilled off under reduced pressure, and a white powder was obtained by refining the residue obtained by silica gel chromatography (chloroform: methanol=40:1). (381 mg, 0.319 mmol, three steps, 32%)

[Chemical Formula 69]

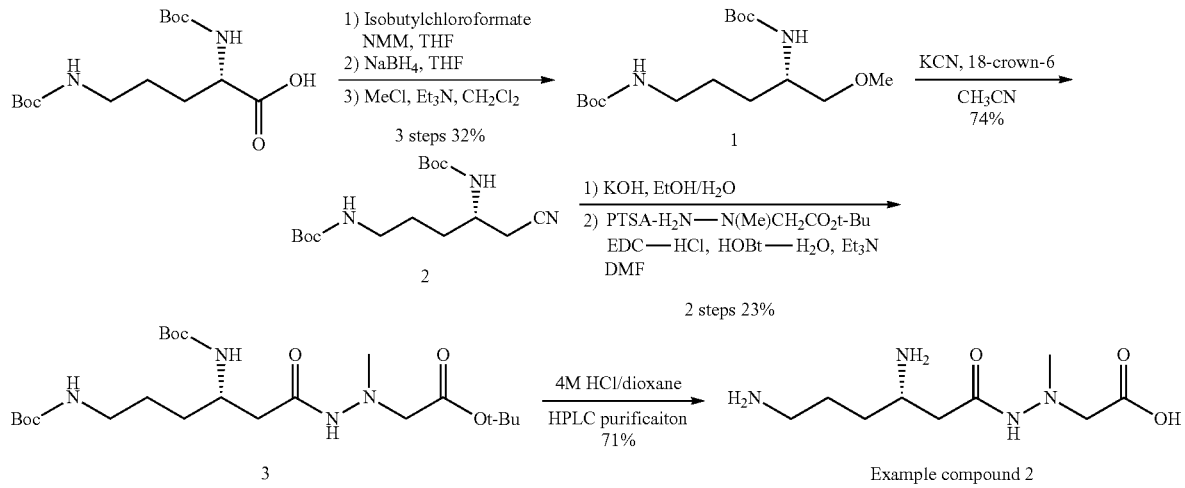

(1) Synthesis of Compound 1 ((S)-2,5-bis(tert-butoxycarbonylamino) pentylmethanesulfonate)

[Chemical Formula 70]

(Compound 1)

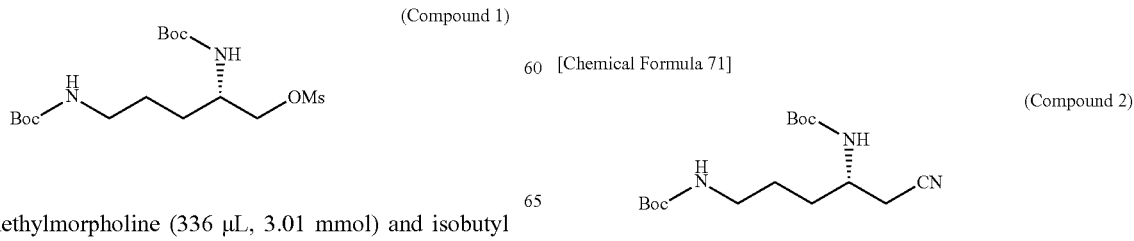

N-methylmorpholine (336 µL, 3.01 mmol) and isobutyl chloroformate (395 µL, 3.01 mmol) were added to a THF (3

$^1$HNMR (300 $MH_z$, $CDCl_3$) δ4.80-4.46 (m, 2H), 4.26 (dd, J=10 and 4.0 Hz, 1H), 4.18 (dd, J=10 and 4.1 Hz, 1H), 3.95-3.76 (m, 1H), 3.23-3.06 (m, 2H), 3.04 (s, 3H), 1.79-1.48 (m, 4H), 1.44 (s, 18H).

(2) Synthesis of Compound 2 ((S)-tert-butyl 5-cyanopentan-1,4-diyldicarbamate)

[Chemical Formula 71]

(Compound 2)

18-crown-6 (239 mg, 0.905 mmol) and potassium cyanide (157 mg, 2.41 mmol) were added to an acetonitrile (6 mL) solution of compound 1 (239 mg, 0.603 mmol) and heat refluxed overnight. After the reaction solution had returned to room temperature, saturated sodium bicarbonate aqueous solution was added while cooling by ice, followed by extraction by ethyl acetate. The organic layer was washed with saturated saline and dried by $Na_2SO_4$. After filtration, the mother liquor was distilled off under reduced pressure, and a white solid was obtained by refining the residue obtained by silica gel chromatography (chloroform:methanol=30:1). (146 mg, 0.446 mmol, 74%)

$^1$HNMR (300 MHz, $CDCl_3$) δ4.87 (brd, 1H), 4.68 (brs, 1H), 3.82 (brs, 1H), 3.23-3.07 (m, 2H), 2.74 (dd, J=17 and 5.4 Hz, 1H), 2.54 (dd, J=17 and 4.2 Hz, 1H), 1.75-1.53 (m, 4H), 1.45 (s, 18H).

(3) Synthesis of Compound 3 ((S)-tert-butyl 2-(2-(3,6-bis(tert-butoxycarbonylamino)hexanoyl)-1-methyl-hydrazinyl)acetate)

[Chemical Formula 72]

(Compound 3)

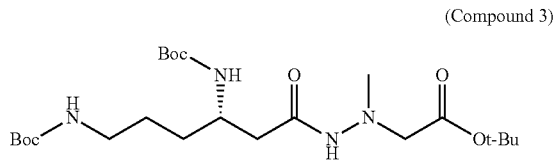

Potassium hydroxide (197 mg, 3.51 mmol) was added to an ethanol:water=2:1 (3 mL) solution of compound 2 (115 mg, 0.351 mmol) and stirred for 4 hours 45 minutes at 80° C. After the reaction solution had returned to room temperature, the solvent was distilled off under reduced pressure. 1 M hydrochloric acid was added while cooling by ice to bring the pH to 1-2, followed by extraction by ethyl acetate. The organic layer was washed with saturated saline and dried by $Na_2SO_4$. After filtration, the mother liquor was distilled off under reduced pressure, the residue obtained was dissolved in DMF (3 mL), and PTSA.$H_2$N—N(Me)$CH_2CO_2$t-Bu (233 mg, 0.702 mmol) and HOBt.$H_2$O (108 mg, 0.702 mmol) were added. Triethylamine (97.3 µL, 0.702 mmol) and EDC.HCl (135 mg, 0.702 mmol) were added sequentially while cooling by ice and stirred for two hours at room temperature. The reaction solution was added to 10% citric acid aqueous solution and extracted by ethyl acetate. The organic layer was washed with saturated sodium bicarbonate aqueous solution, water, and saturated saline and dried by $Na_2SO_4$. After filtration, the mother liquor was distilled off under reduced pressure, and a white solid was obtained by refining the residue obtained by silica gel chromatography (chloroform:methanol=80:1). (40.1 mg, 0.082 mmol, two steps, 23%)

$^1$HNMR (300 MHz, $CDCl_3$) δ7.90 (s) and 7.36 (brd, total 1H), 5.54-5.18 (m, 1H), 4.78-4.66 (m, 1H), 4.00-3.77 (m, 1H), 3.63-3.31 (m, 2H), 3.10-3.01 (m, 2H), 2.90-2.48 (m) and 2.41-2.20 (m, total 5H), 1.98-1.10 (m, 31H).

(4) Synthesis of Example Compound 2

[Chemical Formula 73]

(Example compound 2)

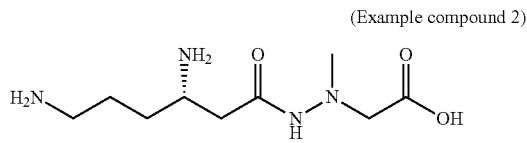

4 M hydrochloric acid/dioxane (2 mL) was added to compound 3 (66.9 mg, 0.137 mmol) while cooling by ice and stirred for one hour at room temperature. The solvent was distilled off under reduced pressure, and the residue obtained was dissolved in water. A colorless oily substance was obtained by refining by high-performance liquid chromatography (solvent, $H_2O$ in 0.1% TFA: $CH_3CN$ in 0.1% TFA. A linear gradient of 0-5% $CH_3CN$ in 0.1% TFA over 40 min. Flow rate 5 mL/min, detected at 222 nm UV). (44.9 mg, 97.5 µmol, 71%)

$^1$HNMR (300 MHz, $D_2O$) δ3.58-3.39 (m, 3H), 2.97-2.77 (m, 2H), 2.60-2.29 (m, 5H), 1.70-1.45 (m, 4H); HRMS(ES+) calcd for $C_9H_{21}N_4O_3$ ($M^+$+H) 233.1614. found 233.1614.

Example 2

Synthesis of Example Compound 5 ((S)-ethyl 2-(2-(3,6-diaminohexanoyl)-1-methylhydrazinyl)acetate)

Example compound 5 was synthesized by the following synthesis scheme.

[Chemical Formula 74]

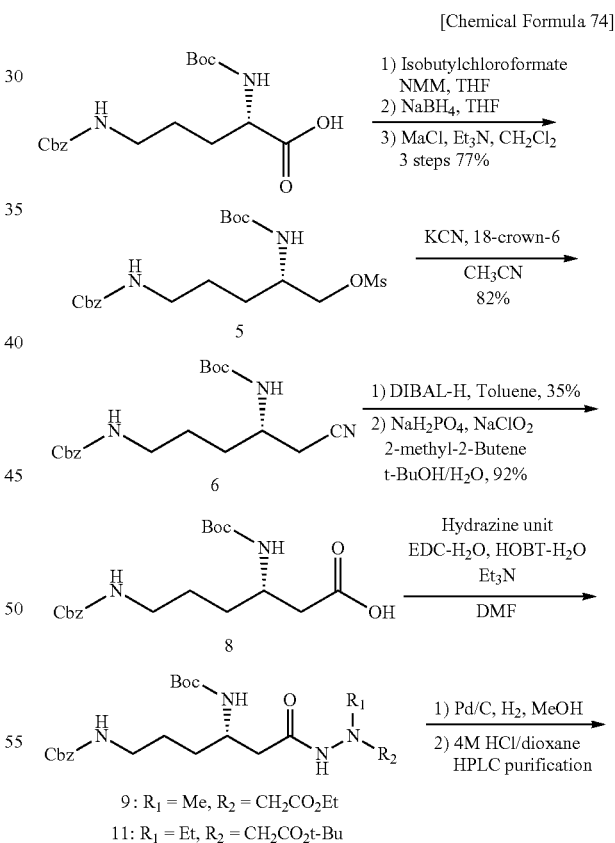

9: $R_1$ = Me, $R_2$ = $CH_2CO_2Et$
11: $R_1$ = Et, $R_2$ = $CH_2CO_2$t-Bu

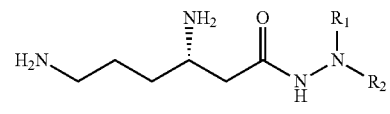

Example compound 5: $R_1$ = Me, $R_2$ = $CH_2CO_2Et$
Example compound 9: $R_1$ = Et, $R_2$ = $CH_2CO_2H$

(1) Synthesis of Compound 5 ((S)-5-(benzyloxycarbonylamino)-2-(tert-butoxycarbonylamino)pentyl-methanesulfonate)

[Chemical Formula 75]

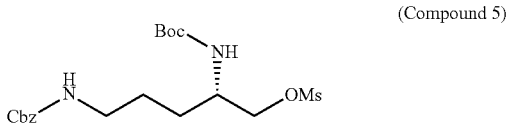

(Compound 5)

N-methylmorpholine (1.97 mL, 15.0 mmol) and isobutyl chloroformate (1.68 mL, 15.0 mmol) were added to a THF (14 mL) solution of Boc-Orn(Cbz)-OH (5.00 g, 13.6 mmol) at −15° C. and stirred for 10 minutes at the same temperature. The reaction solution was filtered and washed with THF. A water (4 mL) solution of sodium borohydride (772 mg, 20.4 mmol) was added to the mother liquor obtained in an ice-salt bath and stirred for 10 minutes at the same temperature. Water was added to the reaction solution while cooling by ice, followed by extraction by ethyl acetate. The organic layer was washed with saturated saline and dried by $Na_2SO_4$. After filtration, a colorless oily substance was obtained by distilling off the mother liquor under reduced pressure. This was used in the next reaction without refining.

The residue obtained was then dissolved in dichloromethane (68 mL), and triethylamine (2.83 mL, 20.4 mmol) and methanesulfonyl chloride (3.14 mL, 40.8 mmol) were added while cooling by ice and stirred for 30 minutes at room temperature. Water was added to the reaction solution while cooling by ice, followed by extraction by chloroform. The organic layer was washed with saturated saline and dried by $Na_2SO_4$. After filtration, the mother liquor was distilled off under reduced pressure, and a white powder was obtained by refining the residue obtained by recrystallization (hexane:ethyl acetate). (4.49 g, 10.4 mmol, three steps, 77%)

[α]25D-17.2° (c0.34, CHCl$_3$); $^1$HNMR (400 MHz, CDCl$_3$) δ7.43-7.30 (m, 5H), 5.20-5.05 (s, 2H), 4.99-4.85 (brs, 1H), 4.80-4.62 (brd, 1H), 4.30-4.08 (M, 2H), 3.94-3.76 (brs, 1H), 3.31-3.14 (m, 2H), 3.02 (s, 3H), 1.79-1.49 (m, 4H), 1.44 (s, 9H); $^{13}$CNMR (100 MHz, CDCl$_3$) δ156.5, 155.4, 136.5, 128.6, 128.2, 80.0, 71.0, 66.7, 49.5, 40.6, 37.3, 28.3, 26.4; HRMS(ES+) calcd for $C_{19}H_{30}N_2O_7SNa$ (M$^+$+NA) 453.1671. found 453.1645.

(2) Synthesis of Compound 6 ((S)-benzyl tert-butyl (5-cyanopentan-1,4-diri)dicarbamate)

[Chemical Formula 76]

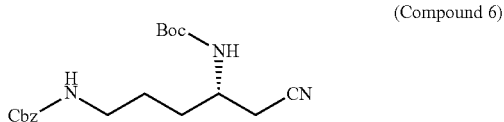

(Compound 6)

18-crown-6 (221 mg, 0.837 mmol) and potassium cyanide (136 mg, 2.09 mmol) were added to an acetonitrile (3.5 mL) solution of compound 5 (300 mg, 0.697 mmol) and heat refluxed for 30 minutes. After the reaction solution had returned to room temperature, saturated sodium bicarbonate aqueous solution was added while cooling by ice, followed by extraction by ethyl acetate. The organic layer was washed with saturated saline and dried by $Na_2SO_4$. After filtration, the mother liquor was distilled off under reduced pressure, and a white solid was obtained by refining the residue obtained by silica gel chromatography (hexane:ethyl acetate=2:1). (206 mg, 0.570 mmol, 82%)

[α] 25D-41.2° (c0.74, CHCl$_3$); $^1$HNMR (400 MHz, CDCl$_3$) δ7.42-7.28 (m, 5H), 5.25-5.12 (m, 1H), 5.08 (s, 2H), 5.06-4.92 (brd, 1H), 3.92-3.69 (brs, 1H), 3.30-3.09 (m, 2H), 2.68 (dd, J=17 and 5.0 Hz, 1H), 2.47 (dd, J=17 and 3.7 Hz, 1H), 1.71-1.49 (m, 4H), 1.43 (s, 9H); $^{13}$CNMR (100 MHz, CDCl$_3$) δ156.5, 155.1, 136.4, 128.5, 128.1, 128.0, 117.3, 80.0, 66.6, 47.0, 40.3, 30.5, 28.2, 26.4, 23.9; HRMS(ES+) calcd for $C_{19}H_{27}N_3O_4Na$ (M$^+$+Na) 384.1899. found 384.1857.

(3) Synthesis of Compound 7 ((S)-6-(benzyloxycarbonylamino)-3-(tert-butoxycarbonylamino)hexanal)

[Chemical Formula 77]

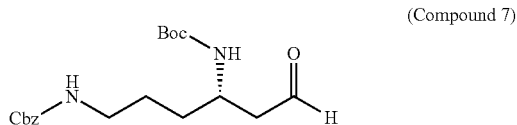

(Compound 7)

Diisobutyl aluminum hydride (1.00 M toluene solution, 47.7 mL, 47.7 mmol) was added dropwise at −78° C. to an anhydrous dichloromethane (80 mL) solution of compound 6 (5.74 g, 15.9 mmol) under an argon atmosphere. The temperature of the reaction solution was raised to −50° C., and it was stirred for 1 hour 20 minutes. Methanol and saturated sodium potassium tartrate aqueous solution were added to the reaction solution at the same temperature, and the temperature was raised to room temperature, followed by extraction by chloroform. The organic layer was washed with saturated saline and dried by $Na_2SO_4$. After filtration, the mother liquor was distilled off under reduced pressure, and a colorless oily substance was obtained by refining the residue obtained by silica gel chromatography (hexane:ethyl acetate=1:1). (1.58 g, 5.52 mmol, 35%)

$^1$HNMR (300 MHz, CDCl$_3$) δ9.74 (s, 1H), 7.40-7.29 (m, 5H), 5.09 (s, 2H), 4.92-4.81 (m, 1H), 4.77-4.63 (m, 1H), 4.10-3.95 (m, 1H), 3.35-3.16 (m, 2H), 2.70-2.55 (m, 2H), 1.73-1.48 (m, 4H), 1.42 (s, 9H).

(4) Synthesis of Compound 8 ((S)-6-(benzyloxycarbonylamino)-3-(tert-butoxycarbonylamino)hexanoic acid)

[Chemical Formula 78]

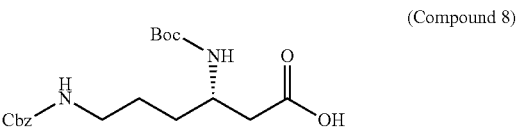

(Compound 8)

2-Methyl-2-butene (2.30 mL, 21.6 mmol) and sodium dihydrogen phosphate (1.69 g, 10.8 mmol) were added to a t-butyl alcohol: water=2:1 (14 mL) solution of compound 7 (1.58 g, 4.33 mmol) and stirred for 10 minutes at room temperature. Sodium chlorite (1.57 g, 17.3 mmol) was then added and stirred for 10 minutes at room temperature. Saturated ammonium chloride aqueous solution was added to the reaction solution while cooling by ice, followed by extraction by chloroform. The organic layer was washed with saturated saline and dried by $Na_2SO_4$. After filtration, the mother liquor was distilled off under reduced pressure, and a colorless oily substance was obtained by refining the residue obtained by silica gel chromatography (chloroform:methanol=50:1). (1.52 g, 4.00 mmol, 92%)

$^1$HNMR (300 MHz, CDCl$_3$) δ7.35-7.32 (m, 5H), 5.09-5.07 (m, 2H), 3.21-3.16 (m, 2H), 2.50-2.48 (m, 2H), 1.58-1.48 (m, 4H), 1.42 (s, 9H); HRMS(ES+) calcd for C$_{19}$H$_{29}$N$_2$O$_6$ (m$^+$+H) 381.2026. found 381.2020.

(5) Synthesis of Compound 9 ((S)-ethyl 2-(2-(6-benzyloxycarbonylamino)-3-(tert-butoxycarbonylamino)hexanoyl)-1-methylhydrazinyl)acetate)

[Chemical Formula 79]

(Compound 9)

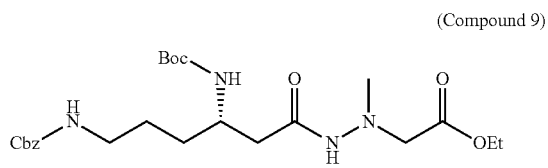

H$_2$N—N(Me)CH$_2$CO$_2$Et (56.4 mg, 0.427 mmol) and HOBt.H$_2$O (65.4 mg, 0.427 mmol) were added to a DMF (2 mL) solution of compound 8 (81.1 mg, 0.213 mmol). Triethylamine (59.2 µL, 0.427 mmol) and EDC.HCl (81.8 mg, 0.427 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline and dried by Na$_2$SO$_4$. After filtration, the mother liquor was distilled off under reduced pressure, and a colorless solid was obtained by refining the residue obtained by silica gel chromatography (chloroform:methanol=80:1) (55.5 mg, 0.112 mmol, 53%)

[α]25D-15.5° (c0.38, CHCl$_3$); $^1$HNMR (400 MHz, CDCl$_3$) δ7.76 (s, 1H), 7.45-7.29 (m, 5H), 5.47-5.18 (m, 1H), 5.08 (s, 2H), 5.05-4.89 (m, 1H), 4.20 (q, J=7.1 Hz, 2H), 4.00-3.78 (m, 1H), 3.73-3.42 (m, 2H), 3.21 (t, J=6.0 Hz, 2H), 2.92-2.49 (m, 4H), 2.40-2.18 (m, 1H), 1.86-1.34 (m, 13H), 1.28 (t, J=7.2 Hz, 3H); $^{13}$CNMR (100 MHz, CDCl$_3$) δ 170.8, 169.7, 156.5, 155.7, 136.7, 128.5, 128.08, 128.05, 79.2, 66.6, 60.9, 57.7, 47.6, 44.1, 40.7, 39.3, 32.0, 28.5, 26.7, 14.0; HRMS(ES+) calcd for C$_{24}$H$_{39}$N$_4$O$_7$ (M$^+$+H) 495.2819. found 495.2816.

(6) Synthesis of Example Compound 5

[Chemical Formula 80]

(Example compound 5)

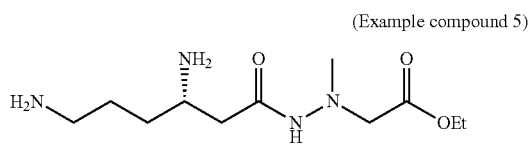

10% Pd/C (4.4 mg) was added to a methanol (1 mL) solution of compound 9 (44.0 mg, 89.0 µmol) under an argon atmosphere, hydrogen substitution was performed, and the solution was stirred for 30 minutes at 50° C. The reaction solution was filtered by Celite, and the solvent was distilled off under reduced pressure. The residue obtained was used in the next reaction without refining. 4 M hydrochloric acid/dioxane (2 mL) was added to the residue while cooling by ice and stirred for one hour at room temperature. The solvent was distilled off under reduced pressure, and the residue obtained was dissolved in water. A colorless oily substance was obtained by refining by high-performance liquid chromatography (solvent, H$_2$O in 0.1% TFA: CH$_3$CN in 0.1% TFA. A linear gradient of 5-10% CH$_3$CN in 0.1% TFA over 40 min. Flow rate 5 mL/min, detected at 222 nm UV). (19.3 mg, 39.6 µmol, two steps, 44%)

$^1$HNMR (300 MHz, D$_2$O) δ 4.10 (q, J=6.9 Hz, 2H), 3.62-3.46 (m, 3H), 3.01-2.86 (m, 1H), 2.62-2.35 (m, 5H), 1.77-1.58 (m, 4H), 1.16 (t, J=6.6 Hz, 3H); HRMS(ES+) calcd for C$_{11}$H$_{25}$N$_4$O$_3$ (M$^+$+H) 261.1927. found 261.1926.

Example 3

Synthesis of Example Compound 9 ((S)-2-(2-(3,6-diaminohexanoyl)-1-ethylhydrazinyl)acetic acid)

(1) Synthesis of Compound 11 ((S)-tert-butyl 2-(2-(6-(benzyloxycarbonylamino)-3-(tert-butoxycarbonylamino)hexanoyl-1-ethylhydrazinyl)acetate

[Chemical Formula 81]

(Compound 11)

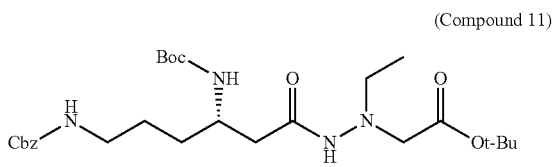

PTSA.H$_2$N—N(Et)CH$_2$CO$_2$t-Bu (167 mg, 0.482 mmol) and HOBt.H$_2$O (73.9 mg, 0.482 mmol) were added to a DMF (3 mL) solution of compound 8 (91.7 mg, 0.241 mmol) synthesized in Example 2. Triethylamine (66.8 µL, 0.482 mmol) and EDC.HCl (92.4 mg, 0.482 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline and dried by Na$_2$SO$_4$. After filtration, the mother liquor was distilled off under reduced pressure, and a colorless solid was obtained by refining the residue obtained by silica gel chromatography (chloroform:methanol=60:1). (71.7 mg, 0.134 mmol, 55%)

[α]25D-6.31° (c0.52, CHCl$_3$); $^1$HNMR (400 MHz, CDCl$_2$) δ 7.73 (s) and 7.15 (d, J=26 Hz, total 1H), 7.42-7.28 (m, 5H), 5.59-5.24 (m, 1H), 5.09 (s, 2H), 5.05-4.91 (brs, 1H), 3.98-3.78 (m, 1H), 3.69-3.38 (m, 2H), 3.30-3.13 (m, 2H), 3.07-2.78 (m, 2H), 2.74-2.21 (m, 2H), 1.70-1.34 (m, 22H), 1.08 (t, J=7.1 Hz, 3H); $^{13}$CNMR (100 MHz, CDCl$_3$) δ 170.5, 169.4, 156.5, 155.7, 136.7, 128.4, 128.06, 128.03, 82.4, 79.3, 66.5, 57.3, 50.4, 47.5, 40.8, 36.4, 32.0, 28.4, 28.2, 26.6, 12.7; HRMS(ES+) calcd for C$_{27}$H$_{45}$N$_4$O$_7$ (M$^+$+H) 537.3288. found 537.3303.

(2) Synthesis of Example Compound 9

[Chemical Formula 82]

(Example compound 9)

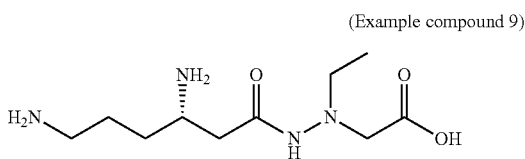

10% Pd/C (5.5 mg) was added to a methanol (2 mL) solution of compound 11 (55.8 mg, 0.104 mmol) under an argon atmosphere, hydrogen substitution was performed, and the solution was stirred for 30 minutes at 50° C. The reaction solution was filtered by Celite, and the solvent was distilled off under reduced pressure. The residue obtained was used in the next reaction without refining. 4 M hydrochloric acid/dioxane (2 mL) was added to the residue while cooling by ice and stirred for one hour at room temperature. The solvent was distilled off under reduced pressure and the residue obtained was dissolved in water. A colorless oily substance was obtained by refining by high-performance liquid chromatography (solvent, $H_2O$ in 0.1% TFA: $CH_3CN$ in 0.1% TFA. A linear gradient of 10-20% $CH_3CN$ in 0.1% TFA over 40 min. Flow rate 5 mL/min, detected at 222 nm UV). (26.7 mg, 56.2 μmol, two steps, 54%)

$^1$HNMR (300 MHz, CDCl$_3$) δ 3.65-3.52 (m, 3H), 3.03-2.80 (m, 4H), 2.55 (dd, J=17 and 5.4 Hz, 2H), 1.74-1.57 (m, 4H), 0.97 (t, J=7.2 Hz, 3H); HRMS(ES+) calcd for $C_{10}H_{23}N_4O_3$ (M$^+$+H) 247.1770. found 247.1777.

Example 4

Synthesis of Example Compound 7 (2-(2-((S)-6-amino-3-((S)-2-amino-4-methylpentanamide)hexanoyl)-1-methylhydrazinyl)acetic acid)

Example compound 7 was synthesized by the following synthesis scheme.

(1) Synthesis of Compound 13 ((S)-benzyl 2-(2-(6-(benzyloxycarbonylamino)-3-(tert-butoxycarbonylamino)hexanoyl)-1-methylhydrazinyl)acetate)

[Chemical Formula 84]

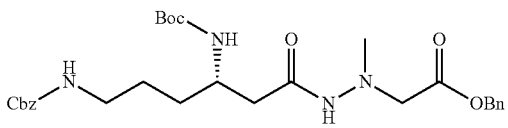

(Compound 13)

$H_2N$—$N(Me)CH_2CO_2Bn$ (163 mg, 0.842 mmol) and HOBt.H$_2$O (129 mg, 0.842 mmol) were added to a DMF (2 mL) solution of compound 8 (160 mg, 0.421 mmol). Triethylamine (117 μL, 0.842 mmol) and EDC.HCl (161 mg, 0.842 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline and dried by Na$_2$SO$_4$. After filtration, the mother liquor was distilled off under reduced pressure, and a white solid was obtained by refining the residue obtained by silica gel chromatography (chloroform:methanol=80:1). (139 mg, 0.250 mmol, 59%)

[α]25D-6.49° (c0.75, CHCl$_3$); $^1$HNMR (400 MHz, CDCl$_2$) δ 7.75 (s) and 7.42-7.19 (m, total, 11H), 5.48-4.76 (m, 6H), 4.00-3.77 (m, 1H), 3.77-3.45 (m, 2H), 3.30-3.05 (m,

[Chemical Formula 83]

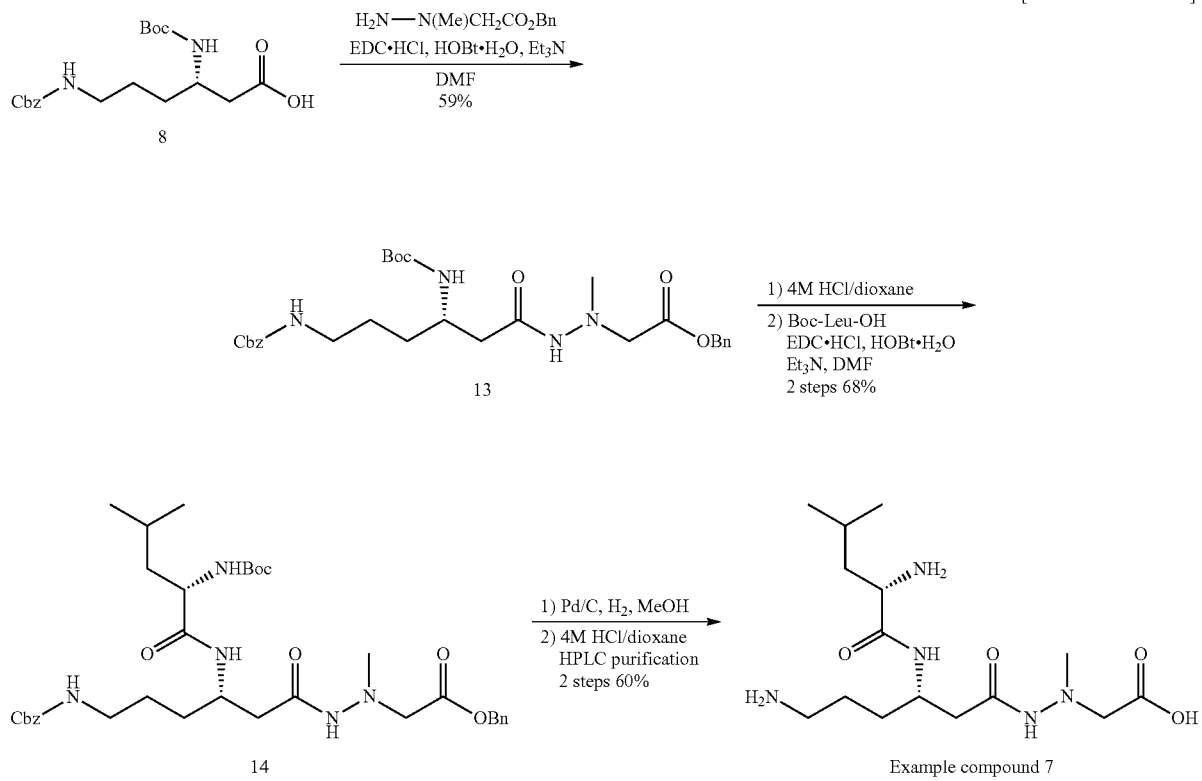

2H), 2.90-2.48 (m, 4H), 2.40-2.10 (m, 1H), 1.92-1.46 (m, 4H), 1.40 (s, 9H); $^{13}$CNMR (100 MHz, CDCl$_2$) δ 170.6, 169.3, 156.5, 155.6, 136.7, 135.1, 128.71, 128.67, 128.62, 128.51, 128.43, 128.06, 79.2, 66.6, 58.9, 57.7, 47.5, 44.1, 40.7, 39.3, 32.0, 28.4, 26.6; HRMS(ES+) calcd for C$_{29}$H$_{41}$N$_4$O$_7$ (M$^+$+H) 557.2975. found 557.2985.

(2) Synthesis of Compound 14 ((7S,10S)-benzyl 7-(3-(benzyloxycarbonylamino)propyl)-10-isobutyl-3,14,14-trimethyl-5,9,12-trioxo-13-oxa-3,4,8,11-tetraazapentadecan-1-oate)

[Chemical Formula 85]

(Compound 14)

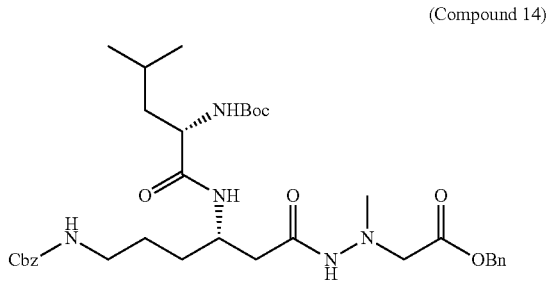

4 M hydrochloric acid/dioxane (3 mL) was added to compound 13 (66.2 mg, 0.119 mmol) while cooling by ice and stirred for 30 minutes at room temperature. The solvent was distilled off under reduced pressure, and the residue obtained was used in the next reaction without refining. The residue was dissolved in DMF (2 mL), and Boc-Leu-OH (35.6 mg, 0.143 mmol) and HOBt.H$_2$O (20.0 mg, 0.131 mmol) were added. Triethylamine (18.2 μL, 0.131 mmol) and EDCHCl (27.4 mg, 0.131 mmol) were added sequentially and stirred overnight at room temperature. The reaction solution was added to 10% citric acid aqueous solution and extracted by ethyl acetate. The organic layer was washed with saturated sodium bicarbonate aqueous solution, water, and saturated saline and dried by Na$_2$SO$_4$. After filtration, the mother liquor was distilled off under reduced pressure, and a colorless solid was obtained by refining the residue obtained by silica gel chromatography (chloroform:methanol=80:1). (54.0 mg, 0.081 mmol, two steps 68%)

[α]25D-21.5° (c0.67, CHCl$_3$); $^1$HNMR (400 MHz, CDCl$_3$) δ 7.79 (s) and 7.45-7.29 (m, total 11H), 7.03 (brs, 1H), 5.25-5.00 (m, 5H), 4.94 (brs, 1H), 4.35-4.10 (m, 1H), 4.10-3.93 (brs, 1H), 3.77-3.46 (m, 2H), 3.28-3.08 (m, 2H), 2.93-2.43 (m, 4H), 2.37-2.16 (m, 1H), 1.98-1.20 (m, 16H), 1.03-0.75 (m, 6H); $^{13}$CNMR (100 MHz, CDCl$_3$) δ 172.4, 170.6, 169.0, 156.58, 156.54, 136.72, 135.16, 128.73, 128.66, 128.52, 128.48, 128.45, 128.04, 80.0, 66.7, 66.6, 57.8, 53.6, 46.1, 44.2, 41.4, 40.7, 40.6, 38.8, 31.4, 28.3, 26.4, 23.9, 22.0; HRMS(ES+) calcd for C$_{35}$H$_{52}$N$_5$O$_8$ (M$^+$+H) 670.3816. found 670.3808.

(3) Synthesis of Example Compound 7

[Chemical Formula 86]

(Example compound 7)

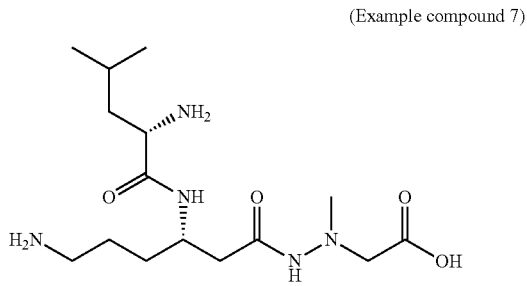

10% Pd/C (3.1 mg) was added to a methanol (2 mL) solution of compound 14 (31.3 mg, 46.8 μmol) under an argon atmosphere, hydrogen substitution was performed, and the solution was stirred for 45 minutes at 50° C. The reaction solution was filtered by Celite, and the solvent was distilled off under reduced pressure. The residue obtained was used in the next reaction without refining. 4 M hydrochloric acid/dioxane (2 mL) was added to the residue while cooling by ice and stirred for 10 minutes at room temperature. The solvent was distilled off under reduced pressure, and the residue obtained was dissolved in water. A white, cottony substance was obtained by refining by high-performance liquid chromatography (solvent, H$_2$O in 0.1% TFA: CH$_3$CN in 0.1% TFA. A linear gradient of 10-15% CH$_3$CN in 0.1% TFA over 40 min. Flow rate 5 mL/min, detected at 222 nm UV). (16.1 mg, 28.0 μmol, two steps, 60%)

$^1$HNMR (300 MHz, D$_2$O) δ 4.23-4.00 (m, 1H), 3.92-3.74 (m, 1H), 3.50 (s, 2H), 2.89 (t, J=6.3 Hz, 2H), 2.56 (s, 3H), 2.36 (dd, J=15 and 5.4 Hz, 1H), 2.21 (dd, J=15 and 9 Hz, 1H), 1.72-1.35 (m, 7H), 0.83 (dd, J=4.2 Hz, 6H); HRMS(ES+) calcd for C$_{15}$H$_{32}$N$_5$O$_4$ (M$^+$+H) 346.2454. found 346.2452.

Example 5

Synthesis of Example Compound 3 ((S)-2-(2-(3,5-diaminopentanoyl)-1-methylhydrazinyl)acetic acid)

Example compound 3 was synthesized by the following synthesis scheme.

[Chemical Formula 87]

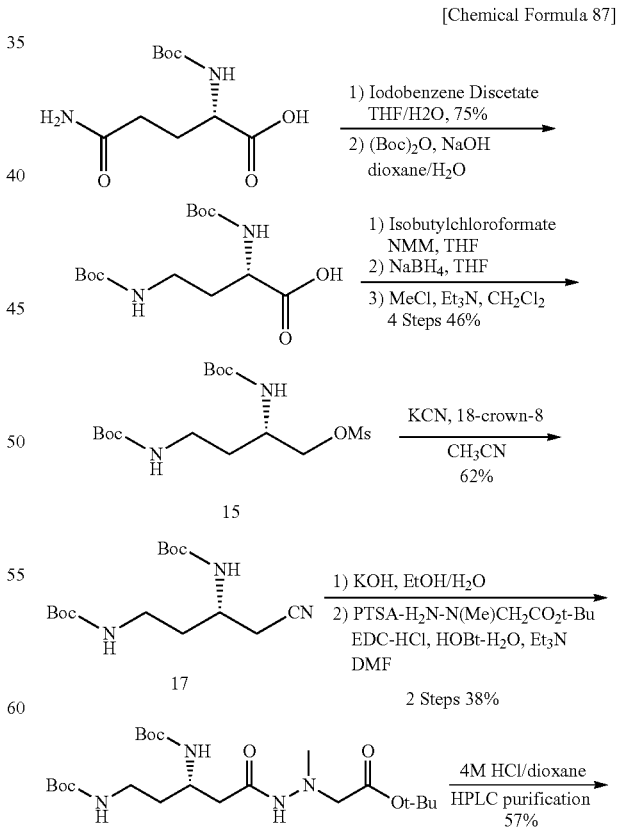

-continued

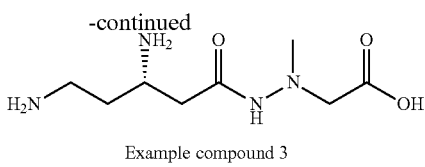

Example compound 3

(1) Synthesis of Compound 16 ((S)-2,4-bis(tert-butoxycarbonylamino) butylmethanesulfonate)

Water (36 mL) was added to a THF (145 mL) solution of Boc-Gln-OH (15.0 g, 60.9 mmol), and iodobenzene diacetate (23.5 g, 73.1 mmol) was added while cooling by ice and stirred for 4 hours 30 minutes at room temperature. The reaction solution was distilled under reduced pressure, and water was added to the residue obtained, followed by extraction by ethyl acetate. The water layer was distilled off under reduced pressure, and the residue obtained was washed multiple times with cold chloroform, and a white powder (10.0 g) was obtained by drying. This was used in the next reaction without refining.

Sodium hydroxide (2.02 g, 50.4 mmol) and (Boc)$_2$O (12.0 g, 55.0 mmol) were added while cooling by ice to a dioxane:water=2:1 (225 mL) solution of the above powder (10.0 g, 45.8 mmol) and stirred for one hour at room temperature. The reaction solution was distilled off under reduced pressure, and 1 M hydrochloric acid was added while cooling by ice to the residue obtained to bring the pH to 1-2, followed by extraction by ethyl acetate. The organic layer was washed with saturated saline and dried by Na$_2$SO$_4$. After filtration, a yellow oily substance was obtained by distilling off the mother liquor under reduced pressure. This was used in the next reaction without refining.

The residue was dissolved in THF (90 mL), and N-methylmorpholine (5.63 mL, 50.4 mmol) and isobutyl chloroformate (6.62 mL, 50.4 mmol) were added at −15° C. and stirred for five minutes at the same temperature. The reaction solution was filtered, washed with THF, and a water (15 mL) solution of sodium borohydride (2.60 g, 68.7 mmol) was added in an ice-salt bath to the mother liquor obtained and stirred for five minutes at the same temperature. 1 M hydrochloric acid was added to the reaction solution while cooling by ice, followed by extraction by ethyl acetate. The organic layer was washed with saturated saline and dried by Na$_2$SO$_4$. After filtration, a colorless oily substance was obtained by distilling off the mother liquor under reduced pressure. This was used in the next reaction without refining.

Triethylamine (9.52 mL, 68.7 mmol) and methanesulfonyl chloride (10.6 mL, 137 mmol) were added to a dichloromethane (230 mL) solution of the residue and stirred overnight at room temperature. Water was added to the reaction solution while cooling by ice, followed by extracted by chloroform. The organic layer was washed with saturated saline and dried by Na$_2$SO$_4$. After filtration, the mother liquor was distilled off under reduced pressure, and a colorless oily substance was obtained by refining the residue obtained by silica gel chromatography (hexane:ethyl acetate=2:1). (7.97 g, 20.9 mmol, four steps, 46%)

$[\alpha]25D$-38.1° (c1.97, CHCl$_3$); $^1$HNMR (400 MHz, CDCl$_3$) δ 5.21-5.03 (brs, 1H), 5.03-4.78 (brd, 1H), 4.30 (dd, J=10 and 3.5 Hz, 1H), 4.23 (dd, J=10 and 4.4 Hz, 1H), 4.01-3.88 (m, 1H), 3.49-3.27 (brs, 1H), 3.12-2.94 (m, 4H), 1.87-1.55 (m, 2H), 1.44 (s, 18H); $^{13}$CNMR (100 MHz, CDCl$_3$) δ 156.0, 155.7, 80.1, 79.4, 71.4, 47.3, 37.3, 36.9, 31.9, 28.4, 28.3; HRMS(ES+) calcd for C$_{15}$H$_{30}$N$_2$O$_7$SNa (M$^+$+Na) 405.1671. found 405.1671.

(2) Synthesis of Compound 17 ((S)-tert-butyl 4-cyanobutane-1,3-diyldicarbamate)

[Chemical Formula 88]

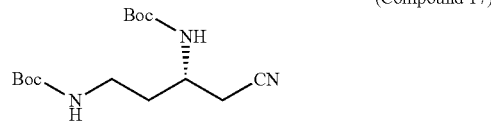

(Compound 17)

18-Crown-6 (2.76 g, 10.4 mmol) and potassium cyanide (2.72 g, 41.7 mmol) were added to an acetonitrile (105 mL) solution of compound 16 (7.97 g, 20.9 mmol) and stirred overnight at 40° C. After the reaction solution had returned to room temperature, saturated sodium bicarbonate aqueous solution was added while cooling by ice, followed by extraction by ethyl acetate. The organic layer was washed with saturated saline and dried by Na$_2$SO$_4$. After filtration, the mother liquor was distilled off under reduced pressure, and a white solid was obtained by refining the residue obtained by silica gel chromatography (hexane:ethyl acetate=2:1). (4.08 g, 13.0 mmol, 62%)

$[\alpha]25D$-64.1° (c1.14, CHCl$_3$); $^1$HNMR (400 MHz, CDCl$_3$) δ 5.03-4.72 (m, 2H), 4.00-3.83 (m, 1H), 3.48-3.26 (m, 1H), 3.16-2.97 (m, 1H), 2.74 (dd, J=17 and 5.4 Hz, 1H), 2.62 (dd, J=17 and 4.6 Hz, 1H), 1.90-1.67 (m, 2H), 1.45 (s, 9H), 1.44 (s, 9H); $^{13}$CNMR (100 MHz, CDCl$_3$) δ 156.0, 155.3, 117.2, 80.4, 79.6, 45.0, 36.9, 34.3, 28.4, 28.3, 23.9; HRMS(ES+) calcd for C$_{15}$H$_{27}$N$_3$O$_4$Na (M$^+$+Na) 336.1899. found 336.1896.

(3) Synthesis of Compound 18 ((S)-tert-butyl 2-(2-(3,5-bis(tert-butoxycarbonylamino)pentanoyl)-1-methylhydrazinyl)acetate)

[Chemical Formula 89]

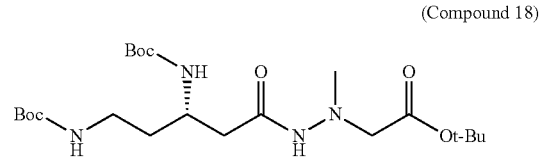

(Compound 18)

Potassium hydroxide (162 mg, 2.88 mmol) was added to an ethanol:water=2:1 (3 mL) solution of compound 17 (90.2 mg, 0.288 mmol) and stirred for 7 hours 30 minutes at 80° C. After the reaction solution had returned to room temperature, the solvent was distilled off under reduced pressure. 1 M hydrochloric acid was added while cooling by ice to bring the pH to 1-2, followed by extraction by ethyl acetate. The organic layer was washed with saturated saline and dried by Na$_2$SO$_4$. After filtration, the mother liquor was distilled off under reduced pressure. The residue obtained was dissolved in DMF (2 mL), and PTSA.H$_2$N—N(Me)CH$_2$CO$_2$t-Bu (191 mg, 0.576 mmol) and HOBt.H$_2$O (88.2 mg, 0.576 mmol) were added. Triethylamine (79.8 μL, 0.576 mmol) and EDC.HCl (110 mg, 0.576 mmol) were added sequentially while cooling by ice and stirred overnight at room temperature.

The reaction solution was added to 10% citric acid aqueous solution and extracted by ethyl acetate. The organic layer was washed with saturated sodium bicarbonate aqueous solution, water, and saturated saline and dried by $Na_2SO_4$. After filtration, the mother liquor was distilled off under reduced pressure, and a white solid was obtained by refining the residue obtained by silica gel chromatography (chloroform:methanol=100:1). (51.3 mg, 0.108 mmol, two steps 38%)

$[α]25D-40.1°$ (c0.52, $CHCl_3$); $^1$HNMR (400 MHz, $CDCl_3$) δ 7.94 (s) and 7.38 (brd, total 1H), 5.83-5.49 (m, 1H), 5.49-5.11 (m, 1H), 4.15-3.80 (m, 1H), 3.69-3.46 (m, 2H), 3.46-3.20 (m, 1H), 3.05-2.81 (m, 1H), 2.81-2.48 (m, 4H), 2.48-2.18 (m, 1H), 1.75-1.18 (m, 29H); $^{13}$CNMR (100 MHz, $CDCl_3$) δ 174.7, 170.2, 169.1, 156.1, 82.4, 79.3, 79.0, 58.2, 45.1, 43.9, 38.9, 37.1, 35.2, 28.44, 28.36, 28.2; HRMS(ES+) calcd for $C_{22}H_{42}N_4O_7Na$ ($M^++Na$) 497.2951. found 497.2959.

(4) Synthesis of Example Compound 3

[Chemical Formula 90]

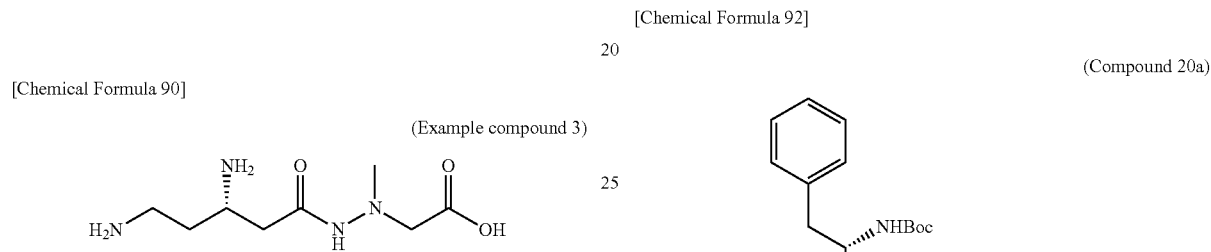

(Example compound 3)

4 M hydrochloric acid/dioxane (2 mL) was added while cooling by ice to compound 18 (29.3 mg, 61.9 μmol) and stirred for one hour at room temperature. The solvent was distilled off under reduced pressure, and the residue obtained was dissolved in water. A colorless oily substance was obtained by refining by high-performance liquid chromatography (solvent, $H_2O$ in 0.1% TFA: $CH_3CN$ in 0.1% TFA. A linear gradient of 0-5% $CH_3CN$ in 0.1% TFA over 40 min. Flow rate 5 mL/min, detected at 222 nm UV). (14.6 mg, 35.3 μmol, 57%)

$^1$HNMR (300 MHz, $D_2O$) δ 3.60-3.50 (m, 1H), 3.47 (s, 2H), 2.93 (t, J=8.8 Hz, 2H), 2.51-2.34 (m, 5H), 1.99-1.79 (m, 2H); HRMS(ES+) calcd for $C_8H_{19}N_4O_3$ ($M^++H$) 219.1457. found 219.1455.

Example 6

Synthesis of Example Compounds 14-18

Example compounds 14-18 were synthesized by the following synthesis scheme. Furthermore, in the scheme, the numbers appended below the structural formulas represent the compound numbers.

[Chemical Formula 91]

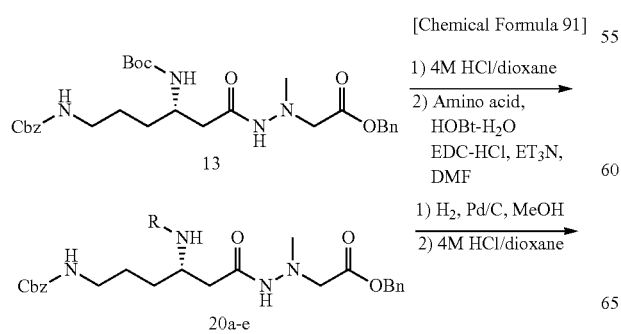

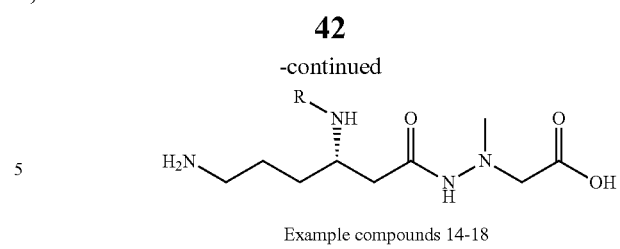

Example compounds 14-18

(A) Compounds 20a-20e (1) Synthesis of Compound 20a

[Chemical Formula 92]

(Compound 20a)

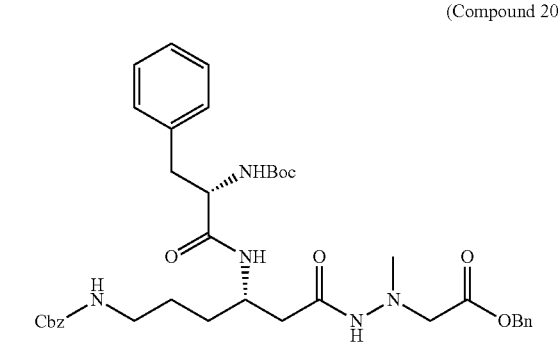

Compound 20a was synthesized by the same method as compound 14 using compound 13 (82.9 mg, 0.149 mmol) (white solid, 92.5 mg, 0.132 mmol, two steps 88%).

HRMS(ES+) calcd for $C_{38}H_{50}N_5O_8$ ($M^++H$) 704.3659 found 704.3652.

(2) Synthesis of Compound 20b

[Chemical Formula 93]

(Compound 20b)

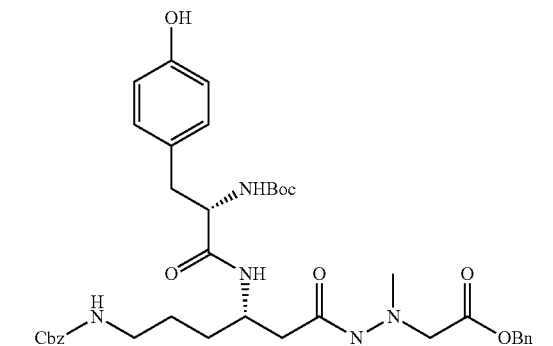

Compound 20b was synthesized by the same method as compound 14 using compound 13 (61.2 mg, 0.110 mmol) (colorless solid, 39.3 mg, 54.6 μmol, two steps 50%).

HRMS(ES+) calcd for $C_{38}H_{50}N_5O_9$ (M$^+$+H) 720.3609. found 720.3595.

(3) Synthesis of Compound 20c

[Chemical Formula 94]

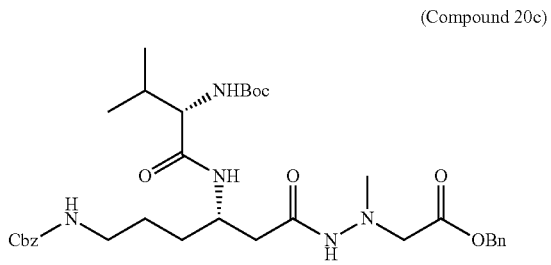

(Compound 20c)

Compound 20c was synthesized by the same method as compound 14 using 13 (71.7 mg, 0.129 mmol) (white solid, 77.8 mg, 0.119 mmol, two steps, 92%).
HRMS(ES+) calcd for $C_{34}H_{49}N_5O_8Na$ (M$^+$+Na) 678.3479. found 678.3481.

(4) Synthesis of Compound 20d

[Chemical Formula 95]

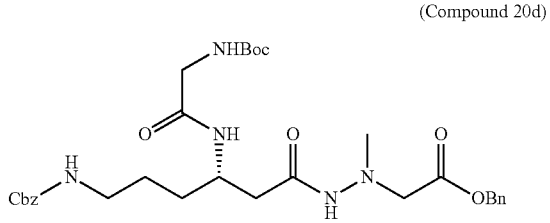

(Compound 20d)

Compound 20d was synthesized by the same method as compound 14 using compound 13 (52.0 mg, 93.5 μmol) (colorless solid, 51.7 mg, 84.3 μmol, two steps 90%).
HRMS(ES+) calcd for $C_{31}H_{44}N_5O_8$ (M$^+$+H) 614.3190. found 614.3175.

(5) Synthesis of Compound 20e

[Chemical Formula 96]

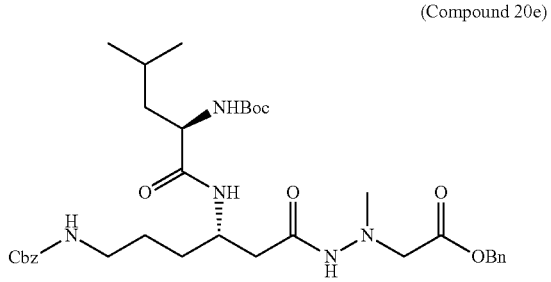

(Compound 20e)

Compound 20e was synthesized by the same method as compound 14 using compound 13 (79.7 mg, 0.143 mmol) (white solid, 90.8 mg, 0.136 mmol, two steps 95%).
HRMS(ES+) calcd for $C_{35}H_{51}N_5O_8Na$ (M$^+$+Na) 692.3635. found 692.3638.

(B) Example Compounds 14-18
(1) Synthesis of Example Compound 14

[Chemical Formula 97]

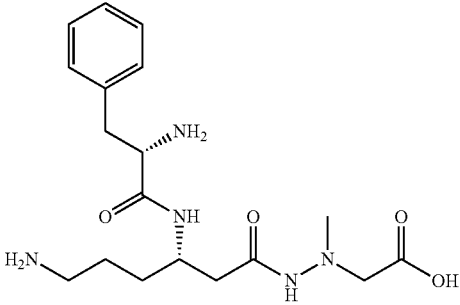

(Example compound 14)

Synthesized by the same method as example compound 7 using compound 20a (43.7 mg, 62.1 μmol) (colorless solid, 11.2 mg, 18.4 μmol, two steps, 30%).
HRMS(ES+) calcd for $C_{18}H_{30}N_5O_4$ (M$^+$+H) 380.2298. found 380.2290.

(2) Synthesis of Example Compound 15

[Chemical Formula 98]

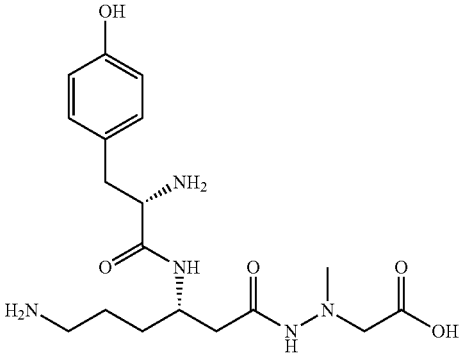

(Example compound 15)

Synthesized by the same method as example compound 7 using compound 20b (27.8 mg, 38.6 μmol) (colorless solid, 8.25 mg, 13.2 μmol, two steps, 34%).
HRMS(ES+) calcd for $C_{18}H_{30}N_5O_5$ (M$^+$+H) 396.2247. found 396.2258.

(3) Synthesis of Example Compound 16

[Chemical Formula 99]

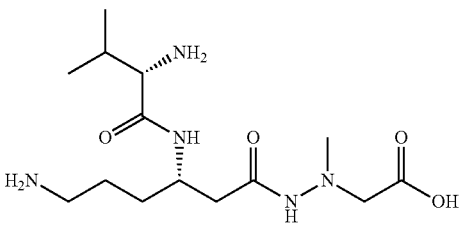

(Example compound 16)

Synthesized by the same method as example compound 7 using compound 20c (40.4 mg, 61.6 μmol) (colorless solid, 11.2 mg, 20.0 μmol, two steps, 33%).

HRMS(ES+) calcd for $C_{14}H_{30}N_5O_4$ (M$^+$+H) 332.2298. found 332.2286.

(4) Synthesis of Example Compound 17

[Chemical Formula 100]

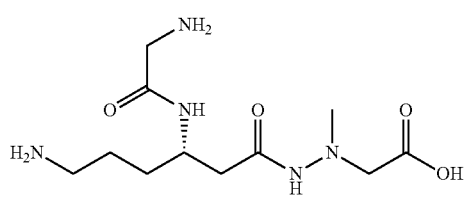

(Example compound 17)

Synthesized by the same method as example compound 7 using compound 20d (30.8 mg, 50.2 μmol) (colorless solid, 12.3 mg, 23.8 μmol, two steps, 47%).
HRMS(ES+) calcd for $C_{11}H_{24}N_5O_4$ (M$^+$+H) 290.1828. found 290.1829.

(5) Synthesis of Example Compound 18

[Chemical Formula 101]

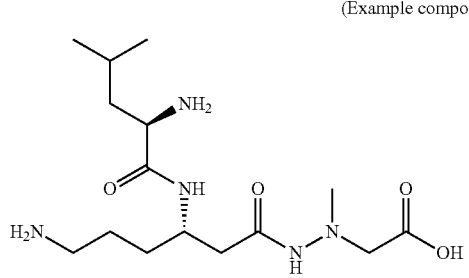

(Example compound 18)

Synthesized by the same method as example compound 7 using compound 20e (43.1 mg, 64.4 μmol) (colorless solid, 17.2 mg, 30.0 μmol, two steps, 47%).
HRMS(ES+) calcd for $C_{15}H_{32}N_5O_4$ (M$^+$+H) 346.2454. found 346.2459.

Example 7

Synthesis of Example Compounds 19-20

Example compounds 19-20 were synthesized by the following synthesis scheme. In the scheme, the numbers appended below the structural formulas represent the compound numbers.

[Chemical Formula 102]

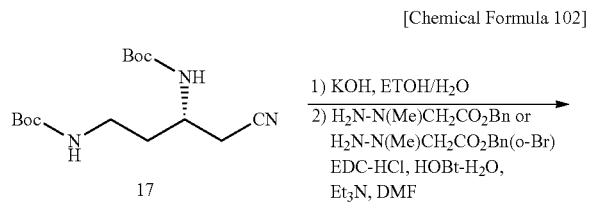

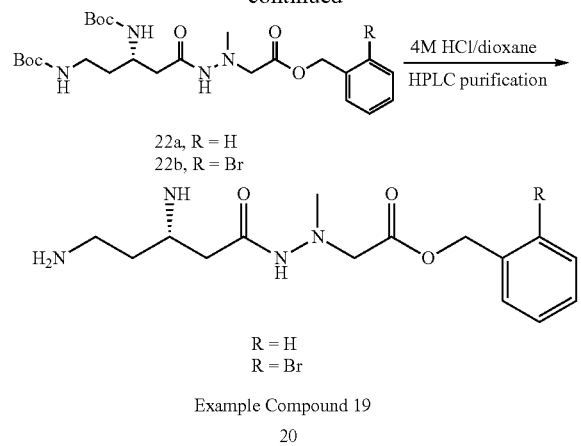

Example Compound 19

(A) Compounds 22a-22b (1) Synthesis of Compound 22a

[Chemical Formula 103]

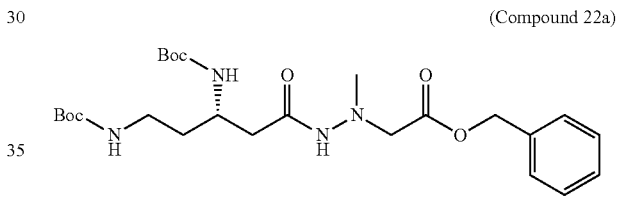

(Compound 22a)

Potassium hydroxide (1.85 g, 32.9 mmol) was added to an ethanol:water=2:1 (16 mL) solution of compound 17 (1.03 g, 3.29 mmol) and stirred for five hours at 80° C. After the reaction solution had returned to room temperature, the solvent was distilled off under reduced pressure. 1 M hydrochloric acid was added while cooling by ice to bring the pH to 1-2, followed by extraction by ethyl acetate. The organic layer was washed with saturated saline and dried by $Na_2SO_4$. After filtration, the mother liquor was distilled off under reduced pressure, and the residue obtained was dissolved in DMF (16 mL), and $H_2N$—$N(Me)CH_2CO_2Bn$ (1.28 g, 6.58 mmol) and $HOBt.H_2O$ (1.03 g, 6.58 mmol) were added. Triethylamine (912 μL, 6.58 mmol) and EDC.HCl (1.26 g, 6.58 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline and dried by $Na_2SO_4$. After filtration, the mother liquor was distilled off under reduced pressure, and a white solid (771 mg, 1.52 mmol, two steps, 46%) was obtained by refining the residue obtained by silica gel chromatography (chloroform:methanol=100:1).

HRMS(ES+) calcd for $C_{25}H_{41}N_4O_7$ (M$^+$+H) 509.2975. found 509.2981.

(2) Synthesis of Compound 22b

[Chemical Formula 104]

(Compound 22b)

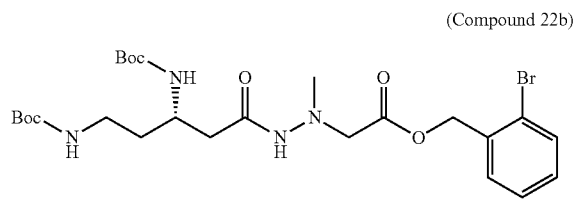

Compound 22b was synthesized by the same method as compound 22a using compound 17 (111 mg, 0.354 mmol) and H$_2$N—N(Me)CH$_2$CO$_2$Bn(o-Br) (62.6 mg, 0.229 mmol) (white solid, 75.4 mg, 0.128 mmol, two steps, 36%).

HRMS(ES+) calcd for C$_{25}$H$_{40}$N$_4$O$_7$Br (M$^+$+H) 587.2080. found 587.2092.

(B) Example Compounds 19-20

(1) Synthesis of Example Compound 19

[Chemical Formula 105]

(Example compound 19)

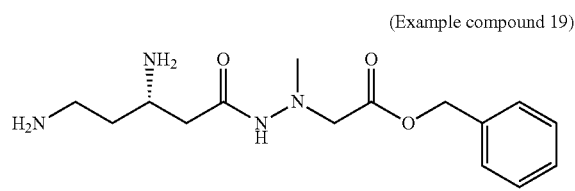

4 M hydrochloric acid/dioxane (2 mL) was added to compound 22a (64.9 mg, 0.128 mmol) while cooling by ice and stirred for one hour at room temperature. The solvent was distilled off under reduced pressure, and the residue obtained was dissolved in water. A colorless solid (34.6 mg, 64.5 μmol, 50%) was obtained by refining by high-performance liquid chromatography (solvent: H$_2$O in 0.1% TFA: CH$_3$CN in 0.1% TFA. A linear gradient of 15-45% CH$_3$CN in 0.1% TFA over 40 min. Flow rate 5 mL/min, detected at UV 222 nm).

$^1$H NMR (300 MHz, D$_2$O) δ7.42-7.40 (m, 5H), 5.20 (s, 2H), 3.67-3.62 (m, 3H), 3.06 (t, J=8.22 Hz, 2H), 2.63 (s, 3H), 2.52-2.48 (m, 2H), 2.07-1.96 (m, 2H); HRMS(ES+) calcd for C$_{15}$H$_{25}$N$_4$O$_3$ (M$^+$+H) 309.1927. found 309.1915.

(2) Synthesis of Example Compound 20

[Chemical Formula 106]

(Example compound 20)

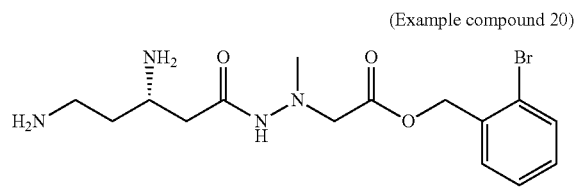

4 M hydrochloric acid/dioxane (2 mL) was added to compound 22b (52.0 mg, 88.5 μmol) while cooling by ice and stirred for one hour at room temperature. The solvent was distilled off under reduced pressure, and the residue obtained was dissolved in water. A white powder (26.9 mg, 43.9 μmol, 50%) was obtained by refining by high-performance liquid chromatography (solvent, H$_2$O in 0.1% TFA: CH$_3$CN in 0.1% TFA. A linear gradient of 30-50% CH$_3$CN in 0.1% TFA over 40 min. Flow rate 5 mL/min, detected at UV 222 nm).

HRMS(ES+) calcd for C$_{15}$H$_{24}$N$_4$O$_3$Br (M$^+$+H) 387.1032. found 387.1033.

Example 8

Synthesis of Example Compounds 21-24

Example compounds 21-24 were synthesized by the following synthesis scheme. In the scheme, the numbers appended below the structural formulas represent the compound numbers.

[Chemical Formula 107]

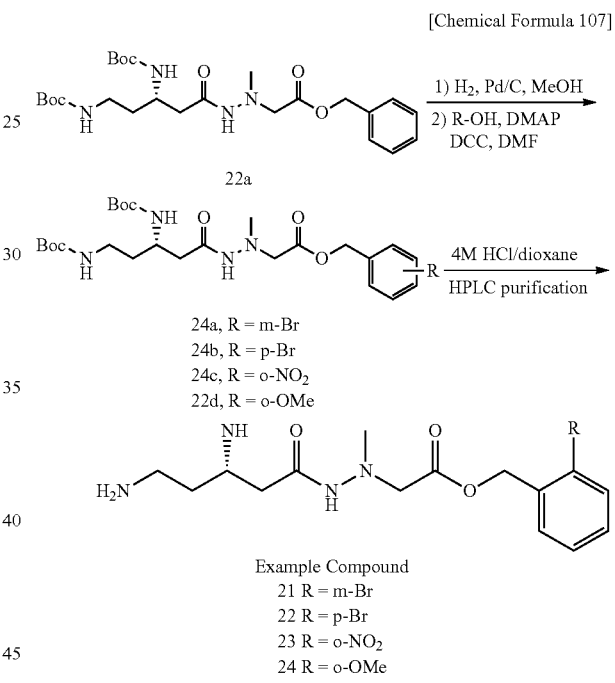

24a, R = m-Br
24b, R = p-Br
24c, R = o-NO$_2$
22d, R = o-OMe

Example Compound
21 R = m-Br
22 R = p-Br
23 R = o-NO$_2$
24 R = o-OMe (A) Compounds 24a-24d (1) Synthesis of Compound 24a

[Chemical Formula 108]

(Compound 24a)

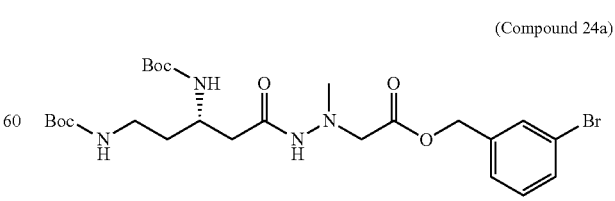

10% Pd/C (10.8 mg) was added to a methanol (2 mL) solution of compound 22a (108 mg, 0.212 mmol) under an argon atmosphere, hydrogen substitution was performed, and the solution was stirred for 1 hour 30 minutes at room temperature. The reaction solution was filtered by Celite, and the solvent was distilled off under reduced pressure. The residue obtained was used in the next reaction without refining. 3-Bromobenzyl alcohol (47.5 mg, 0.254 mmol) was added at room temperature to a DMF (2 mL) solution of the residue, and DMAP (2.59 mg, 21.2 µmol) and DCC (48.1 mg, 0.254 mmol) were added while cooling by ice and stirring, and stirred overnight at room temperature. The solvent was distilled off under reduced pressure, and the residue obtained was diluted by chloroform and filtered. The organic layer was washed with water and saturated saline and dried by $Na_2SO_4$. After filtration, the mother liquor was distilled off under reduced pressure, and a white solid (84.6 mg, 0.144 mmol, two steps, 68%) was obtained by refining the residue obtained by silica gel chromatography (chloroform:methanol=100:1).

HRMS(ES+) calcd for $C_{25}H_{40}N_4O_7Br$ ($M^++H$) 587.2080. found 587.2080.

(2) Synthesis of Compound 24b

[Chemical Formula 109]

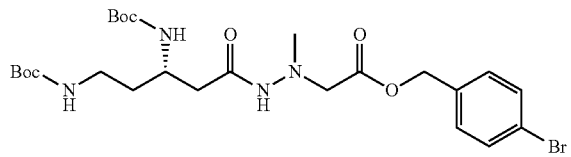

(Compound 24b)

Compound 24b was synthesized by the same method as compound 24a using compound 22a (120 mg, 0.236 mmol) and 4-bromobenzyl alcohol (53.0 mg, 0.283 mmol) (white solid, 71.6 mg, 0.122 mmol, two steps, 52%).

HRMS(ES+) calcd for $C_{25}H_{40}N_4O_7Br$ ($M^++H$) 587.2080. found 587.2078.

(3) Synthesis of Compound 24c

[Chemical Formula 110]

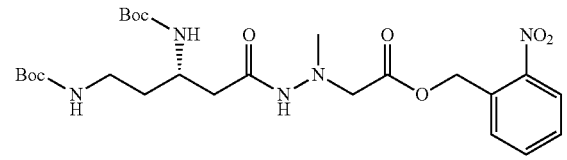

(Compound 24c)

Compound 24c was synthesized by the same method as compound 24a using compound 22a (99.6 mg, 0.196 mmol) and 2-nitrobenzyl alcohol (36.0 mg, 0.235 mmol) (white solid, 28.3 mg, 51.1 µmol, two steps, 26%).

$^1$H NMR (300 MHz, $CDCl_3$) δ8.13 (d, J=8.02 Hz, 1H), 7.75-7.65 (m, 2H), 7.65-7.51 (m, 2H), 6.74-6.50 (m, 3H), 5.40-5.18 (brd, 1H), 4.08-3.86 (m, 1H), 3.86-3.59 (m, 2H), 3.48-3.25 (m, 1H), 3.03-2.84 (m, 1H), 2.84-2.49 (m, 4H), 2.49-2.19 (m, 1H), 1.77-1.58 (m, 2H), 1.43 (s, 18H).

(4) Synthesis of Compound 24d

[Chemical Formula 111]

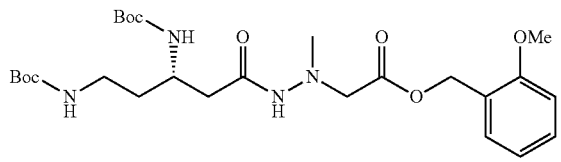

(Compound 24d)

Synthesized by the same method as compound 24a using compound 22a (114 mg, 0.224 mmol) and 2-methoxybenzyl alcohol (37.1 mg, 0.269 mmol) (white solid, 59.6 mg, 0.111 mmol, two steps, 49%).

HRMS(ES+) calcd for $C_{26}H_{43}N_4O_8$ ($M^++H$) 539.3081. found 539.3079.

(B) Example Compounds 21-24

(1) Synthesis of Example Compound 21

[Chemical Formula 112]

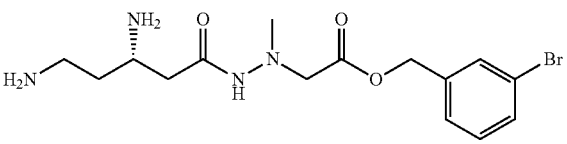

(Example compound 21)

Synthesized by the same method as example compound 20 using compound 24a (44.9 mg, 76.4 µmol) (white solid, 10.7 mg, 17.3 µmol, 23%).

$^1$H NMR (400 MHz, $D_2O$) δ7.64-7.58 (m, 2H), 7.43-7.33 (m, 2H), 5.20 (s, 2H), 3.78-3.67 (m, 3H), 3.11 (t, J=8.34 Hz, 2H), 2.67 (s, 3H), 2.60-2.49 (m, 2H), 2.16-1.96 (m, 2H); $^{13}$C NMR (100 MHz, $D_2O$) δ170.60, 168.82, 137.73, 131.49, 130.94, 130.53, 127.03, 121.94, 66.2, 58.4, 46.0, 44.3, 35.6, 34.5, 29.8.

(2) Synthesis of Example Compound 22

[Chemical Formula 113]

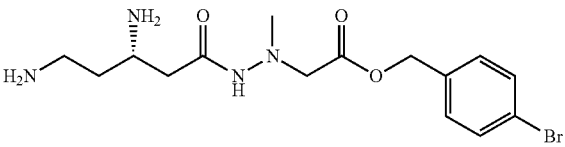

(Example compound 22)

Synthesized by the same method as example compound 20 using compound 24b (37.2 mg, 63.3 µmol) (white solid, 18.4 mg, 29.9 µmol, 47%).

HRMS(ES+) calcd for $C_{15}H_{24}N_4O_3Br$ (M$^+$+H) 387.1032. found 387.1024.

(3) Synthesis of Example Compound 23

[Chemical Formula 114]

(Example compound 23)

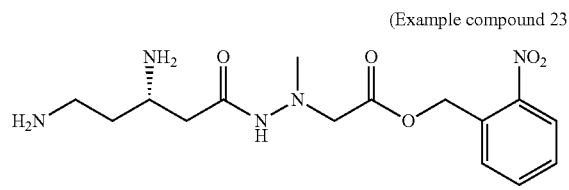

Synthesized by the same method as example compound 20 using compound 24c (28.3 mg, 51.1 μmol) (white solid, 21.8 mg, 37.5 μmol, 73%).

HRMS(ES+) calcd for $C_{15}H_{24}N_5O_5$ (M$^+$+H) 354.1777. found 354.1782.

(4) Synthesis of Example Compound 24

[Chemical Formula 115]

(Example compound 24)

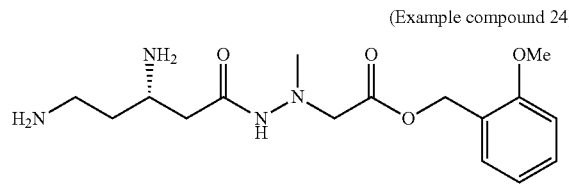

Synthesized by the same method as example compound 20 using compound 24d (30.4 mg, 56.5 μmol) (white solid, 20.8 mg, 36.8 μmol, 65%).

HRMS(ES+) calcd for $C_{16}H_{27}N_4O_4$ (M$^+$+H) 339.2032. found 339.2025.

Example 9

Synthesis of example compounds 25-28

Example compounds 25-28 were synthesized by the following synthesis scheme. In the scheme, the numbers appended below the structural formulas represent the compound numbers.

[Chemical Formula 116]

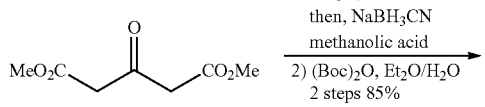

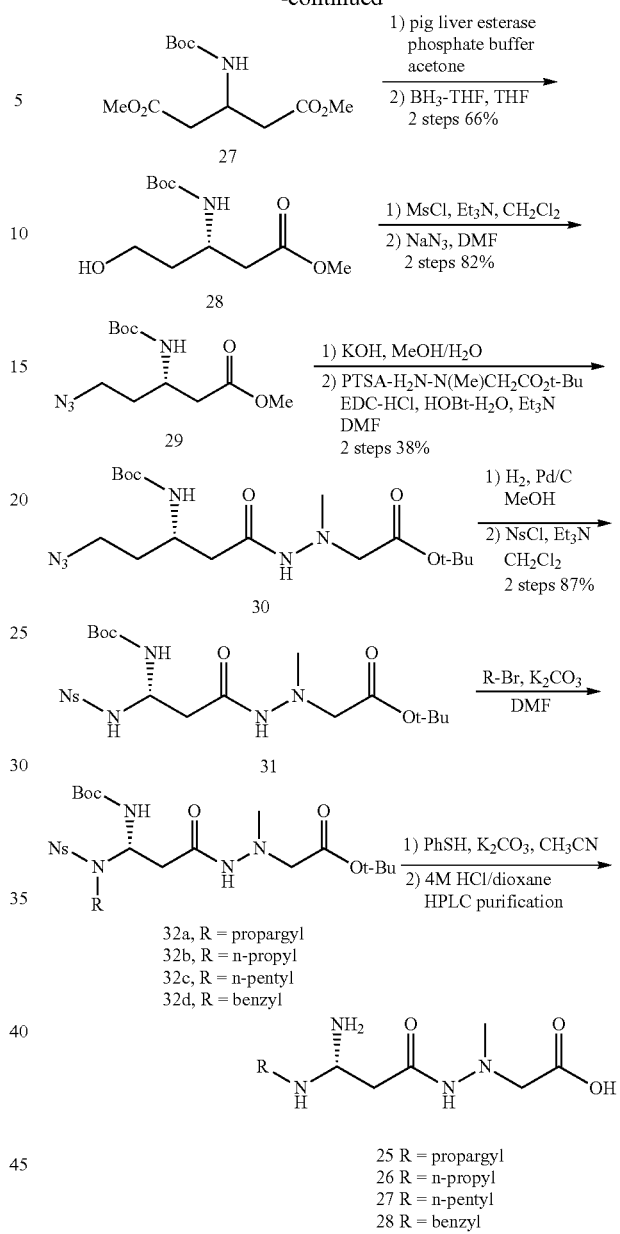

(A) Synthesis of Compound 27

[Chemical Formula 117]

(Compound 27)

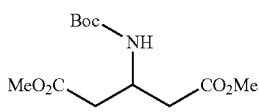

Ammonium acetate (23.1 g, 300 mmol) and molecular sieve 3A (24 g) were added to a methanol solution (285 mL) of dimethyl-1,3-acetonedicarboxylate (14.4 mL 100 mmol) and stirred for 5 hours 30 minutes at room temperature. Sodium cyanoborohydride (7.86 g, 125 mmol) was added, methanol-hydrochloric acid solution was added to pH 3, and the solution was stirred for 20 minutes at room temperature. The reaction solution was filtered by Celite, and the solvent was distilled off under reduced pressure. The residue obtained was dissolved in water (200 mL) and washed with diethyl ether. Sodium carbonate was added to bring the water layer near pH 10 while cooling by ice and stirring. Di-tert-butoxy-dicarbonate (21.8 g, 100 mmol) was added at the same temperature and stirred overnight at room temperature. The reaction solution was extracted by diethyl ether, and after washing the extract with saturated saline and drying (Na$_2$SO$_4$), the solvent was distilled off under reduced pressure. A colorless oily substance (23.3 g, 84.6 mmol, 85%) was obtained by refining the residue obtained by silica gel column chromatography (hexane:ethyl acetate=4:1).

$^1$H NMR (300 MHz, CDCl$_3$) δ5.39-5.30 (brd, 1H), 4.38-4.28 (m, 1H), 3.69 (s, 6H), 2.74-2.59 (m, 4H), 1.43 (s, 9H).

(B) Synthesis of Compound 28

[Chemical Formula 118]

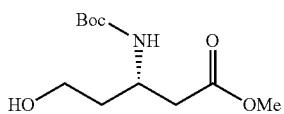

(Compound 28)

Acetone (4 mL) and esterase from porcine liver (Aldrich, 70.6 mg, 1200 units) were added to a phosphate buffer solution (pH 8, 0.5 M, 100 mL) of compound 27 (1.00 g, 3.60 mmol), maintained at pH 8 at 25° C., and stirred overnight. Concentrated hydrochloric acid was added to the reaction solution to bring the pH close to 1, and the solution was filtered. After extracting by chloroform and washing the organic layer with saturated saline and drying (Na$_2$SO$_4$), the solvent was distilled off under reduced pressure. The residue obtained was used in the next reaction without refining. Borane-tetrahydrofuran complex (1.0 M, 5.42 mL) was added dropwise while stirring at −78° C. to an anhydrous tetrahydrofuran solution (11 mL) of the residue under an argon atmosphere and stirred overnight at room temperature. Saturated ammonium chloride aqueous solution was added to the reaction solution while cooling by ice and stirring, followed by extraction by diethyl ether. After washing the organic layer with saturated saline and drying (Na$_2$SO$_4$), the solvent was distilled off under reduced pressure. A colorless oily substance (588 mg, 2.37 mmol, 66%) was obtained by refining the residue obtained by silica gel column chromatography (hexane:ethyl acetate=4:1).

[α]25D−20.7° (c1.00, CHCl$_3$), lit[α]25D−23.9° (c1.00, CHCl$_3$); $^1$H NMR (300 MHz, CDCl$_3$) δ5.42-5.36 (brs, 1H), 4.21-4.11 (m, 1H), 3.70 (s, 3H), 3.65-3.58 (m, 2H), 2.69-2.50 (m, 2H), 1.83-1.49 (m, 2H), 1.49 (s, 9H).

(C) Synthesis of Compound 29

[Chemical Formula 119]

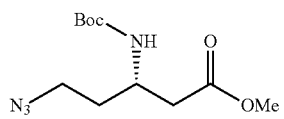

(Compound 29)

Triethylamine (42.1 μL, 0.303 mmol) and methanesulfonyl chloride (31.1 μL, 0.404 mmol) were added while cooling by ice and stirring to a dichloromethane solution (1 mL) of compound 28 (50.0 mg, 0.202 mmol) and stirred for 2 hours minutes at room temperature. Water was added to the reaction solution while cooling by ice and stirring, followed by extraction by chloroform. After washing the organic layer with saturated saline and drying (Na$_2$SO$_4$), the solvent was distilled off under reduced pressure. A mesilate (59.7 mg, 0.183 mmol, 90%), which was a white solid, was obtained by refining the residue obtained by silica gel column chromatography (hexane:ethyl acetate=1:1).

$^1$H NMR (300 MHz, CDCl$_3$) δ5.20-5.10 (brd, 1H), 4.35-4.22 (m, 2H), 4.19-4.01 (m, 1H), 3.70 (s, 3H), 3.04 (s, 3H), 2.68-2.53 (m, 2H), 2.05-1.96 (m, 2H), 1.44 (s, 9H).

Sodium azide (219 mg, 3.36 mmol) was added to a DMF (10 mL) of the above mesilate (365 mg, 1.12 mmol) and stirred overnight at 50° C. After the reaction solution had returned to room temperature, it was distilled under reduced pressure and a colorless oily substance (278 mg, 1.02 mmol, 91%) was obtained by refining the residue obtained by silica gel column chromatography (hexane:ethyl acetate=3:1).

$^1$H NMR (300 MHz, CDCl$_3$) δ5.13-5.03 (brd, 1H), 4.10-3.92 (m, 1H), 3.70 (s, 3H), 3.45-3.30 (m, 2H), 2.64-2.50 (m, 2H), 1.83-1.69 (m, 2H), 1.44 (s, 9H).

(D) Synthesis of Compound 30

[Chemical Formula 120]

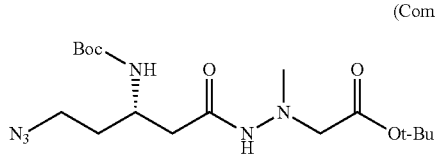

(Compound 30)

Potassium hydroxide (310 mg, 5.52 mmol) was added while cooling by ice and stirring to a methanol-water (2:1, 9 mL) mixed solution of compound 29 (500 mg, 1.84 mmol) and stirred for 1 hour 30 minutes at room temperature. The reaction solution was distilled off under reduced pressure, and 1 M hydrochloric acid solution was added to bring the residue obtained close to pH 1 while cooling by ice and stirring, followed by extraction by ethyl acetate. After washing the organic layer with saturated saline and drying (Na$_2$SO$_4$), the solvent was distilled off under reduced pressure. The residue obtained was used in the next reaction without refining. PTSA.H$_2$N—N(Me)CH$_2$CO$_2$t-Bu (1.22 g, 3.68 mmol) and HOBt.H$_2$O (564 mg, 3.68 mmol) were added to a DMF solution (9 mL) of the residue, triethylamine (510 μL, 3.68 mmol) and EDC.HCl (705 mg, 3.68 mmol) were added while cooling by ice and stirring, and stirred overnight at room temperature. The reaction solution was added to 10% citric acid aqueous solution and extracted by ethyl acetate. After washing the organic layer sequentially with saturated sodium bicarbonate aqueous solution, water, and saturated saline and drying (Na$_2$SO$_4$), the solvent was distilled off under reduced pressure. A colorless oily substance (241 mg, 0.601 mmol, two steps 33%) was obtained by refining the residue obtained by silica gel column chromatography (chloroform:methanol=80:1).

HRMS(ES+) calcd for C$_{17}$H$_{33}$N$_6$O$_5$ (M$^+$+H) 401.2512. found 401.2509.

(E) Synthesis of Compound 31

[Chemical Formula 121]

(Compound 31)

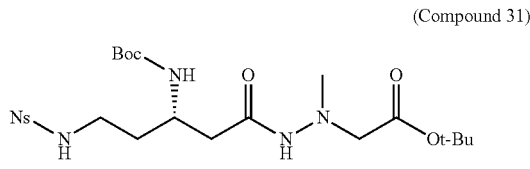

10% Pd/C (13.5 mg) was stirred for 1 hour 30 minutes under a hydrogen atmosphere in a methanol solution (2 mL) of compound 30 (135 mg, 0.337 mmol). The reaction solution was filtered by Celite, and the solvent was distilled off under reduced pressure. The residue obtained was used in the next reaction without refining. Triethylamine (56.0 μL, 0.404 mmol) and nosyl chloride (82.2 mg, 0.371 mmol) were added to a dichloromethane solution (2 mL) and stirred for 35 minutes at room temperature. Water was added to the reaction solution while cooling by ice and stirring, followed by extraction by chloroform. After washing the organic layer with saturated saline and drying ($Na_2SO_4$), the solvent was distilled off under reduced pressure. A colorless oily substance (164 mg, 0.293 mmol, two steps, 87%) was obtained by refining the residue obtained by silica gel column chromatography (chloroform:methanol=100:1).

HRMS(ES+) calcd for $C_{23}H_{38}N_5O_8S$ ($M^++H$) 560.2390. found 560.2386.

(F) Compounds 32a-32d

(1) Synthesis of Compound 32a

[Chemical Formula 122]

(Compound 32a)

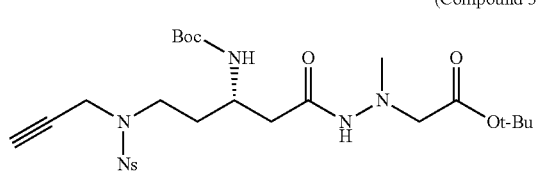

Potassium carbonate (14.7 mg, 0.107 mmol) and 3-bromopropyne (7.28 μL, 97.8 μmol) were added at room temperature to a DMF solution (2 mL) of compound 31 (49.7 mg, 88.9 μmol) and stirred for 1 hour 45 minutes at 50° C. After the reaction solution had returned to room temperature, water was added and it was extracted by ethyl acetate. After washing the organic layer with saturated saline and drying ($Na_2SO_4$), the solvent was distilled off under reduced pressure. A colorless oily substance (50.1 mg, 83.9 μmol, 94%) was obtained by refining the residue obtained by silica gel column chromatography (chloroform: methanol=100:1).

HRMS(ES+) calcd for $C_{26}H_{40}N_5O_9S$ ($M^++H$) 598.2547. found 598.2543.

(2) Synthesis of Compound 32b

[Chemical Formula 123]

(Compound 32b)

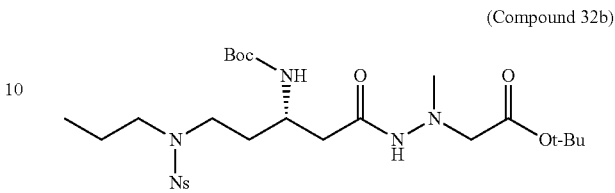

Synthesized by the same method as compound 32a using compound 31 (61.5 mg, 0.110 mmol) and 1-bromopropane (55.0 μL, 0.550 mmol) (yellow oily substance, 60.3 mg, 0.100 mmol, 91%).

HRMS(ES+) calcd for $C_{26}H_{44}N_5O_9S$ ($M^++H$) 602.2860. found 602.2845.

(3) Synthesis of Compound 32c

[Chemical Formula 124]

(Compound 32c)

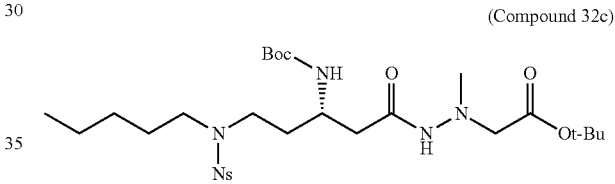

Synthesized by the same method as compound 32a using compound 31 (60.5 mg, 0.108 mmol) and 1-bromopentane (66.9 μL, 0.540 mmol) (colorless oily substance, 62.7 mg, 99.6 μmol, 92%).

HRMS(ES+) calcd for $C_{28}H_{48}N_5O_9S$ ($M^++H$) 630.3173. found 630.3174.

(4) Synthesis of Compound 32d

[Chemical Formula 125]

(Compound 32d)

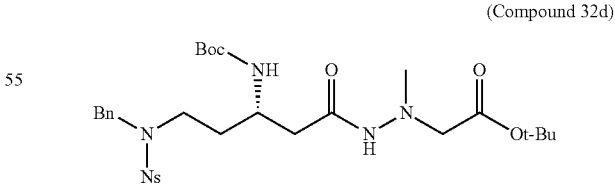

Synthesized by the same method as compound 32a using compound 31 (58.2 mg, 0.104 mmol) and benzyl bromide (12.4 μL, 0.114 mmol) (colorless oily substance, 52.7 mg, 81.2 μmol, 78%).

HRMS(ES+) calcd for $C_{30}H_{44}N_5O_9S$ ($M^++H$) 650.2860. found 650.2842.

(G) Example Compounds 25-28

(1) Synthesis of Example Compound 25

[Chemical Formula 126]

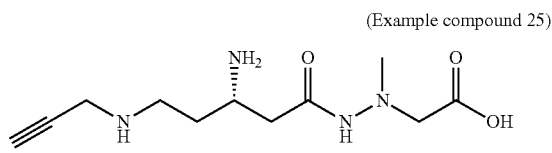

(Example compound 25)

Potassium carbonate (41.5 mg, 0.300 mmol) and thiophenol (30.6 μL, 0.300 mmol) were added to an acetonitrile solution (2 mL) of compound 32a (35.8 mg, 59.9 μmol) and stirred for 2 hours 15 minutes at room temperature. The reaction solution was filtered by Celite, and the solvent was distilled off under reduced pressure. 4 M hydrochloric acid/dioxane (2 mL) was added while cooling by ice and stirring to the residue obtained and stirred for one hour at room temperature. After distilling off the reaction solution, the residue was dissolved in water and refined by HPLC. A white solid (13.3 mg, 27.4 μmol, two steps, 46%) was obtained by freeze-drying the solvent.

$^1$H NMR (300 MHz, D$_2$O) δ3.96 (d, J=2.49 Hz, 2H), 3.80-3.71 (m, 1H), 3.64 (s, 2H), 3.35-3.20 (m, 2H), 3.01 (t, J=2.56 Hz, 1H), 2.68-2.54 (m, 5H), 2.17-2.05 (m, 2H); HRMS(ES+) calcd for C$_{11}$H$_{21}$N$_4$O$_3$ (M$^+$+H) 257.1614. found 257.1616.

(2) Synthesis of Example Compound 26

[Chemical Formula 127]

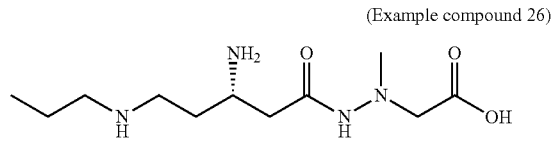

(Example compound 26)

Synthesized by the same method as example compound 25 using compound 32b (43.2 mg, 71.8 μmol) (white solid, 18.7 mg, 38.3 μmol, two steps, 53%).

$^1$H NMR (300 MHz, D$_2$O) δ3.76-3.72 (m, 1H), 3.65 (s, 2H), 3.25-3.08 (m, 2H), 3.02 (t, J=7.44 Hz, 2H), 2.67-2.54 (m, 5H), 2.20-2.00 (m, 2H), 1.75-1.62 (m, 2H), 0.95 (t, J=7.56 Hz, 3H); HRMS(ES+) calcd for C$_{11}$H$_{25}$N$_4$O$_3$ (M$^+$+H) 261.1927. found 261.1931.

(3) Synthesis of Example Compound 27

[Chemical Formula 128]

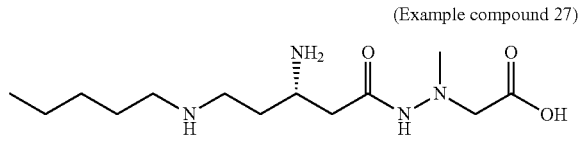

(Example compound 27)

Synthesized by the same method as example compound 25 using compound 33c (39.2 mg, 62.2 μmol) (white solid, 11.4 mg, 22.0 μmol, two steps, 35%).

$^1$H NMR (300 MHz, D$_2$O) δ3.76-3.67 (m, 1H), 3.56 (s, 2H), 3.19-3.08 (m, 2H), 3.02 (t, J=7.63 Hz, 2H), 2.66-2.51 (m, 5H), 2.14-2.02 (m, 2H), 1.67-1.60 (m, 2H), 1.35-1.22 (m, 4H), 0.85 (t, J=6.89 Hz, 3H); HRMS(ES+) calcd for C$_{13}$H$_{29}$N$_4$O$_3$ (M$^+$+H) 289.2240. found 289.2238.

(4) Synthesis of Example Compound 28

[Chemical Formula 129]

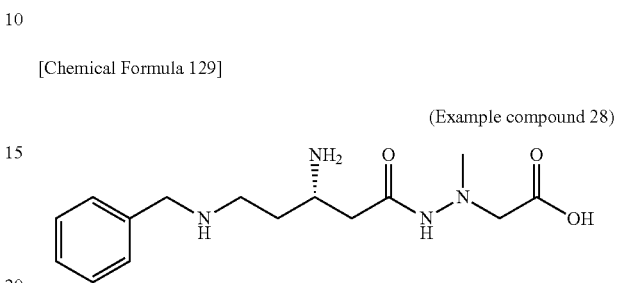

(Example compound 28)

Synthesized by the same method as example compound 25 using compound 33d (35.2 mg, 54.2 μmol) (white solid, 9.23 mg, 17.2 μmol, two steps, 32%).

$^1$H NMR (300 MHz, D$_2$O) δ7.49-7.43 (m, 5H), 4.24 (s, 2H), 3.72-3.68 (m, 1H), 3.56 (s, 2H), 3.20-3.13 (m, 2H), 2.62-2.49 (m, 5H), 2.11-2.05 (m, 2H); HRMS(ES+) calcd for C$_{15}$H$_{25}$N$_4$O$_3$ (M$^+$+H) 309.1927. found 309.1920.

Example 10

Synthesis of Example Compounds 29-31

Example compounds 29-31 were synthesized by the following synthesis scheme. In the scheme, the numbers appended below the structural formulas represent the compound numbers.

[Chemical Formula 130]

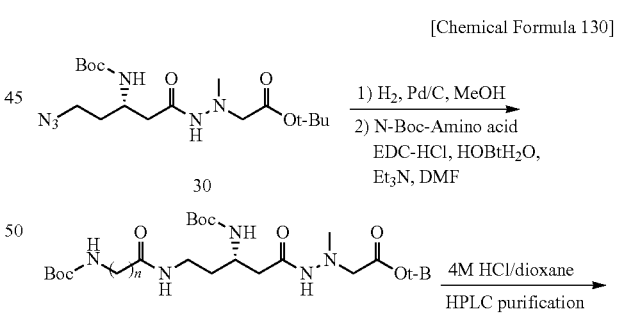

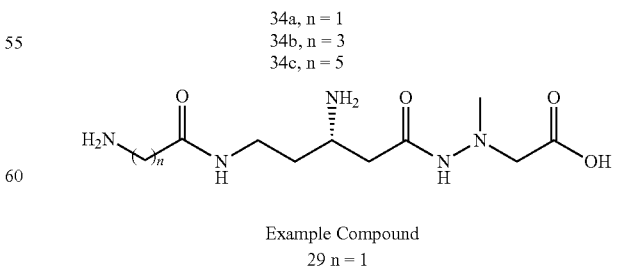

Example Compound
29 n = 1
30 n = 3
31 n = 5

(A) Compounds 34a-34c

(1) Synthesis of Compound 34a

[Chemical Formula 131]

(Compound 34a)

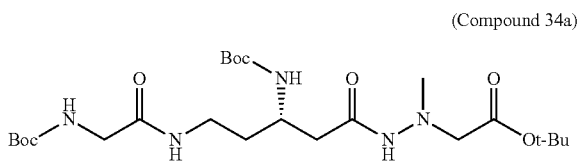

10% Pd/C (5.49 mg) was stirred for 1 hour 30 minutes under a hydrogen atmosphere in a methanol solution (2 mL) of compound 30 (54.9 mg, 0.137 mmol). The reaction solution was filtered by Celite, and the solvent was distilled off under reduced pressure. The residue obtained was used in the next reaction without refining. N-Boc-glycine (26.5 mg, 0.151 mmol) and HOBt.H$_2$O (23.1 mg, 0.151 mmol) were added to a DMF solution (2 mL) of the residue, triethylamine (22.8 μL, 0.164 mmol) and EDC.HCl (31.5 mg, 0.164 mmol) were added while cooling by ice and stirring, and stirred overnight at room temperature. The reaction solution was added to 10% citric acid aqueous solution and extracted by ethyl acetate. After washing the organic layer sequentially with saturated sodium bicarbonate aqueous solution, water, and saturated saline and drying (Na$_2$SO$_4$), the solvent was distilled off under reduced pressure. A colorless oily substance (57.6 mg, 0.108 mmol, two steps, 79%) was obtained by refining the residue obtained by silica gel column chromatography (chloroform: methanol=80:1).

HRMS(ES+) calcd for C$_{24}$H$_{46}$N$_5$O$_8$ (M$^+$+H) 532.3346. found 532.3329.

(2) Synthesis of Compound 34b

[Chemical Formula 132]

(Compound 34b)

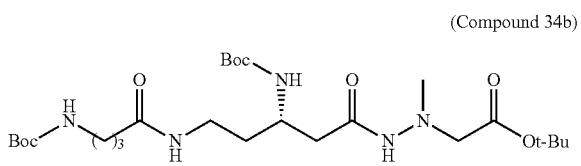

Synthesized by the same method as compound 34a using compound 30 (55.2 mg, 0.138 mmol) and N-Boc-γ-aminobutyric acid (30.9 mg, 0.152 mmol) (white solid, 64.0 mg, 0.114 mmol, two steps, 83%).

HRMS(ES+) calcd for C$_{26}$H$_{50}$N$_5$O$_8$ (M$^+$+H) 560.3659. found 560.3646.

(3) Compound 34c

[Chemical Formula 133]

(Compound 34c)

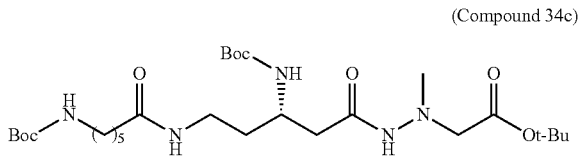

Synthesized by the same method as compound 34a using compound 30 (48.1 mg, 0.120 mmol) and N-Boc-ε-aminocaproic acid (30.5 mg, 0.132 mmol) (white solid, 52.5 mg, 89.4 μmol, two steps, 74%).

HRMS(ES+) calcd for C$_{28}$H$_{54}$N$_5$O$_8$ (M$^+$+H) 588.3972. found 588.3979.

(B) Example Compounds 29-31

(1) Synthesis of Example Compound 29

[Chemical Formula 134]

(Example compound 29)

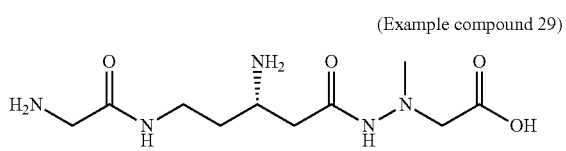

4 M hydrochloric acid/dioxane (2 mL) was added while cooling by ice and stirring to compound 34a (33.7 mg, 63.4 μmol) and stirred for one hour at room temperature. After distilling off the reaction solution under reduced pressure, the residue was dissolved in water and refined by HPLC. A colorless solid (13.9 mg, 27.5 μmol, 43%) was obtained by freeze drying the solvent.

$^1$H NMR (300 MHz, D$_2$O) δ3.80 (s, 2H), 3.66-3.57 (m, 3H), 3.41-3.28 (m, 2H), 2.68-2.50 (m, 5H), 1.94-1.80 (m, 2H); HRMS(ES+) calcd for C$_{10}$H$_{22}$N$_5$O$_4$ (M$^+$+H) 276.1672. found 276.1666.

(2) Synthesis of Example Compound 30

[Chemical Formula 135]

(Example compound 30)

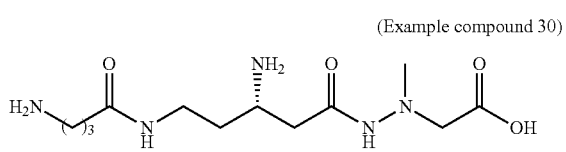

Synthesized by the same method as example compound 29 using compound 34b (32.4 mg, 57.9 μmol) (colorless solid, 17.3 mg, 32.5 μmol, 56%).

$^1$H NMR (300 MHz, D$_2$O) δ3.66-3.56 (m, 3H), 3.35-3.21 (m, 2H), 2.99 (t, J=7.73 Hz, 2H), 2.68-2.50 (m, 5H), 2.36 (t, J=7.51 Hz, 2H), 1.97-1.80 (m, 4H); HRMS(ES+) calcd for C$_{12}$H$_{26}$N$_5$O$_4$ (M$^+$+H) 304.1985. found 304.1982.

(3) Synthesis of Example Compound 31

[Chemical Formula 136]

(Example compound 31)

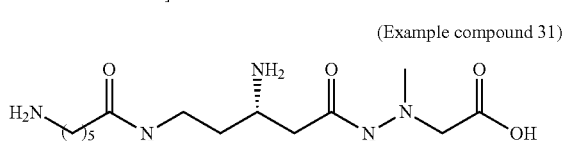

Synthesized by the same method as example compound 29 using compound 34c (33.3 mg, 56.7 μmol) (colorless solid, 17.5 mg, 31.2 μmol, 55%).

$^1$H NMR (300 MHz, D$_2$O) δ3.66 (s, 2H), 3.65-3.53 (m, 1H), 3.38-3.21 (m, 2H), 2.97 (t, J=7.48 Hz, 2H), 2.68-2.50

(m, 5H), 2.26 (t, J=7.44 Hz, 2H), 1.91-1.78 (m, 2H), 1.70-1.55 (m, 4H), 1.40-1.30 (m, 2H); HRMS(ES+) calcd for $C_{14}H_{30}N_5O_4$ (M$^+$+H) 332.2298. found 332.2289.

Example 11

Synthesis of Example Compound 32

Example compound 32 was synthesized by the following synthesis scheme. In the scheme, the numbers appended below the structural formulas represent the compound numbers.

[Chemical Formula 137]

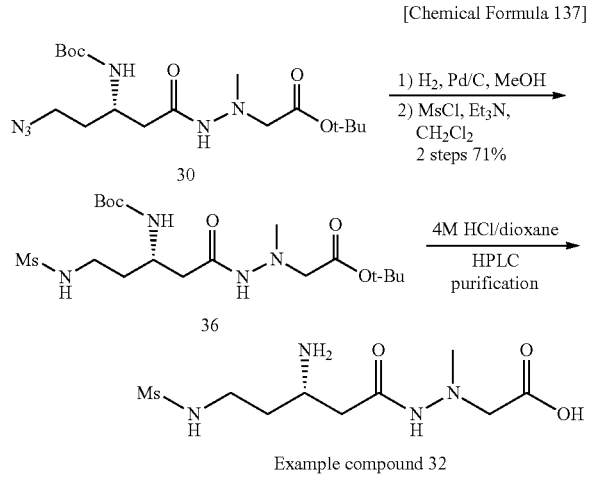

(1) Synthesis of Compound 36

[Chemical Formula 138]

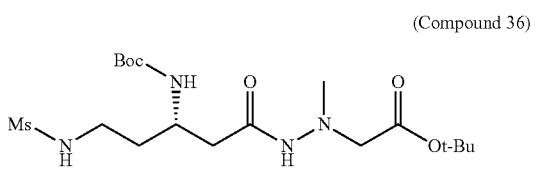

10% Pd/C (5.36 mg) was stirred for 2 hours 30 minutes under a hydrogen atmosphere in a methanol solution (2 mL) of compound 30 (53.6 mg, 0.134 mmol). The reaction solution was filtered by Celite, and the solvent was distilled off under reduced pressure. The residue obtained was used in the next reaction without refining. Triethylamine (22.3 µL, 0.161 mmol) and methanesulfonyl chloride (11.4 mg, 0.147 mmol) were added while cooling by ice and stirring to a dichloromethane solution (2 mL) of the residue and stirred for one hour at room temperature. Water was added to the reaction solution while cooling by ice and stirring, followed by extraction by chloroform. After washing the organic layer by saturated saline and drying ($Na_2SO_4$), the solvent was distilled off under reduced pressure. A colorless oily substance (43.1 mg, 95.3 µmol, two steps, 71%) was obtained by refining the residue obtained by silica gel column chromatography (chloroform:methanol=100:1).

HRMS(ES+) calcd for $C_{18}H_{37}N_4O_7S$ (M$^+$+H) 453.2383. found 453.2390.

(2) Synthesis of Example Compound 32

[Chemical Formula 139]

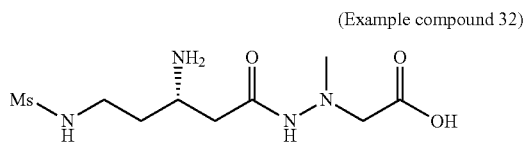

4 M hydrochloric acid/dioxane (2 mL) was added while cooling by ice and stirring to compound 36 (22.1 mg, 48.9 µmol) and stirred for one hour at room temperature. After distilling off the reaction solution under reduced pressure, the residue was dissolved in water and refined by HPLC. A white solid (9.86 mg, 24.0 µmol, 49%) was obtained by freeze drying the solvent.

$^1$H NMR (300 MHz, D$_2$O) 63.75-3.69 (m, 1H), 3.63 (s, 2H), 3.24-3.13 (m, 2H), 3.05 (s, 3H), 2.66-2.48 (m, 5H), 1.97-1.83 (m, 2H); HRMS(ES+) calcd for $C_9H_{21}N_4O_5S$ (M$^+$+H) 297.1233. found 297.1221.

Example 12

Synthesis of Example Compounds 33-46

Example compounds 33-46 were synthesized by the following synthesis scheme. In the scheme, the numbers appended below the structural formulas represent the compound numbers.

[Chemical Formula 140]

(A) Synthesis of Compound 38

[Chemical Formula 141]

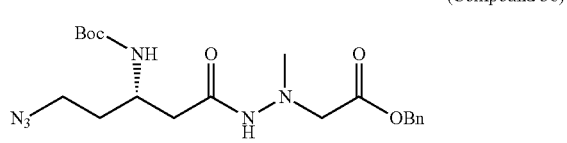

(Compound 38)

Synthesized by the same method as compound 30 using compound 29 (100 mg, 0.367 mmol) and H$_2$N—N(Me)CH$_2$CO$_2$Bn (143 mg, 0.734 mmol) (colorless oily substance, 127 mg, 0.291 mmol, two steps, 79%).

HRMS(ES+) calcd for C$_{20}$H$_{30}$N$_6$O$_5$Na (M$^+$+Na) 457.2175. found 457.2175.

(B) Compounds 39a-39n

(1) Synthesis of Compound 39a

[Chemical Formula 142]

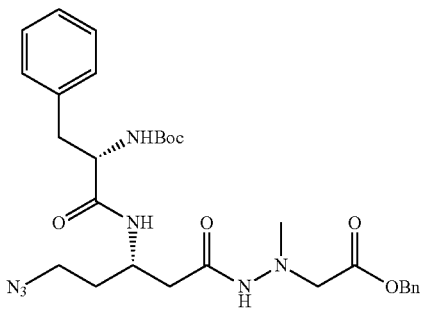

(Compound 39a)

4 M hydrochloric acid/dioxane (2.0 mL) was added while cooling by ice to compound 38 (53.6 mg, 0.123 mmol) and stirred for one hour at room temperature. The solvent was distilled off under reduced pressure, and the residue obtained was used in the next reaction without refining. The residue was dissolved in DMF (2 mL), and Boc-Phe-OH (65.4 mg, 0.246 mmol) and HOBt.H$_2$O (37.8 mg, 0.246 mmol) were added. Triethylamine (34.2 µL, 0.246 mmol) and EDC.HCl (47.3 mg, 0.246 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline, and dried by Na$_2$SO$_4$. After filtration, the mother liquor was distilled off under reduced pressure, and a white solid (68.5 mg, 0.118 mmol, two steps, 96%) was obtained by refining the residue obtained by silica gel chromatography (chloroform:methanol=80:1).

HRMS(ES+) calcd for C$_{29}$H$_{40}$N$_7$O$_6$ (M$^+$+H) 582.3040. found 582.3030.

(2) Synthesis of Compound 39b

[Chemical Formula 143]

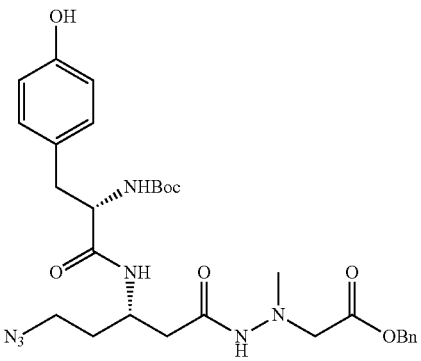

(Compound 39b)

Synthesized by the same method as compound 39a using compound 38 (42.8 mg, 98.6 µmol) (white solid, 49.5 mg, 82.9 µmol, two steps, 84%).

HRMS(ES+) calcd for C$_{29}$H$_{39}$N$_7$O$_7$Na (M$^+$+Na) 620.2809. found 620.2811.

(3) Synthesis of Compound 39c

[Chemical Formula 144]

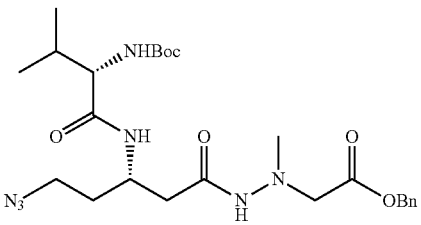

(Compound 39c)

Synthesized by the same method as compound 39a using compound 38 (44.3 mg, 0.102 mmol) (white solid, 53.2 mg, 99.8 µmol, two steps, 98%).

HRMS(ES+) calcd for C$_{25}$H$_{40}$N$_7$O$_6$ (M$^+$+H) 534.3040. found 534.3029.

(4) Synthesis of Compound 39d

[Chemical Formula 145]

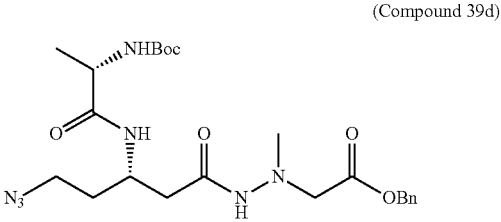

(Compound 39d)

Synthesized by the same method as compound 39a using compound 38 (109 mg, 0.422 mmol) (yellow oily substance, 38.0 mg, 75.2 µmol, two steps, 18%).

$^1$H NMR (300 MHz, CDCl$_3$) δ7.88 (s, 1H), 7.40-7.33 (m, 5H), 7.25-7.10 (m, 1H), 5.18 (s, 2H), 5.15-4.99 (m, 1H), 4.40-4.07 (m, 1H), 4.07-3.99 (m, 1H), 3.82-3.44 (m, 2H), 3.34 (t, J=6.23 Hz, 2H), 3.02-2.81 (m, 3H), 2.80-2.70 (m, 3H), 2.64-2.50 (m, 1H), 2.44-2.23 (m, 1H), 2.03-2.67 (m, 2H), 1.44 (s, 9H).

(5) Synthesis of Compound 39e

[Chemical Formula 146]

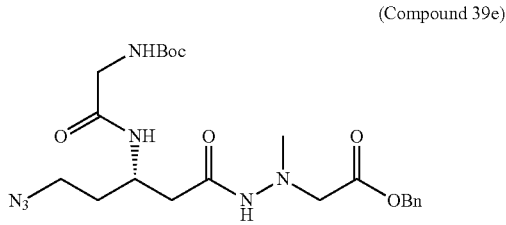
(Compound 39e)

Synthesized by the same method as compound 39a using compound 38 (46.2 mg, 0.106 mmol) (yellow oily substance, 42.7 mg, 89.7 μmol, two steps, 84%).

HRMS(ES+) calcd for $C_{22}H_{34}N_7O_6$ (M$^+$+H) 492.2571. found 492.2576.

(6) Synthesis of Compound 39f

[Chemical Formula 147]

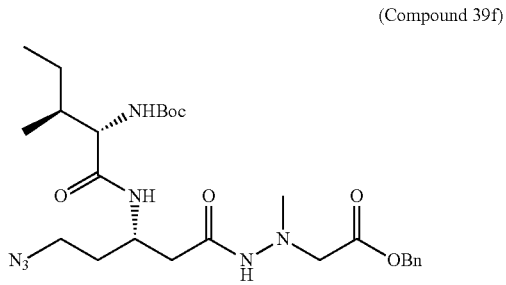
(Compound 39f)

Synthesized by the same method as compound 39a using compound 38 (52.8 mg, 0.122 mmol) (white solid, 58.5 mg, 0.107 mmol, two steps, 88%).

HRMS(ES+) calcd for $C_{26}H_{42}N_7O_6$ (M$^+$+H) 548.3197. found 548.3201.

(7) Synthesis of Compound 39g

[Chemical Formula 148]

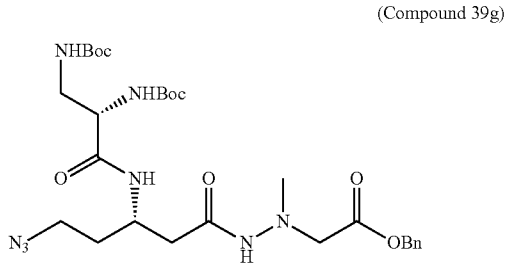
(Compound 39g)

Synthesized by the same method as compound 39a using compound 38 (50.0 mg, 0.115 mmol) (white solid, 30.0 mg, 48.4 μmol, two steps, 42%).

$^1$H NMR (300 MHz, CDCl$_3$) δ8.21 (s, 1H), 7.42-7.27 (m, 5H), 5.88-5.76 (brs, 1H), 5.49-5.10 (m, 4H), 4.40-4.22 (m, 1H), 4.22-4.04 (m, 1H), 3.90-3.40 (m, 4H), 3.34 (t, J=6.16 Hz, 2H), 3.03-2.55 (m, 4H), 2.43-2.19 (m, 1H), 1.90-1.71 (m, 2H), 1.45 (s, 18H).

(8) Synthesis of Compound 39h

[Chemical Formula 149]

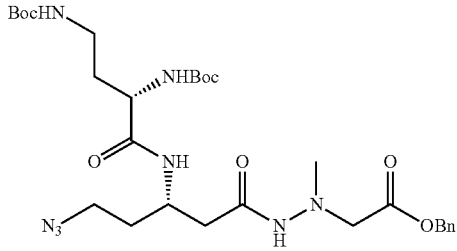
(Compound 39h)

Synthesized by the same method as compound 39a using compound 38 (50.7 mg, 0.117 mmol) (white solid, 25.9 mg, 40.8 μmol, two steps, 35%).

$^1$H NMR (300 MHz, CDCl$_3$) δ7.86 (s, 1H), 7.42-7.27 (m, 5H), 5.42-5.01 (m, 5H), 4.45-4.23 (m, 1H), 4.16-4.00 (m, 1H), 3.83-3.56 (m, 2H), 3.46-3.24 (m, 2H), 3.14-2.97 (m, 2H), 2.97-2.51 (m, 4H), 2.44-2.24 (m, 1H), 2.10-1.57 (m, 4H), 1.44 (s, 18H).

(9) Synthesis of Compound 39i

[Chemical Formula 150]

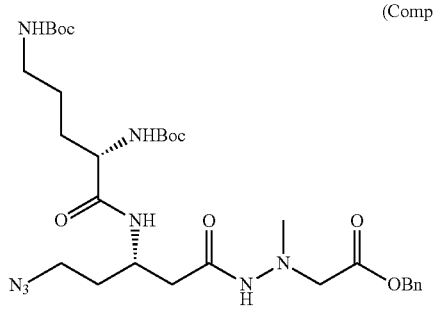
(Compound 39i)

Synthesized by the same method as compound 39a using compound 38 (51.4 mg, 0.118 mmol) (white solid, 74.3 mg, 0.115 mmol, two steps, 97%).

HRMS(ES+) calcd for $C_{30}H_{49}N_8O_8$ (M$^+$+H) 649.3673. found 649.3679.

(10) Synthesis of Compound 39j

[Chemical Formula 151]

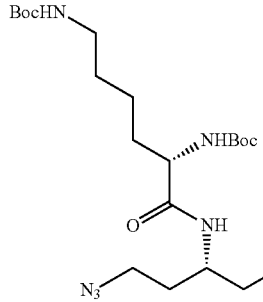
(Compound 39j)

Synthesized by the same method as compound 39a using compound 38 (50.9 mg, 0.117 mmol) (yellow solid, 72.3 mg, 0.109 mol, two steps, 93%).

HRMS(ES+) calcd for $C_{31}H_{51}N_8O_8$ (M$^+$+H) 663.3830. found 663.3823.

(11) Synthesis of Compound 39k

[Chemical Formula 152]

(Compound 39k)

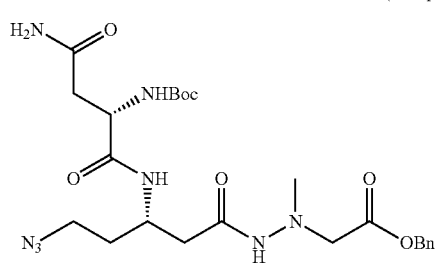

Synthesized by the same method as compound 39a using compound 38 (50.0 mg, 0.115 mmol) (white solid, 41.0 mg, 74.8 μmol, two steps, 65%).
HRMS(ES+) calcd for $C_{24}H_{37}N_8O_7$(M$^+$+H) 549.2785. found 549.2785.

(12) Synthesis of Compound 39l

[Chemical Formula 153]

(Compound 39l)

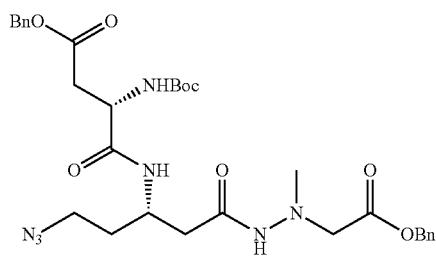

Synthesized by the same method as compound 39a using compound 38 (50.2 mg, 0.116 mmol) (white solid, 47.9 mg, 74.9 μmol, 65%).
HRMS(ES+) calcd for $C_{31}H_{42}N_7O_8$ (M$^+$+H) 640.3095. found 640.3099.

(13) Synthesis of Compound 39m

[Chemical Formula 154]

(Compound 39m)

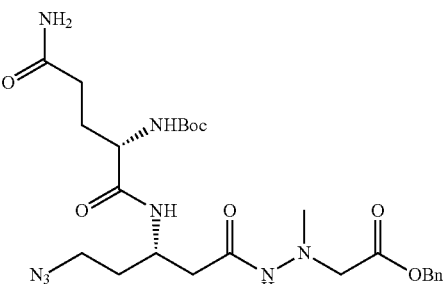

Synthesized by the same method as compound 39a using compound 38 (50.9 mg, 0.117 mmol) (white solid, 54.9 mg, 97.6 μmol, two steps, 83%).

$^1$H NMR (300 MHz, CDCl$_3$) δ8.11 (s, 1H), 7.80-7.42 (m, 1H), 7.42-7.27 (m, 5H), 7.02-6.74 (m, 1H), 6.39-6.10 (m, 1H), 5.78-5.43 (m, 1H), 5.18 (s, 2H), 4.50-4.22 (m, 1H), 4.18-3.90 (m, 1H), 3.82-3.55 (m, 2H), 3.36 (s, 2H), 2.88-2.61 (m, 3H), 2.45-1.70 (m, 8H), 1.43 (s, 9H).

(14) Synthesis of Compound 39n

[Chemical Formula 155]

(Compound 39n)

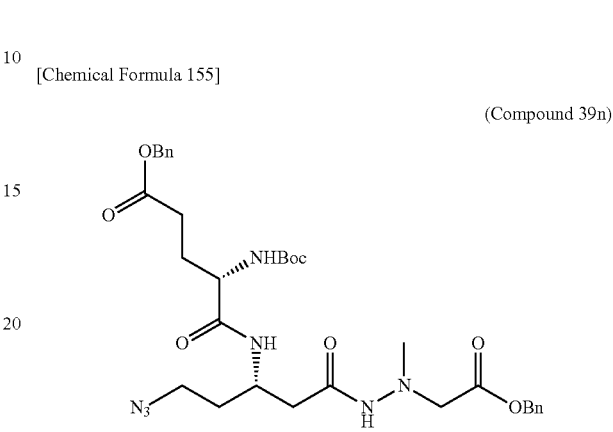

Synthesized by the same method as compound 39a using compound 38 (52.7 mg, 0.121 mmol) (white solid, 54.7 mg, 86.1 μmol, two steps, 71%).
HRMS(ES+) calcd for $C_{32}H_{44}N_7O_8$ (M$^+$+H) 654.3251. found 654.3262.

(C) Example Compounds 33-46

(1) Synthesis of Example Compound 33

[Chemical Formula 156]

(Example compound 33)

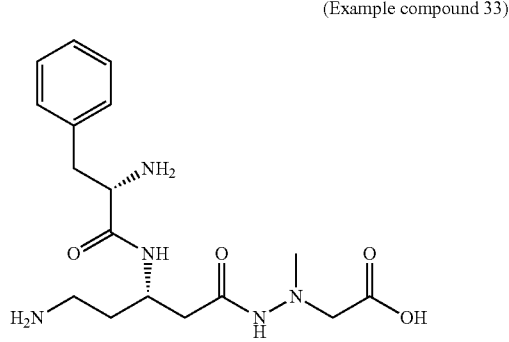

10% Pd/C (4.2 mg) was added to a methanol (2 mL) solution of compound 39a (42.4 mg, 72.9 μmol) under an argon atmosphere, hydrogen substitution was performed, and the solution was stirred for one hour at room temperature. The reaction solution was filtered by Celite, and the solvent was distilled off under reduced pressure. The residue obtained was used in the next reaction without refining. 4 M hydrochloric acid/dioxane (2 mL) was added to the residue while cooling by ice and stirred for one hour at room temperature. The solvent was distilled off under reduced pressure, and the residue obtained was dissolved in water. A white solid (10.4 mg, 17.5 μmol, two steps, 24%) was obtained by refining by high-performance liquid chromatography (solvent, H$_2$O in 0.1% TFA: CH$_3$CN in 0.1% TFA. A linear gradient of 10-15% CH$_3$CN in 0.1% TFA over 40 min. Flow rate 5 mL/min, detected at 222 nm UV).

HRMS(ES+) calcd for $C_{17}H_{28}N_5O_4$ (M$^+$+H) 366.2141. found 366.2141.

(2) Synthesis of Example Compound 34

[Chemical Formula 157]

(Example compound 34)

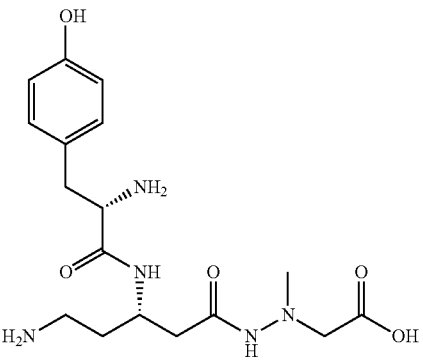

Synthesized by the same method as example compound 33 using compound 39b (30.0 mg, 50.2 μmol) (white solid, 5.12 mg, 8.95 μmol, two steps, 16%).
HRMS(ES+) calcd for $C_{17}H_{28}N_5O_5$ (M$^+$+H) 382.2090. found 382.2089.

(3) Synthesis of Example Compound 35

[Chemical Formula 158]

(Example compound 35)

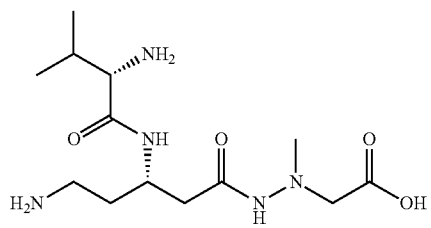

Synthesized by the same method as example compound 33 using compound 39c (33.4 mg, 62.6 μmol) (yellow solid, 4.07 mg, 7.47 μmol, two steps, 12%).
HRMS(ES+) calcd for $C_{13}H_{28}N_5O_4$ (M$^+$+H) 318.2141. found 318.2142.

(4) Synthesis of Example Compound 36

[Chemical Formula 159]

(Example compound 36)

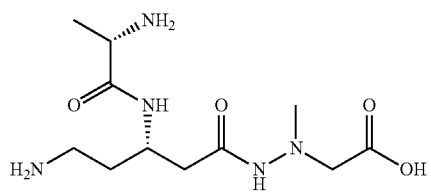

Synthesized by the same method as example compound 33 using compound 39d (29.8 mg, 58.9 μmol) (yellow solid, 11.2 mg, 21.6 μmol, two steps, 38%).
HRMS(ES+) calcd for $C_{11}H_{24}N_5O_4$ (M$^+$+H) 290.1828. found 290.1819.

(5) Synthesis of Example Compound 37

[Chemical Formula 160]

(Example compound 37)

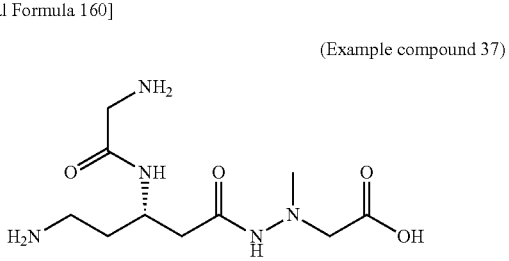

Synthesized by the same method as example compound 33 using compound 39e (24.7 mg, 51.9 μmol) (green solid, 7.50 mg, 14.9 μmol, two steps, 29%).
HRMS(ES+) calcd for $C_{10}H_{22}N_5O_4$ (M$^+$+H) 276.1672. found 276.1675.

(6) Synthesis of Example Compound 38

[Chemical Formula 161]

(Example compound 38)

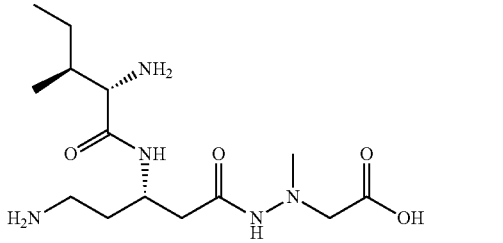

Synthesized by the same method as example compound 33 using compound 39f (32.0 mg, 58.5 μmol) (yellow solid, 13.4 mg, 23.9 μmol, two steps, 41%).
HRMS(ES+) calcd for $C_{14}H_{30}N_5O_4$ (M$^+$+H) 332.2298. found 332.2291.

(7) Synthesis of Example Compound 39

[Chemical Formula 162]

(Example compound 39)

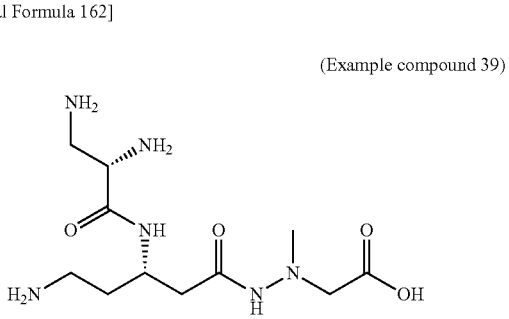

Synthesized by the same method as example compound 33 using compound 39g (30.0 mg, 48.4 μmol) (yellow solid, 9.20 mg, 14.2 μmol, two steps, 29%).
HRMS(ES+) calcd for $C_{11}H_{25}N_6O_4$ (M$^+$+H) 305.1937. found 305.1930.

(8) Synthesis of Example Compound 40

[Chemical Formula 163]

(Example compound 40)

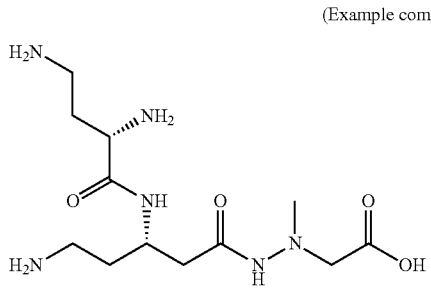

Synthesized by the same method as example compound 33 using compound 39h (25.9 mg, 40.8 µmol) (yellow solid, 4.96 mg, 7.51 µmol, two steps, 18%).

HRMS(ES+) calcd for $C_{12}H_{27}N_6O_4$ (M$^+$+H) 319.2094. found 319.2085.

(9) Synthesis of Example Compound 41

[Chemical Formula 164]

(Example compound 41)

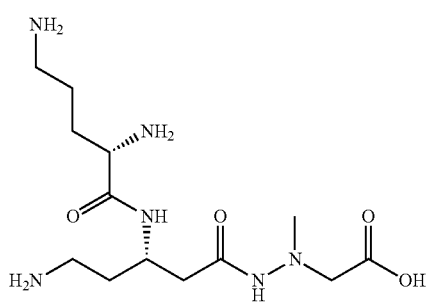

Synthesized by the same method as example compound 33 using compound 39i (44.6 mg, 68.8 µmol) (yellow solid, 3.35 mg, 4.97 µmol, two steps, 7.2%).

HRMS(ES+) calcd for $C_{13}H_{29}N_6O_4$ (M$^+$+H) 333.2250. found 333.2238.

(10) Synthesis of Example Compound 42

[Chemical Formula 165]

(Example compound 42)

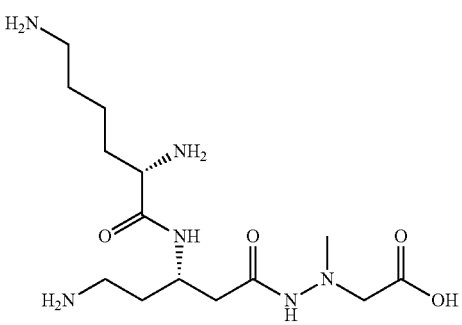

Synthesized by the same method as example compound 33 using compound 39j (57.8 mg, 87.3 µmol) (yellow solid, 11.89 mg, 17.3 µmol, two steps, 20%).

HRMS(ES+) calcd for $C_{14}H_{31}N_6O_4$ (M$^+$+H) 347.2407. found 347.2408.

(11) Synthesis of Example Compound 43

[Chemical Formula 166]

(Example compound 43)

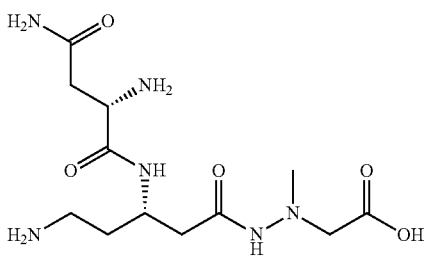

Synthesized by the same method as example compound 33 using compound 39k (34.6 mg, 63.1 µmol) (yellow solid, 10.64 mg, 19.0 µmol, two steps, 30%).

HRMS(ES+) calcd for $C_{12}H_{25}N_6O_5$ (M$^+$+H) 333.1886. found 333.1880.

(12) Synthesis of Example Compound 44

[Chemical Formula 167]

(Example compound 44)

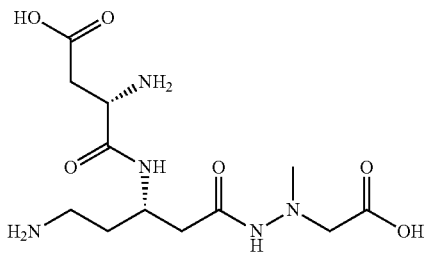

Synthesized by the same method as example compound 33 using compound 39l (34.4 mg, 53.8 µmol) (green solid, 9.56 mg, 17.0 µmol, two steps, 32%).

HRMS(ES+) calcd for $C_{12}H_{24}N_5O_6$ (M$^+$+H) 334.1727. found 334.1724.

(13) Synthesis of Example Compound 45

[Chemical Formula 168]

(Example compound 45)

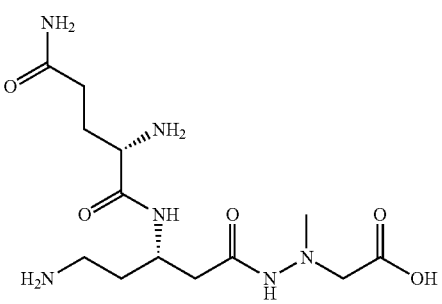

Synthesized by the same method as example compound 33 using compound 39m (48.2 mg, 85.7 µmol) (yellow solid, 20.5 mg, 35.7 µmol, two steps, 42%).

HRMS(ES+) calcd for $C_{13}H_{27}N_6O_5$ (M$^+$+H) 347.2043. found 347.2040.

(14) Synthesis of Example Compound 46

[Chemical Formula 169]

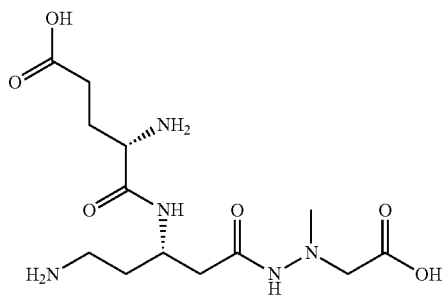

(Example compound 46)

Synthesized by the same method as example compound 33 using compound 39n (44.8 mg, 70.5 μmol) (green solid, 18.55 mg, 32.3 μmol, two steps, 46%).

HRMS(ES+) calcd for $C_{13}H_{26}N_5O_6$ (M$^+$+H) 348.1883. found 348.1873.

Example 13

Synthesis of Example Compound 47

(1) Synthesis of Compound 40 ((7S,10S)-2-bromobenzyl 7-(3-((tert-butoxycarbonyl)amino)propyl)-10-isobutyl-3,14,14-trimethyl-5,9,12-trioxo-13-oxa-3,4,8,11-tetraazapentadecan-1-oate)

[Chemical Formula 170]

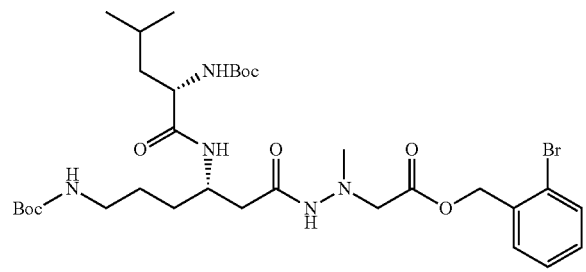

(Compound 40)

10% Pd/C (10.6 mg) was added to a methanol (2 mL) solution of compound 14 (106 mg, 0.158 mmol) under an argon atmosphere, hydrogen substitution was performed, and the solution was stirred for 35 minutes at room temperature. The reaction solution was filtered by Celite, and the solvent was distilled off under reduced pressure. The residue obtained was used in the next reaction without refining. Triethylamine (43.8 μL, 0.316 mmol) and (Boc)$_2$O (69.0 mg, 0.316 mmol) were added to a DMF (2 mL) solution of the residue while cooling by ice and stirred for 2 hours 30 minutes at room temperature. 1 M hydrochloric acid was added to the reaction solution while cooling by ice, followed by extraction by ethyl acetate. The organic layer was washed with saturated saline and dried by Na$_2$SO$_4$. After filtration, the mother liquor was distilled off under reduced pressure. The residue obtained was used in the next reaction without refining. o-Bromobenzyl alcohol (35.5 mg, 0.190 mmol) was added to a DMF (2 mL) solution of the residue obtained. N,N-dimethyl-4-aminopyridine (1.93 mg, 15.8 μmol) and N,N'-dicyclohexylcarbodiimide (35.9 mg, 0.174 mmol) were added while cooling by ice and stirred for 3 hours 20 minutes at room temperature. After distilling off the reaction solvent under reduced pressure, chloroform was added, and filtration was performed. The organic layer was washed with water and saturated saline and dried by Na$_2$SO$_4$. After filtration, the mother liquor was distilled off under reduced pressure, and a white solid was obtained by refining the residue obtained by silica gel chromatography (chloroform:methanol=100:1). (60.08 mg, 85.2 μmol, three steps, 54%).

$^1$H NMR (400 MHz, CDCl$_3$) δ 7.82 (s, 1H), 7.59 (d, J=7.9 Hz, 1H), 7.45-7.29 (m, 3H), 7.23 (t, J=6.3 Hz, 1H), 7.05 (brs, 1H), 5.35-5.20 (m, 2H), 5.03-4.90 (m, 1H), 4.80-4.63 (m, 1H), 4.35-4.12 (m, 1H), 4.12-3.96 (m, 1H), 3.81-3.51 (m, 2H), 3.26-3.03 (m, 2H), 2.97-2.43 (m, 4H), 2.39-2.20 (m, 1H), 1.78-1.50 (m, 6H), 1.43 (s, 18H), 0.93 (s, 6H); HRMS (ES+) calcd for $C_{32}H_{52}N_5O_8NaBr$ [M$^+$+Na] 736.2897. found 736.2919.

(2) Synthesis of Example Compound 47 (2-bromobenzyl 2-(2-((S)-6-amino-3-((S)-2-amino-4-methylpentanamido)hexanoyl)-1-methylhydrazinyl)acetate)

[Chemical Formula 171]

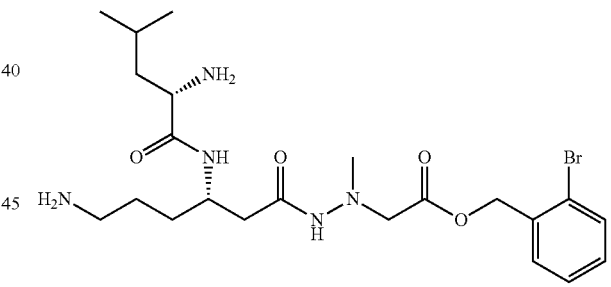

(Example compound 47)

4 M hydrochloric acid/dioxane (2 mL) was added to compound 40 (40.6 mg, 56.9 μmol) while cooling by ice and stirred for one hour at room temperature. The solvent was distilled off under reduced pressure, and the residue obtained was dissolved in water. A white solid was obtained by refining by high-performance liquid chromatography (solvent, H$_2$O in 0.1% TFA: CH$_3$CN in 0.1% TFA. A linear gradient of 25-45% CH$_3$CN in 0.1% TFA over 40 min. Flow rate 5 mL/min, detected at 222 nm UV). (21.7 mg, 29.3 μmol, 51%).

$^1$H NMR (400 MHz, D$_2$O) δ 8.35 (d, J=9.0 Hz, 1H), 7.69 (d, J=7.9 Hz, 1H), 7.55-7.47 (m, 1H), 7.43 (t, J=7.4 Hz, 1H), 7.33 (t, J=7.5 Hz, 1H), 5.30 (s, 2H), 4.30-4.24 (m, 1H), 4.02-3.85 (m, 1H), 3.80-3.60 (m, 2H), 3.07-2.90 (m, 2H), 2.64 (s, 3H), 2.34 (dd, J=15 and 5.2 Hz, 1H), 2.23 (dd, J=15 and 8.7 Hz, 1H), 1.80-1.44 (m, 7H), 0.93 (d, J=5.8 Hz, 6H); $^{13}$C NMR (100 MHz, D$_2$O) δ 173.6, 173.0, 172.8, 137.2, 135.9, 133.9, 133.6, 131.0, 126.3, 69.9, 61.4, 54.8, 49.6, 47.3, 43.2, 41.9, 41.7, 33.6, 26.8, 26.4, 24.8, 23.7; HRMS(ES+) calcd for $C_{22}H_{37}N_5O_4Br$ $[M^++H]^+$ 514.2029. found 514.2032.

Example 14

Synthesis of Example Compound 48

(1) Synthesis of Compound 41

Compound 41 ((S),(Z)-2-((tert-butoxycarbonyl)amino) undec-3-enoic acid) was synthesized with reference to the Journal of Peptide Synthesis, 19, 470-476, 2013.

(2) Synthesis of Compound 42 ((7S,10S)-benzyl 7-(2-azidoethyl)-3,14,14-trimethyl-10-((Z)-non-1-en-1-yl)-5,9,12-trioxo-13-oxa-3,4,8,11-tetraazapentadecan-1-oate)

[Chemical Formula 172]

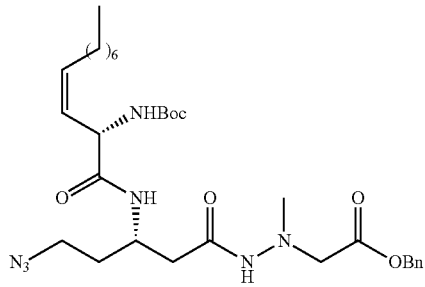

(Compound 42)

4 M hydrochloric acid/dioxane (2 mL) was added to compound 41 (90.0 mg, 0.207 mmol) while cooling by ice and stirred for 1 hour 15 minutes at room temperature. The solvent was distilled off under reduced pressure, and the residue obtained was used in the next reaction without refining. The residue was dissolved in DMF (2 mL), and (S),(Z)-2-((tert-butoxycarbonyl)amino)undec-3-enoic acid (0.372 mmol) and HOBt.H$_2$O (57.0 mg, 0.372 mmol) were added. Triethylamine (51.8 μL, 0.372 mmol) and EDC.HCl (71.3 mg, 0.372 mmol) were added sequentially while cooling by ice and stirred overnight at room temperature. The reaction solution was added to 10% citric acid aqueous solution and extracted by ethyl acetate. The organic layer was washed with saturated sodium bicarbonate aqueous solution, water, and saturated saline, and dried by Na$_2$SO$_4$. After filtration, the mother liquor was distilled off under reduced pressure, and a white solid was obtained by refining the residue obtained by silica gel chromatography (chloroform:methanol=100:1). (109 mg, 0.176 mmol, two steps, 85%).

$^1$H NMR (400 MHz, CDCl$_3$) δ7.76 (s, 1H), 7.43-7.33 (m, 5H), 5.62-5.52 (m, 1H), 5.45-5.22 (m, 1H), 5.18 (s, 2H), 4.95 (brs, 1H), 4.41-4.19 (m, 1H), 4.11-3.96 (m, 1H), 3.80-3.49 (m, 2H), 3.40-3.29 (m, 2H), 3.04-2.23 (m, 7H), 2.09-1.70 (m, 3H), 1.44 (s, 9H), 1.39-1.18 (m, 10H), 0.88 (t, J=6.6 Hz, 3H); HRMS(ES+) calcd for $C_{31}H_{50}N_7O_6$ $[M^++H]^+$ 616.3823. found 616.3813.

(3) Synthesis of Example Compound 48 (2-(2-((S)-5-amino-3-((S)-2-aminoundecanamido)pentanoyl)-1-methylhydrazinyl)acetic acid)

[Chemical Formula 173]

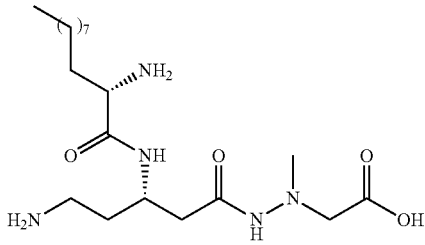

(Example compound 48)

PtO$_2$ (8.8 mg) was added to a methanol (2 mL) solution of compound 42 (18.8 mg, 30.5 μmol) under an argon atmosphere, hydrogen substitution was performed, and the solution was stirred for two hours at room temperature. The reaction solution was filtered by Celite, and the solvent was distilled off under reduced pressure. The residue obtained was used in the next reaction without refining. 4 M hydrochloric acid/dioxane (2 mL) was added to the residue while cooling by ice and stirred for 30 minutes at room temperature. The solvent was distilled off under reduced pressure, and the residue obtained was dissolved in water. A white cottony substance was obtained by refining by high-performance liquid chromatography (solvent, H$_2$O in 0.1% TFA: CH$_3$CN in 0.1% TFA. A linear gradient of 40-50% CH$_3$CN in 0.1% TFA over 40 min. Flow rate 5 mL/min, detected at 222 nm UV). (5.52 mg, 8.77 μmol, two steps, 29%)

$^1$H NMR (400 MHz, D$_2$O) δ4.40-4.26 (m, 1H), 3.98-3.90 (m, 1H), 3.73-3.57 (m, 2H), 3.13-2.94 (m, 2H), 2.75-2.66 (m, 3H), 2.52 (dd, J=5.2 and 15 Hz, 1H), 2.40 (dd, J=8.7 and 15 Hz, 1H), 2.07-1.75 (m, 4H), 1.40-1.16 (m, 14H), 0.85 (t, J=7.0 Hz, 3H); HRMS (ES+) calcd for $C_{19}H_{40}N_5O_4$ $[M^++H]^+$ 402.3080. found 402.3098.

Example 15

Synthesis of Example Compound 49

[Chemical Formula 174]

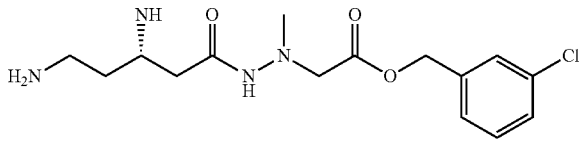

(Example compound 49)

Example compound 49 was synthesized by the same method as compound 24a, example compound 20 using compound 22a (100 mg, 0.197 mmol) and 3-chlorobenzyl alcohol (34.4 mg, 0.242 mmol) (white solid, 14.0 mg, three steps, 49%).

$^1$H NMR (400 MHz, D$_2$O) δ7.49-7.30 (m, 4H), 5.18 (s, 2H), 3.76-3.60 (m, 3H), 3.08 (t, J=8.6 Hz, 2H), 2.65 (s, 3H), 2.61-2.47 (m, 2H), 2.15-1.82 (m, 2H); HRMS(ES+) calcd for $C_{15}H_{24}N_4O_3Cl$ $[M^++H]^+$ 343.1537. found 343.1535.

B. Measurement of Read-Through Activity

Example 16

In Vitro Evaluation (1) Cell Culture

African green monkey SV40-transformed kidney fibroblast cell line (COS-7) was sown in 100×20 mm cell culture dishes manufactured by Falcon and cultured at 37° C. in 5% $CO_2$. Fifty milliliters of fetal bovine serum (FBS) was added to 500 mL of D-MEM (containing high glucose, L-glutamine, and phenol red) manufactured by Wako Pure Chemical Industries Ltd., and culture broth prepared to adjust to 10% FBS was used as the culture broth. (Referred to hereinafter as culture broth.)

(2) Evaluation of Read-Through Activity

The Reporter Lysis Buffer 5×, assay 2× buffer, 1 M $Na_2CO_3$, and standard used in creation of the calibration curve referred to hereinafter are included in the β-Galactosidase Enzyme Assay System with Reporter Lysis Buffer manufactured by Promega.

COS-7 cells ($8.0 \times 10^3$ cells/well) were seeded by continuous dispensing of 100 μL each into flat-bottom 96-well plates (Costar (registered trade mark) 3596) manufactured by Corning and incubated for 15-16 hours at 37° C.

A quantity of 4 μL/well of DNA solution prepared in a ratio of 1.32 μL (2 μg) of reporter gene (a construct obtained by linking a β-galactosidase gene and a luciferase gene and inserting a premature stop codon (TGA) at their juncture), 100 μL of OPTI-MEM (registered trade mark) I (Reduced Serum Medium 1×) manufactured by Invitrogen, and 4 μL of FuGENE (registered trade mark) HD Transfection Reagent manufactured by Roche was added to the solution and incubated for 10-11 hours at 37° C.

The entire culture broth was aspirated, and the compound to be evaluated was prepared to adjust to 200 μM by culture broth and added by continuously dispensing 200 μL/well. 100 μM and 50 μM were also prepared in the same way and added by continuously dispensing 200 μL each. Incubation was carried out for 48 hours at 37° C. after addition.

After 48 hours had elapsed, the entire culture broth in the well was aspirated and washed twice with PBS. The Reporter Lysis Buffer 5× was then diluted by MilliQ, and a solution prepared to adjust to Reporter Lysis Buffer 1× was added by continuously dispensing 100 μL each and allowed to stand for 15 minutes at room temperature. The contents of each well were recovered thereafter, and the entire amount was transferred to Nunc microwell plates (V bottom) manufactured by Thermo Fisher Scientific and centrifuged (1800 rpm, 15 minutes). Eighty-five microliters of this lysate was transferred to Nunc low-binding 96-well plates (flat bottom) clear manufactured by Thermo Fisher Scientific.

<Evaluation of β-Galactosidase Activity>

Using Nunc low-binding 96-well plates (flat bottom) clear manufactured by Thermo Fisher Scientific, 30 μL/well of Reporter Lysis Buffer 1× was added by dispensing continuously, followed by addition of 20 μL of the recovered lysate to make 50 μL. Separately, the standard required for creation of a calibration curve was added to make 0, 1, 2, 3, 4, and 5 mU according to the protocol of the β-Galactosidase Enzyme Assay System with Reporter Lysis Buffer manufactured by Promega. A quantity of 50 μL of Assay 2× buffer was added to each of these wells and incubated for 25 minutes at room temperature. A quantity of 150 μL/well of 1M $Na_2CO_3$, a reaction-stopping solution, was added, and the emission intensity (420 nm, reference 0 nm) was measured immediately using an absorption/fluorescence microplate reader Tecan Safire manufactured by Tecan. A calibration curve was created from the absorbance of the standard, and the absorbance converted to mU according to this calibration curve was taken as the activity value.

<Evaluation of Luciferase Activity>

A quantity of 50 μL/well of the recovered lysate was added to 96-well white plates (Costar (registered trade mark) 3912) manufactured by Corning and incubated for five minutes at room temperature after adding 100 μL of PicaGene (registered trade mark) manufactured by Toyo Ink Co., Ltd. After five minutes, the emission intensity was measured by a Berthold luminometer MicroLumat Plus LB96V manufactured by Berthold Japan.

<Calculation of Read-Through Efficiency>

The value obtained by dividing the luciferase activity by the β-galactosidase activity measured above was used.

The read-through activity was evaluated using example compound 2 synthesized in Example 1, example compound 3 synthesized in Example 5, and example compound 1 and example compound 4 synthesized separately by the same method. The results are shown in FIG. 1. It is understood from FIG. 1 that example compounds 1-4 have read-through activity in the same way as negamycin, and that example compound 3 in particular has remarkably high read-through efficiency.

Figure 2:
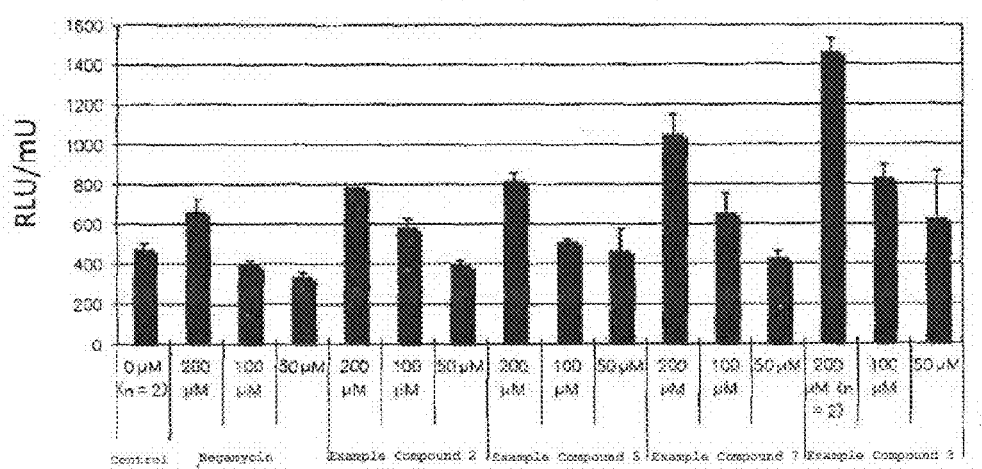
FIG. 2 is a graph showing the results of in vitro measurement of the read-through activity of compounds of the present invention.

Next, the read-through activity of example compound 5, obtained by esterifying the end carboxyl group of example compound 2, and example compound 7, obtained by introducing an N-linked amino acid group at position 3 of example compound 2, was evaluated. FIG. 2 shows the results obtained by evaluating the read-through activity of these compounds, example compound 2, example compound 3, and negamycin. FIG. 2 shows that example compounds 2, 3, 5, and 7 have remarkably high read-through efficiency in comparison even to negamycin.

Figure 3:
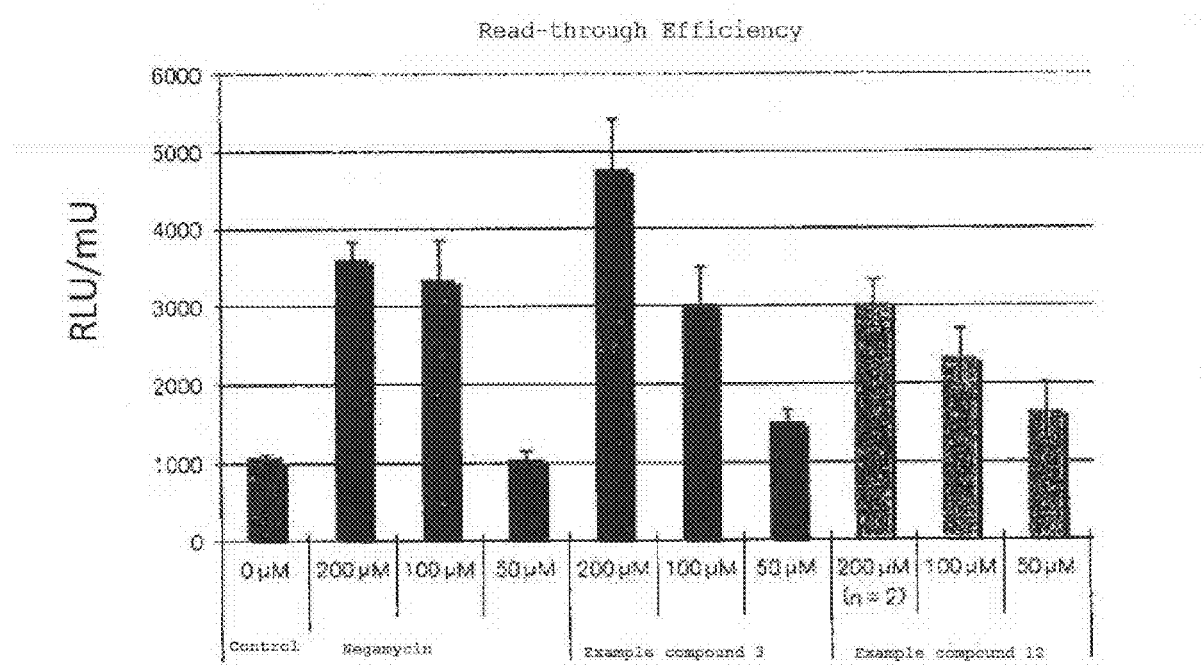
FIG. 3 is a graph showing the results of in vitro measurement of the read-through activity of compounds of the present invention.

The read-through activity of example compound 3 included in general formula (3) and example compound 12, obtained by introducing an N-linked amino acid group at position 3 thereof, was also evaluated. FIG. 3 shows that these compounds which have fewer carbon atoms in the main chain than example compound 2 also have read-through efficiency equal to or greater than that of negamycin.

Example 17

The read-through activity of example compounds 14-46 obtained in Examples 6-12 was evaluated by the same method as in Example 16. The results are shown below in Table 1.

TABLE 1

| Example Compound | Read-through Activity |
|---|---|
| 14 | 2.13 ± 0.08 |
| 15 | 1.92 ± 0.21 |
| 16 | 1.87 ± 0.29 |
| 17 | 2.10 ± 0.90 |
| 18 | 1.30 ± 0.09 |
| 19 | 3.25 ± 0.07 |
| 20 | 7.07 ± 0.45 |
| 21 | 7.04 ± 0.14 |

TABLE 1-continued

| Example Compound | Read-through Activity |
|---|---|
| 22 | 5.18 ± 0.04 |
| 23 | 5.65 ± 0.09 |
| 24 | 3.89 ± 0.16 |
| 25 | 1.26 ± 0.07 |
| 26 | 1.44 ± 0.04 |
| 27 | 1.64 ± 0.12 |
| 28 | 1.40 ± 0.04 |
| 29 | 2.84 ± 0.06 |
| 30 | 1.70 ± 0.06 |
| 31 | 1.75 ± 0.02 |
| 32 | 1.24 ± 0.09 |
| 33 | 2.34 ± 0.11 |
| 34 | 2.00 ± 0.13 |
| 35 | 3.09 ± 0.62 |
| 36 | 1.92 ± 0.40 |
| 37 | 2.78 ± 0.67 |
| 38 | 1.75 ± 0.19 |
| 39 | 1.63 ± 0.14 |
| 40 | 1.50 ± 0.05 |
| 41 | 1.57 ± 0.05 |
| 42 | 2.14 ± 0.18 |
| 43 | 2.20 ± 0.05 |
| 44 | 1.58 ± 0.05 |
| 45 | 1.65 ± 0.18 |
| 46 | 1.60 ± 0.13 |

When negamycin was evaluated under the same conditions, the read-through activity was 1.53±0.04. As shown in Table 1, all of the example compounds of the present invention have read-through activity approximately equal to or greater than that of negamycin.

Example 18

In Vivo Evaluation

Transgenic mice were produced by introducing a luciferase gene and δ-galactosidase gene as reporter genes by the method described in International Publication WO2008/004610 pamphlet.

A physiological saline solution of example compound 2 synthesized in Example 1 was administered subcutaneously to the abdomen of the transgenic mice produced every 24 hours for seven consecutive days. On the eighth day, the rectus femoris and the gastrosoleus muscle of the mice were excised. After mincing by ophthalmological scissors, three times the wet weight of Reporter Lysis Buffer (Promega, US) was added, and the tissue was disrupted by Physcotron (Nition Co., Ltd.). After freezing overnight and thawing, the supernatant obtained by centrifugation was introduced into a 96-well plate, and the β-galactosidase activity was measured by a Beta-Glo Assay System (Promega, US) and the luciferase activity was measured by a Bright-Glo Assay System (Promega, US). A luminometer (ATTO) was used in measurement. The luciferase activity value was divided by the δ-galactosidase activity value, and the value multiplied by $10^4$ was taken as the read-through efficiency.

Figure 4:
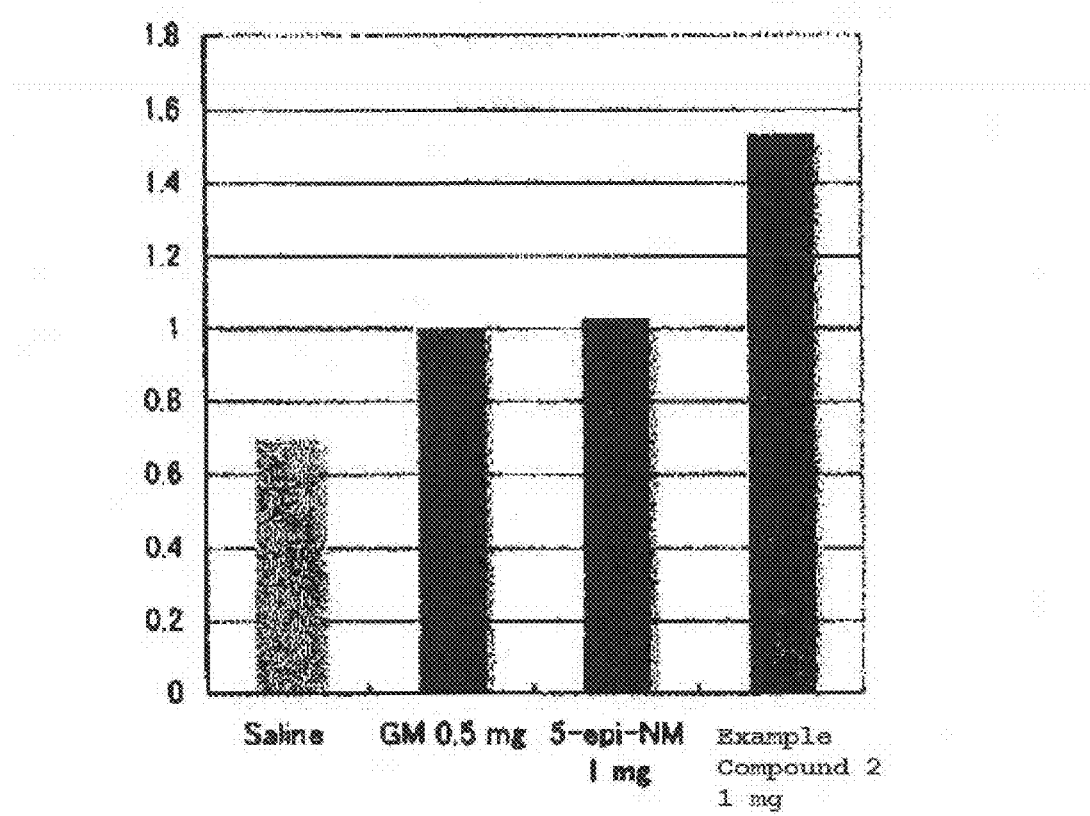
FIG. 4 is a graph showing the results of in vivo measurement of the read-through activity of compounds of the present invention.

FIG. 4 shows the results of measurement of the read-through activity of gentamicin, 5-epi-negamycin, and example compound 2 of the present invention. Example compound 2 of the present invention was found to have read-through activity and had high read-through activity even in comparison to gentamicin and 5-epi-negamycin.

Example 19

Figure 5:
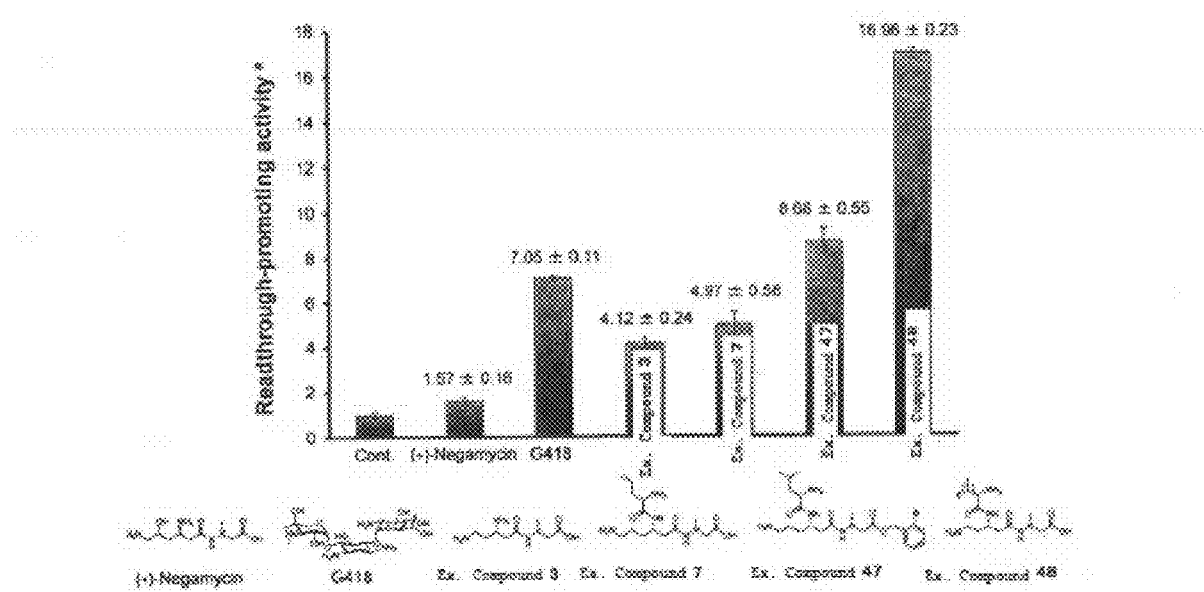
FIG. 5 is a graph showing the results of in vitro measurement of the read-through activity of example compounds 3, 7, 47, and 48.

The read-through activity of example compounds 3, 7, 47, and 48 was evaluated by the same method as in Example 16. The results are shown in FIG. 5.

Here, Geneticin purchased from Roche was used as G418.

Example 20

In order to investigate the effects of the alkyl chain length of $R_{12}$ of the N-linked amino acid residue represented by general formula (4), compounds (alkyl chains C4, C5, C7, and C11) of varied alkyl chain length of $R_{12}$ in relationship to compound 48 were synthesized, and the read-through activity was evaluated by the same method as in Example 16. The results are shown in FIG. 6.

Figure 6:
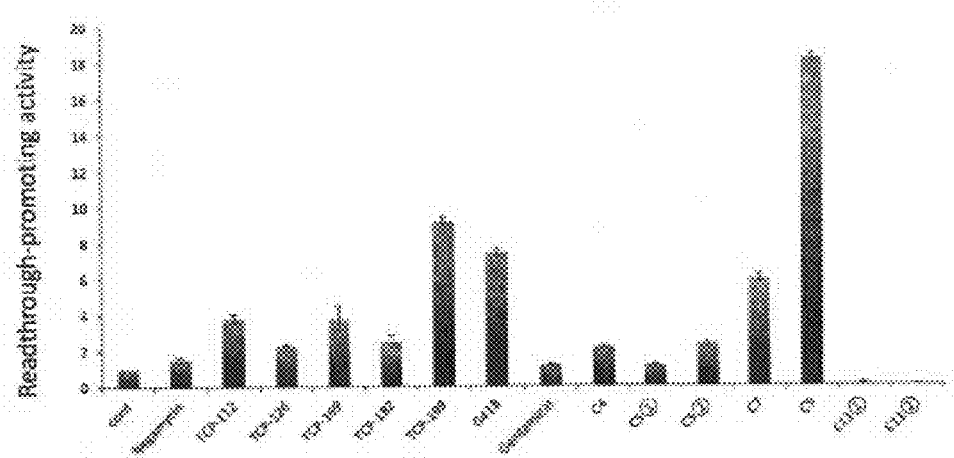
FIG. 6 is a graph showing the results of studying the relationship between the alkyl chain length of $R_{12}$ of an N-linked amino acid residue and the read-through activity.

Furthermore, since products of the same molecular weight were obtained for C5 and C11 in FIG. 6, the measurement results of the two are shown (C5(1) and C5(2), C11(1) and C11 (2)).

The invention claimed is:

1. A compound represented by formula (1):

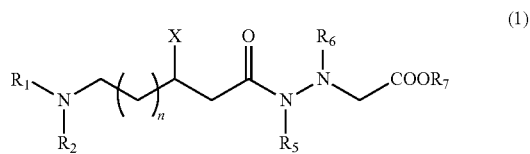

(1)

in which $R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group, $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, and the heterocycle or heteroaryl may be substituted by a $C_1$-$C_6$ alkyl group, $C_2$-$C_6$ alkenyl, or $C_2$-$C_6$ alkynyl, $C_6$-$C_{10}$ aralkyl group, or $C_6$-$C_{10}$ aralkenyl group, one or both of $R_1$ and $R_2$ may be an amino acid residue introduced via an amide bond formed together with the nitrogen atom to which they are bonded;

X is $N(R_3)(R_4)$, an N-linked amino acid residue, or a $C_1$-$C_6$ alkyl group containing an amino group having a substituent, where the substituent of the amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_5$ is a hydrogen, $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_7$ is a $C_1$-$C_6$ alkyl group, substituted or unsubstituted aralkyl group, or $C_3$-$C_7$ cycloalkyl group, where the substituent of the substituted aralkyl group is a halogen, $C_1$-$C_4$ alkyl group, alkoxy group, hydroxy group, nitro group, amino group, $C_1$-$C_6$ acyl group, or amino group modified by an alkyl group, or a sulfonic acid group; and n is an integer of 0-3, or a pharmaceutically acceptable salt or solvate of the compound.

2. The compound according to claim 1 represented by formula (3):

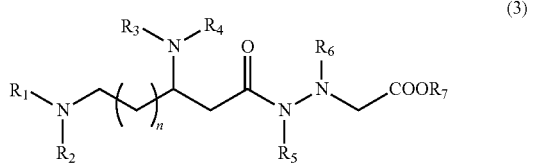

h $R_1$, $R_2$, $R_3$, $R_4$, $R_5$, $R_6$, $R_7$, and n are as defined in claim 1, or a salt or solvate of the compound.

3. The compound according to claim 1, wherein the N-linked amino acid residue of X is selected from α-amino acids and β-amino acids, or a pharmaceutically acceptable salt or solvate of the compound.

4. The compound according to claim 1 represented by formula (5):

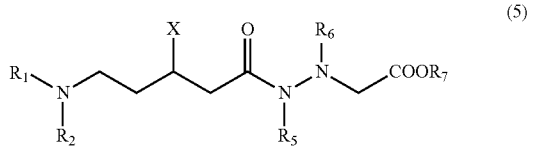

in which $R_1$, $R_2$, X, $R_3$, $R_4$, $R_5$, $R_6$, and $R_7$ are as defined in claim 1, or a pharmaceutically acceptable salt or solvate of the compound.

5. A compound represented by formula (1):

[Chemical Formula 6]

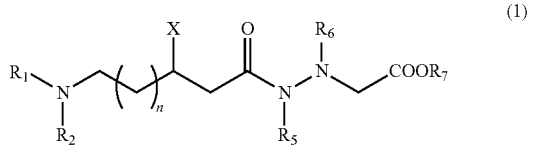

wherein at least one of $R_1$ and $R_2$ are an amino acid residue introduced via an amide bond formed together with the nitrogen atom to which they are bonded, the remaining $R_1$ or $R_2$ is hydrogen, and the amino acid residue is represented by the following formula (2):

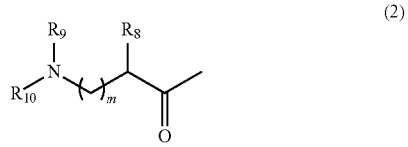

X is $N(R_3)(R_4)$, an N-linked amino acid residue, or a $C_1$-$C_6$ alkyl group containing an amino group having a substituent, where the substituent of the amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group, and wherein the N-linked amino acid residue is an α-amino acid residue or β-amino acid residue comprising a $C_1$-$C_{12}$ side chain, and the α-amino acid is selected from the group consisting of isoleucine, valine, lysine, ornithine, threonine, arginine, asparagine, aspartic acid, glutamine, glutamic acid, serine, histidine, phenylalanine, alanine, glycine, tryptophan, tyrosine, N-methylleucine, 2,3-diaminopropanoic acid, 2,4-diaminobutyric acid, ornithine, lysine, and α-hydroxyleucine;

$R_5$ is a hydrogen, $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_7$ is hydrogen, a $C_1$-$C_6$ alkyl group, substituted or unsubstituted aralkyl group, or $C_3$-$C_7$ cycloalkyl group, where the substituent of the substituted aralkyl group is a halogen, $C_1$-$C_4$ alkyl group, alkoxy group, hydroxy group, nitro group, amino group, $C_1$-$C_6$ acyl group, or amino group modified by an alkyl group, or a sulfonic acid group;

n is an integer of 0-3;

$R_8$ is hydrogen, an optionally substituted $C_1$-$C_{10}$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, where substituents that these substituents can have are a halogen, hydroxyl group, carboxyl group, amino group, or amide group;

$R_9$, $R_{10}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_9$ and $R_{10}$ also may form, together with the nitrogen atom to which they are bonded, a three- to six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group; and m is an integer of 0-4, or a pharmaceutically acceptable salt or solvate of the compound.

6. A compound represented by formula (1):

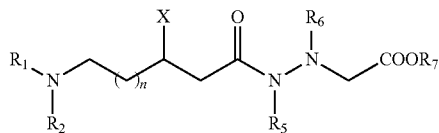

(1)

wherein $R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group, $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, and the heterocycle or heteroaryl may be substituted by a $C_1$-$C_6$ alkyl group, $C_2$-$C_6$ alkenyl, or $C_2$-$C_6$ alkynyl, $C_6$-$C_{10}$ aralkyl group, or $C_6$-$C_{10}$ aralkenyl group, one or both of $R_1$ and $R_2$ may be an amino acid residue introduced via an amide bond formed together with the nitrogen atom to which they are bonded;

$R_5$ is a hydrogen, $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, $C_6$-$C_{10}$ aralkenyl group;

$R_7$ is hydrogen, a $C_1$-$C_6$ alkyl group, substituted or unsubstituted aralkyl group, or $C_3$-$C_7$ cycloalkyl group, where the substituent of the substituted aralkyl group is a halogen, $C_1$-$C_4$ alkyl group, alkoxy group, hydroxy group, nitro group, amino group, $C_1$-$C_6$ acyl group, or amino group modified by an alkyl group, or a sulfonic acid group;

n is an integer of 0-3;

the N-linked amino acid residue of X is represented by the following formula (4):

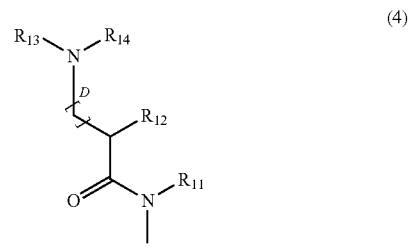

(4)

in which $R_{11}$ is hydrogen or an optionally substituted $C_1$-$C_6$ alkyl group;

$R_{12}$ is hydrogen, an optionally substituted $C_7$-$C_9$ alkyl group, $C_2$-$C_{10}$ alkenyl group, $C_2$-$C_{10}$ alkynyl group, $C_6$-$C_{10}$ aralkyl group, or $C_6$-$C_{10}$ aralkenyl group, where substituents that these substituents can have are a halogen, hydroxyl group, carboxyl group, amino group, or amide group;

$R_{13}$, $R_{14}$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_8$ and $R_9$ also may form, together with the nitrogen atom to which they are bonded, a three- to six-membered heterocycle or heteroaryl bonded via N, may also contain 1-3 additional hetero atoms selected from the group consisting of O, N, and S as ring constituent members (for example, oxazolidine), where the heterocycle or heteroaryl may be substituted by a $C_1$-$C_6$ alkyl, $C_2$-$C_6$ alkenyl, or $C_2$-$C_6$ alkynyl, $C_6$-$C_{10}$ aralkyl group, $C_6$-$C_{10}$ aralkenyl group; and p is an integer of 0-3, or a pharmaceutically acceptable salt or solvate of the compound.

7. A method of inducing read-through activity through a nonsense mutation in a subject in need thereof, comprising administering to said subject a pharmaceutical composition comprising a compound represented by the following general formula (1):

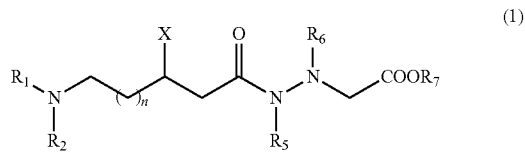

(1)

in which $R_1$ and $R_2$ are each independently hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, sulfonyl group, cyclic amine, or guanidyl group, $R_1$ and $R_2$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, or $C_6$-$C_{10}$ aralkenyl group, one or both of $R_1$ and $R_2$ may be an amino acid residue introduced via an amide bond formed together with the nitrogen atom to which they are bonded;

X is $N(R_3)(R_4)$, an N-linked amino acid residue, or $C_1$-$C_6$ alkyl group containing an amino group having a substituent, where the substituent of this amino group is hydrogen, an optionally substituted $C_1$-$C_6$ alkyl group, $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, where $R_3$ and $R_4$ are each independently hydrogen or an optionally substituted $C_1$-$C_6$ alkyl group, $R_3$ and $R_4$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, or $C_6$-$C_{10}$ aralkenyl group;

$R_5$ is a hydrogen, $C_1$-$C_4$ alkyl group, $C_2$-$C_4$ alkenyl group, or $C_2$-$C_4$ alkynyl group;

$R_6$ is a $C_1$-$C_4$ alkyl group, $C_2$-$C_4$ alkenyl group, $C_2$-$C_4$ alkynyl group, $C_3$-$C_6$ cycloalkyl group, carboxyl group, carboxylate group, alkyl group having a carboxyl group or carboxylate group; $C_2$-$C_6$ alkenyl group, $C_2$-$C_6$ alkynyl group, $C_6$-$C_{10}$ aralkyl group, $C_6$-$C_{10}$ aralkenyl group, cyclic amine, or guanidyl group, $R_5$ and $R_6$ also may form, together with the nitrogen atom to which they are bonded, a five-membered or six-membered heterocycle or heteroaryl bonded via N, may also contain 1-3 additional hetero atoms selected from the group consisting of O, N, and S as ring constituent members, where the heterocycle or heteroaryl may be substituted by a $C_1$-$C_6$ alkyl group, $C_2$-$C_6$ alkenyl group, or $C_2$-$C_6$ alkynyl group, $C_6$-$C_{10}$ aralkyl group, or $C_6$-$C_{10}$ aralkenyl group;

$R_7$ is hydrogen, a $C_1$-$C_6$ alkyl group, substituted or unsubstituted aralkyl group, or $C_3$-$C_7$ cycloalkyl group, where the substituent of a substituted aralkyl group is a halogen, $C_1$-$C_4$ alkyl group, alkoxy group, hydroxy group, nitro group, amino group, $C_1$-$C_6$ acyl group, or amino group modified by an alkyl group, or sulfonic acid group; and n is an integer of 0-3, or a pharmaceutically acceptable salt or solvate of the compound.

8. The method of claim 7, wherein the compound is represented by the following general formula (5):

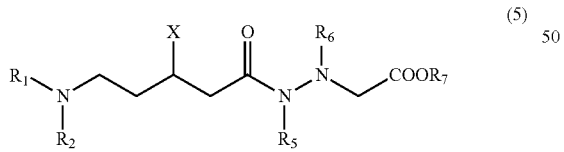

(5)

in which $R_1$, $R_2$, X, $R_3$, $R_4$, $R_5$, $R_6$, and $R_7$ are as defined in claim 7, or a pharmaceutically acceptable salt or solvate of the compound.

9. The method according to claim 7 or 8 wherein the subject has a disease caused by a nonsense mutation.

10. The method of claim 7, wherein the subject has a disease selected from the group consisting of muscular dystrophy, Duchenne muscular dystrophy, infantile neuronal ceroid lipofuscinosis, multiple sclerosis, Alzheimer's disease, Tay-Sachs disease, neurodegenerative disease, Parkinson's disease, rheumatoid arthritis, graft-versus-host disease, arthritis, hemophilia, von Willebrand disease, ataxia telangiectasia, β-thalassemia, kidney stones, osteogenesis imperfecta, liver cirrhosis, neurofibromatosis, bullous disease, lysosomal storage disease, Hurler disease, familial hypercholesterolemia, cerebellar ataxia, nodular sclerosis, immunodeficiency, kidney disease, lung disease, cystic fibrosis, familial cholesterolemia, pigmentary retinopathy, amyloidosis, atherosclerosis, gigantism, dwarfism, hypothyroidism, hyperthyroidism, aging, obesity, Niemann-Pick disease, and Marfan syndrome.

11. The method of claim 10, wherein the disease is selected from the group consisting of muscular dystrophy, cystic fibrosis, Hurler disease, and infantile neuronal ceroid lipofuscinosis.

12. A compound selected from the group consisting of the following compounds, or a pharmaceutically acceptable salt or solvate of the compound:

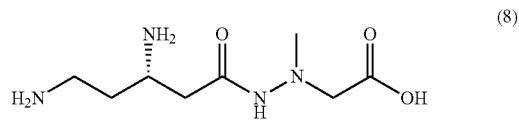

(8)

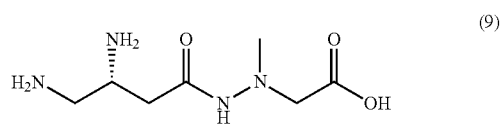

(9)

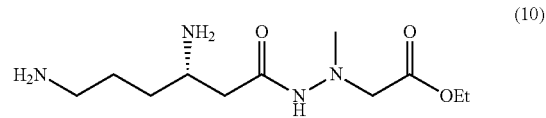 [SMILES: CCOC(=O)CN(C)NC(=O)C[C@@H](N)CCCN]

(10)

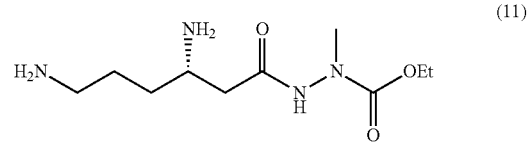 [SMILES: CCOC(=O)N(C)NC(=O)C[C@@H](N)CCCN]

(11)

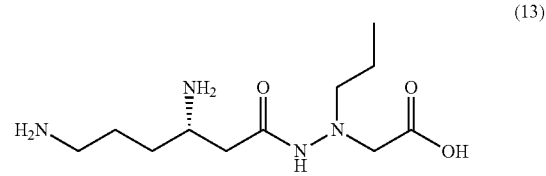 [SMILES: CCCN(CC(=O)O)NC(=O)C[C@@H](N)CCCN]

(13)

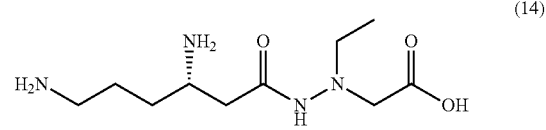 [SMILES: CCN(CC(=O)O)NC(=O)C[C@@H](N)CCCN]

(14)

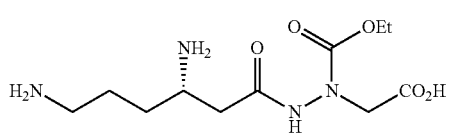
(15)
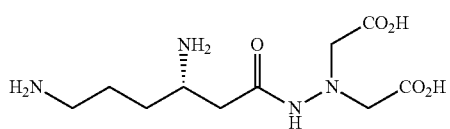
(16)
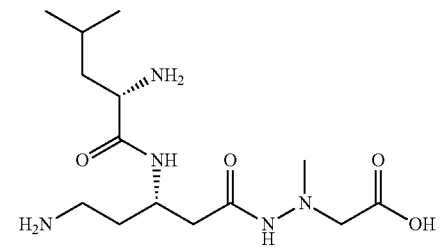
(17)
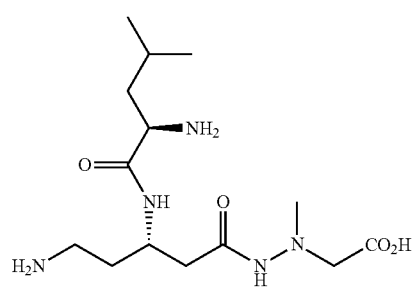
(18)
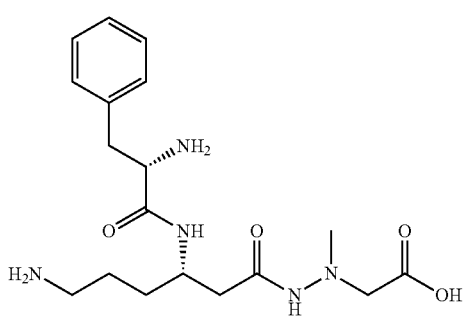
(19)
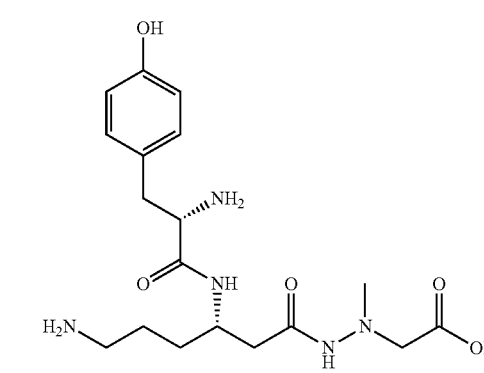
(20)
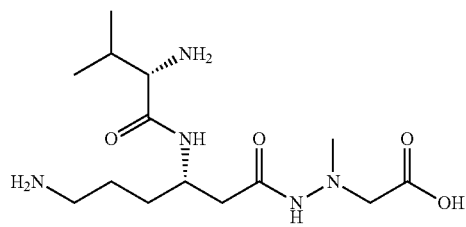
(21)
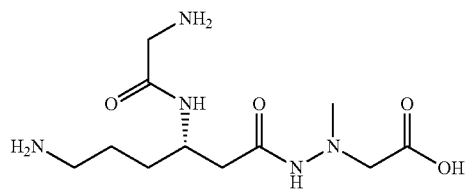
(22)
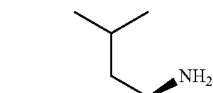
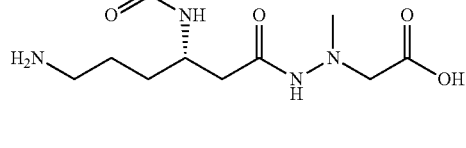
(23)
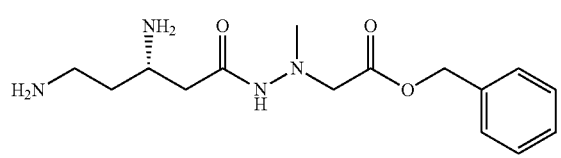
(24)

89 90
(25) 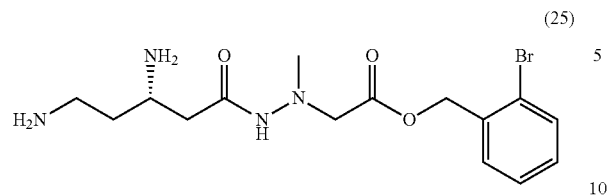
(31) 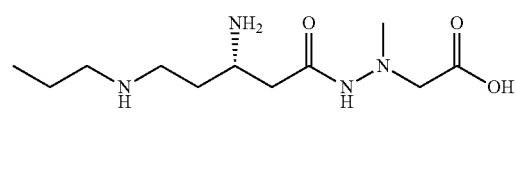
(26) 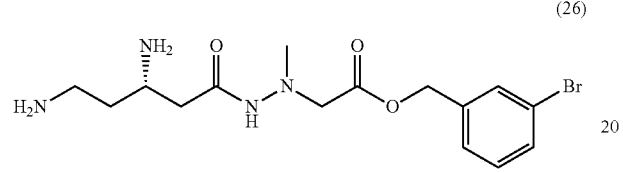
(32)
(27) 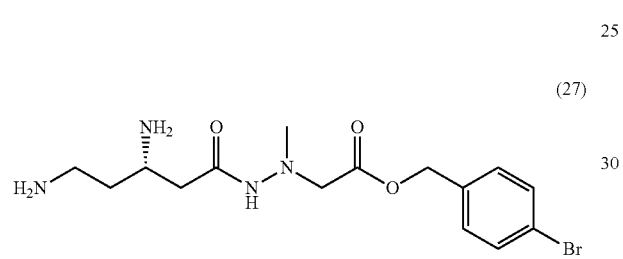
(33)
(28) 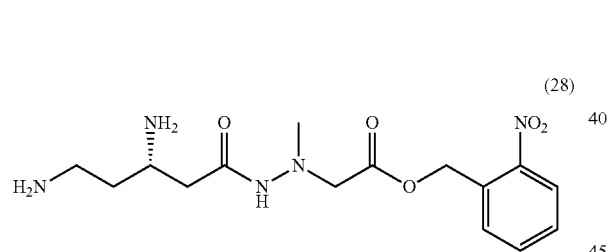
(34) 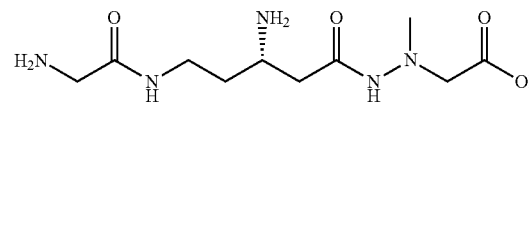
(29)
(35)
(30) 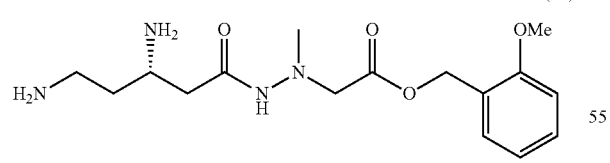
(36) 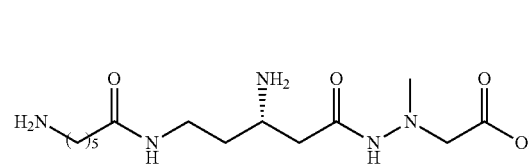
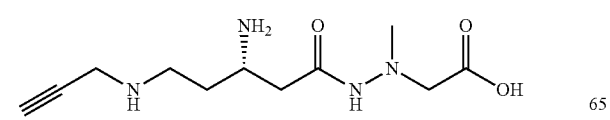
(37) 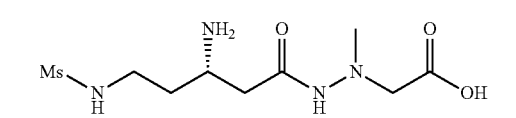

91
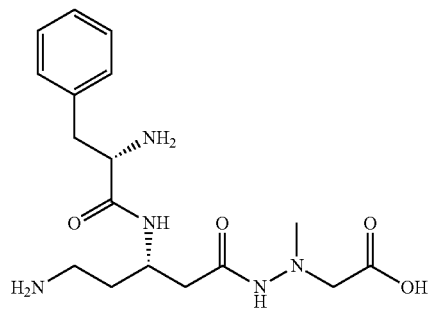
(38)
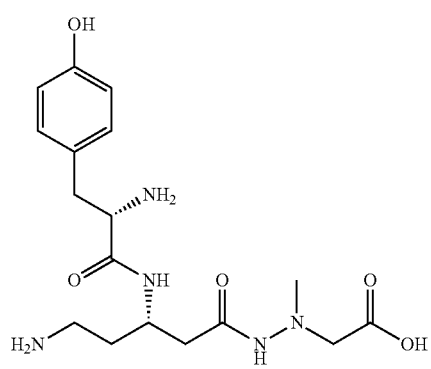
(39)
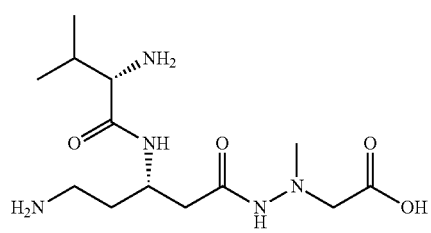
(40)
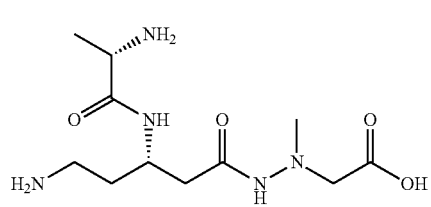
(41)
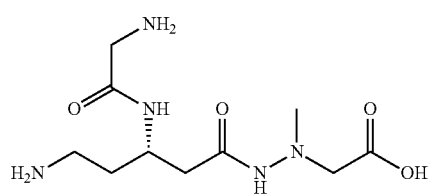
(42)
92
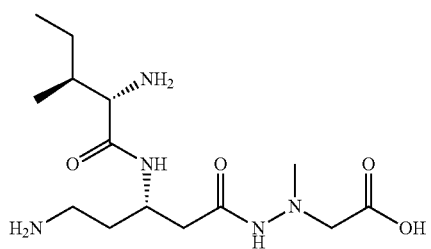
(43)
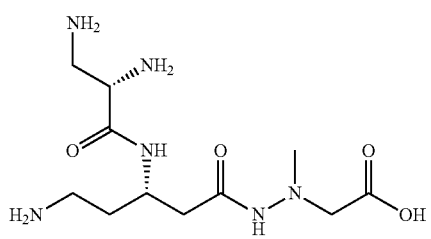
(44)
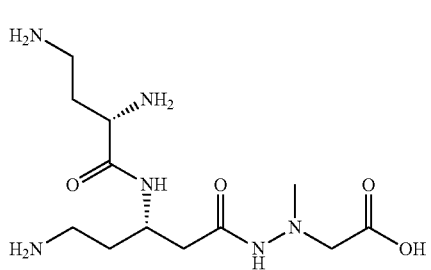
(45)
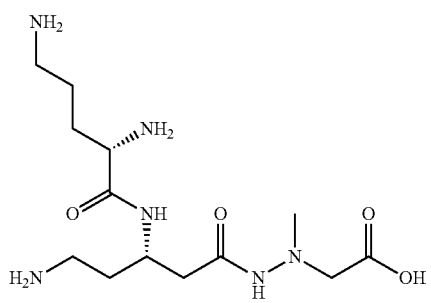
(46)
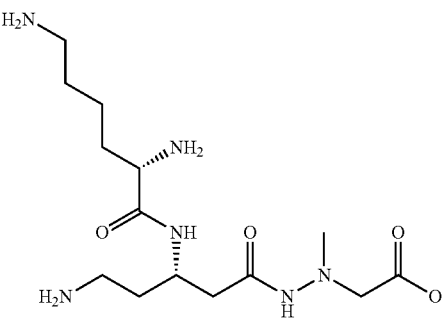
(47)

(48)
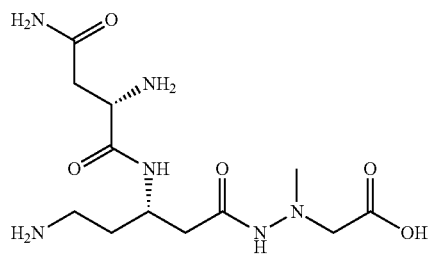
(51)
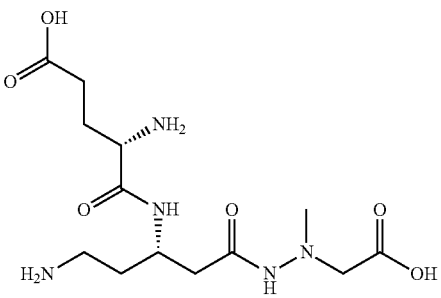
(49)
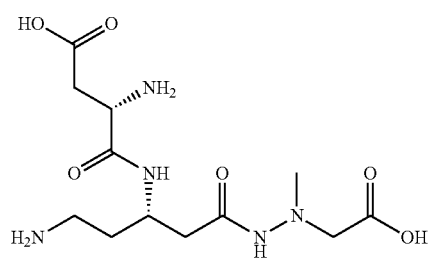
(54)
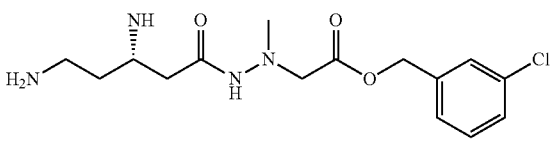
13. A compound selected from the group consisting of the following compounds 52 and 53, or a pharmaceutically acceptable salt or solvate of the compound:
(52)
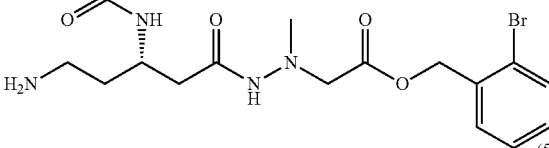
(50)
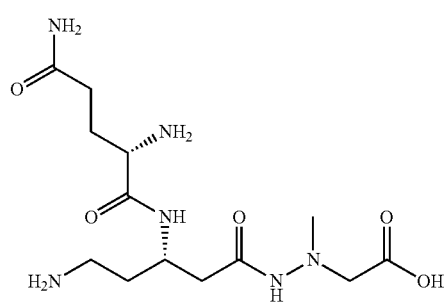
(53)
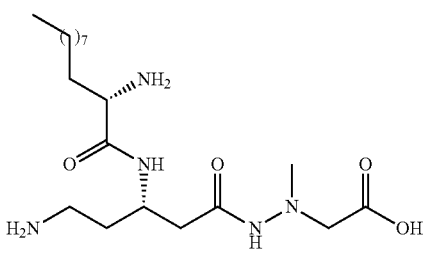
* * * * *